United States Patent [19]

Osborne et al.

[11] Patent Number: 5,807,333
[45] Date of Patent: Sep. 15, 1998

[54] PERISTALTIC PUMP AND FLUID DELIVERY SET

[75] Inventors: Robert Scott Osborne, Gahanna; Carl Joseph Piontek, Powell; Robert Donald Clegg, Pickerington; Bradford Lynn Buck, Gahanna; Matthew Scott Fleming, Columbus; Joseph Anthony Juratovac, Columbus; Dennis John Hoffman, Columbus; Grant Richard Wilson, Columbus; William Edward Patton, Dublin, all of Ohio

[73] Assignee: Abbott Laboratories, Abbott Park, Ill.

[21] Appl. No.: 531,577

[22] Filed: Sep. 21, 1995

[51] Int. Cl.⁶ .................................................. A61M 37/00
[52] U.S. Cl. .......................................... 604/131; 604/151
[58] Field of Search ............................ 604/131, 151, 604/153, 67; 122/DIG. 13; 417/474, 476

[56] References Cited

U.S. PATENT DOCUMENTS

| | | | |
|---|---|---|---|
| 5,057,081 | 10/1991 | Sunderland | 417/474 X |
| 5,147,313 | 9/1992 | Dikeman | 604/153 |
| 5,374,251 | 12/1994 | Smith . | |
| 5,562,615 | 10/1996 | Nassif | 604/67 |
| 5,584,671 | 12/1996 | Schweitzer, Jr. et al. | 604/151 |
| 5,594,981 | 1/1997 | Piontek et al. | 29/235 |
| 5,617,626 | 4/1997 | Piontek et al. | 29/450 |

FOREIGN PATENT DOCUMENTS

WO 92/06720  4/1992  WIPO .

*Primary Examiner*—John D. Yasko
*Attorney, Agent, or Firm*—Brian R. Woodworth

[57] ABSTRACT

An apparatus for supplying an enteral or parenteral fluid to a patient is a cooperative assembly of a rotary peristaltic pump and a fluid delivery set. The peristaltic pump has (a) a housing and (b) a peristaltic rotor projecting from the housing on a rotatable drive shaft. The housing has first and second receptacles for retaining and supporting the fluid delivery set. The fluid delivery set has (a) a drip chamber, or sight chamber, (b) a plurality of lengths or segments of flexible tubing, and (c) fluid connection elements therefor. The fluid delivery set defines a fluid pathway from a supply container of the enteral or parenteral fluid to a connector element adapted to be connected to a device for introducing the fluid into the patient. Preferably the fluid delivery set has a tension responsive pinch valve to prevent bolus feeding in the event that the fluid delivery set becomes displaced from the pump housing.

22 Claims, 50 Drawing Sheets

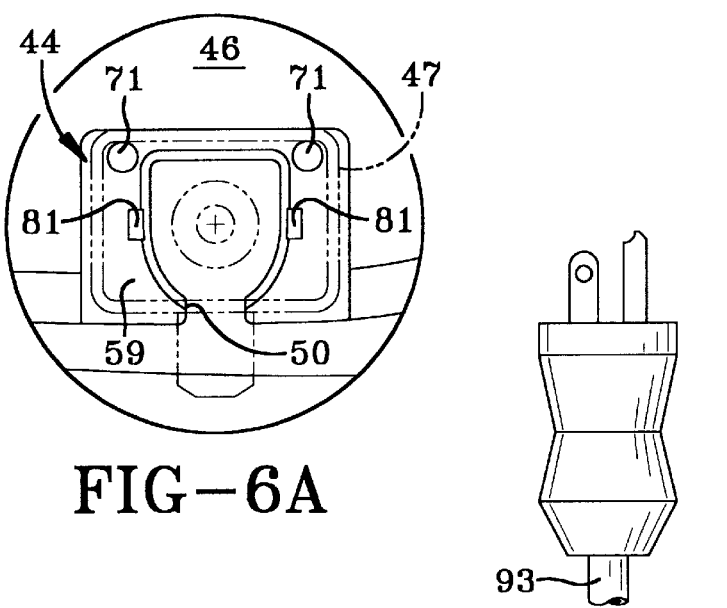
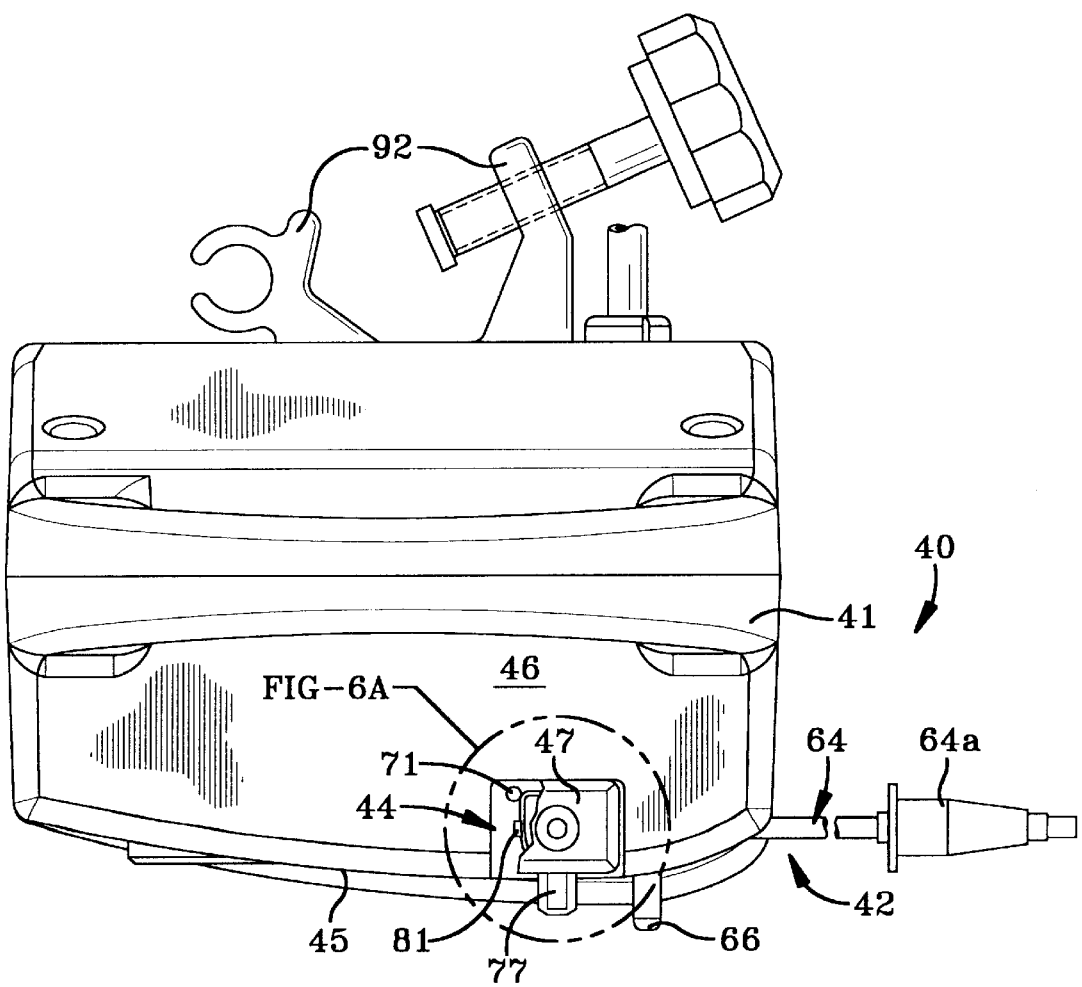
FIG-6A
FIG-6

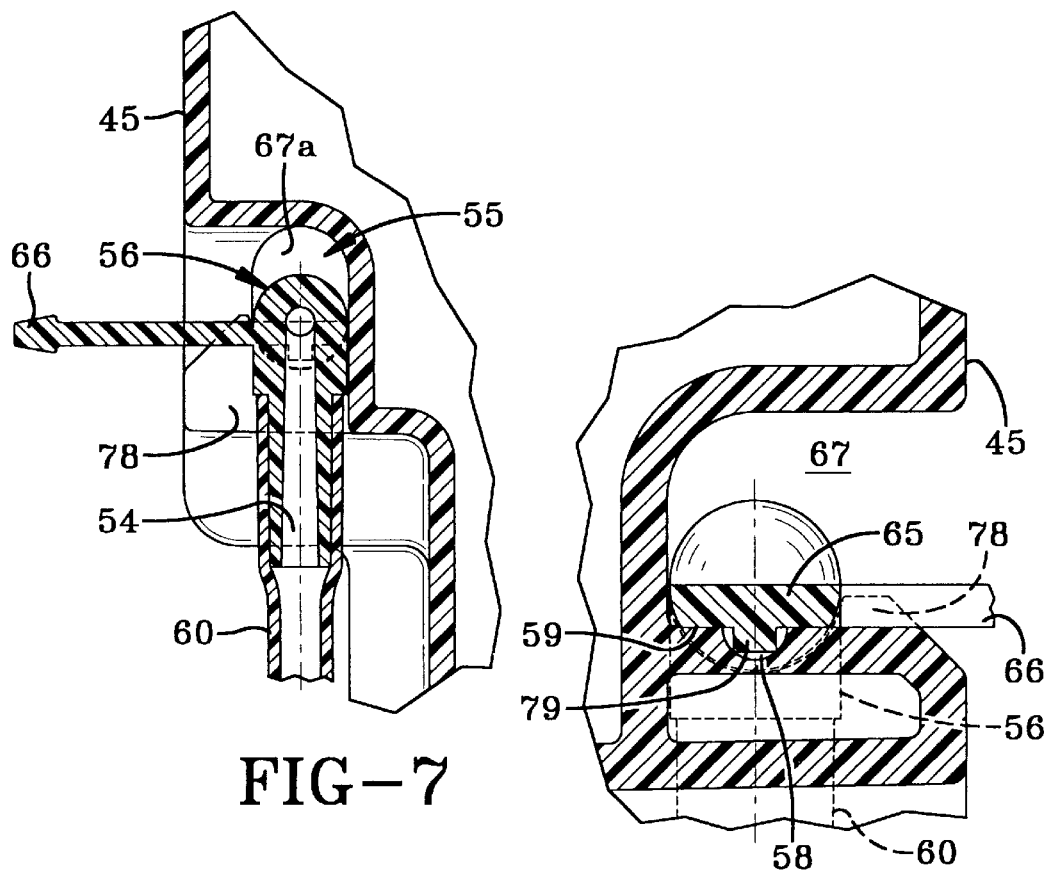
FIG-7
FIG-8A
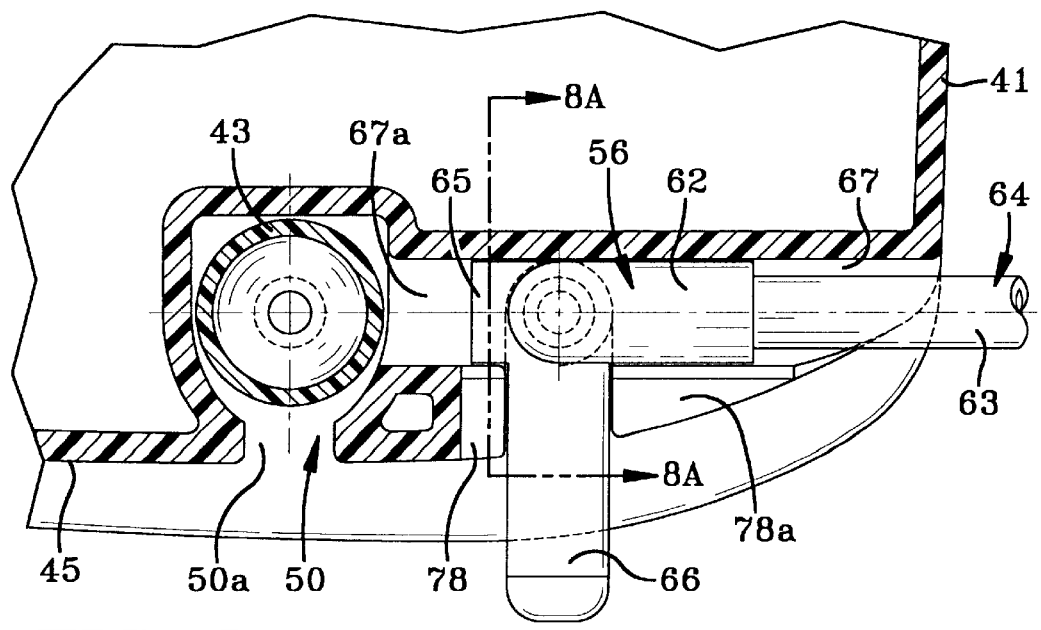
FIG-8

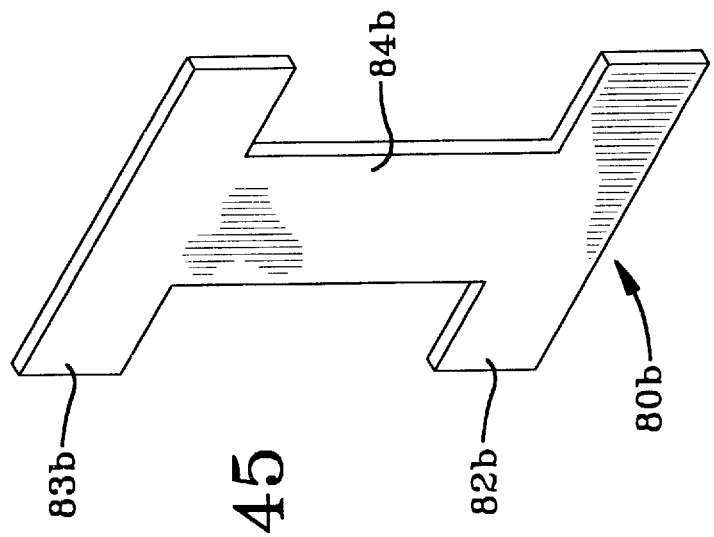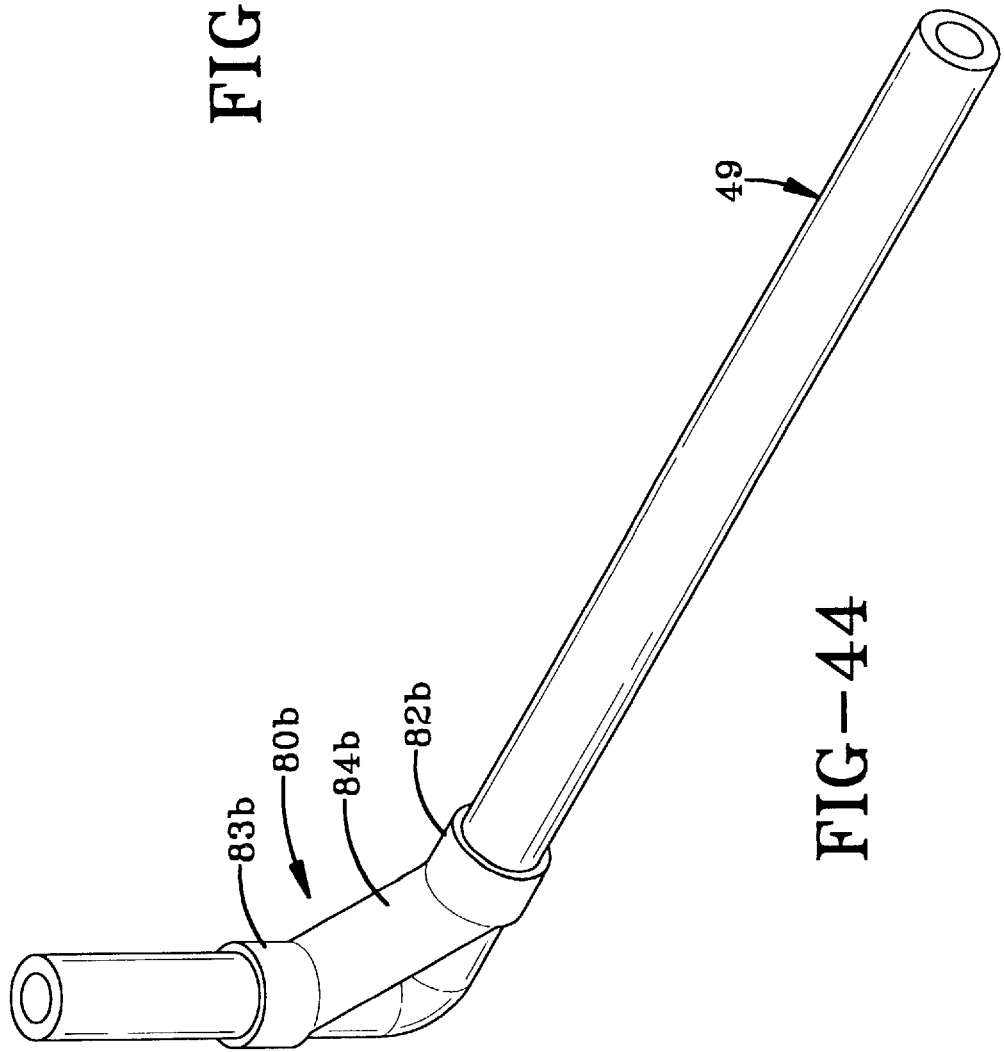

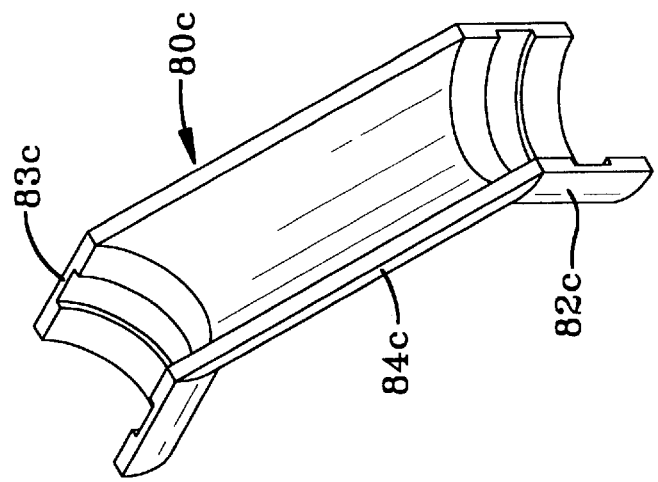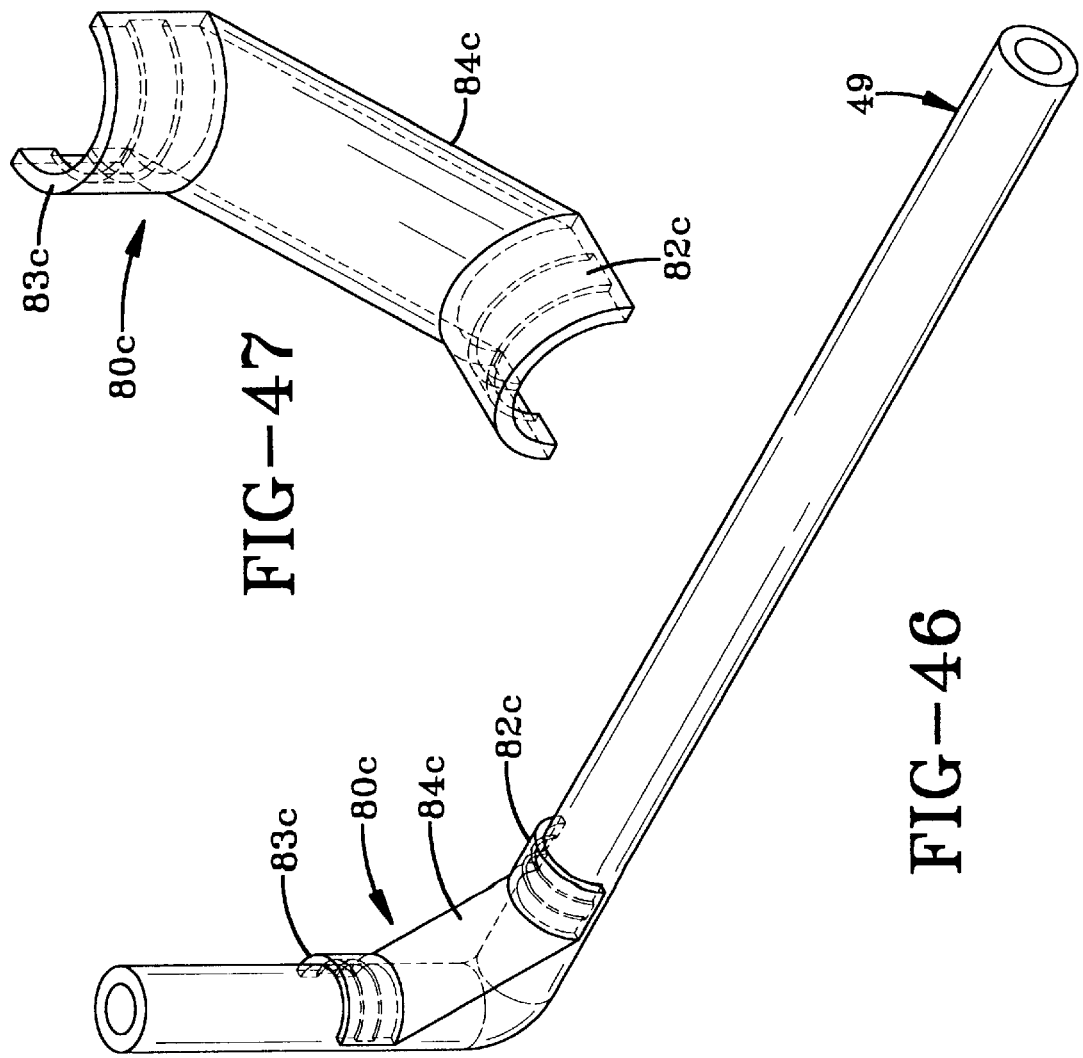

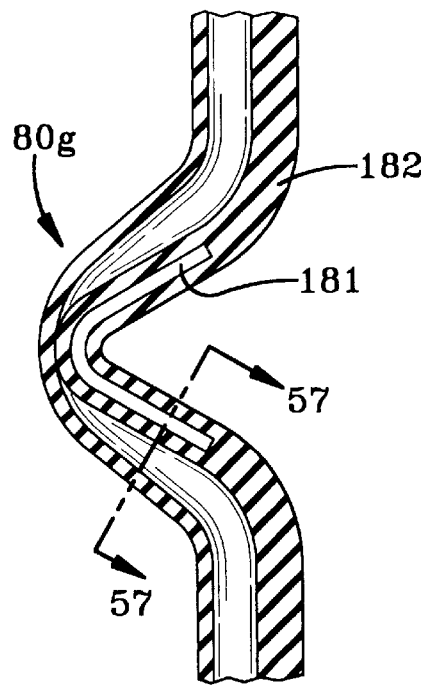
FIG-56
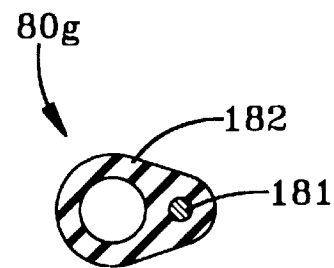
FIG-57
FIG-57A
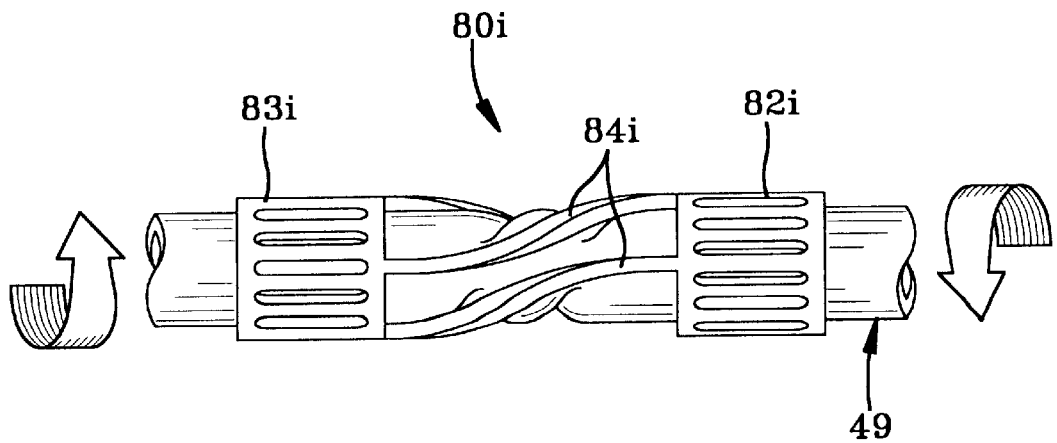
FIG-58

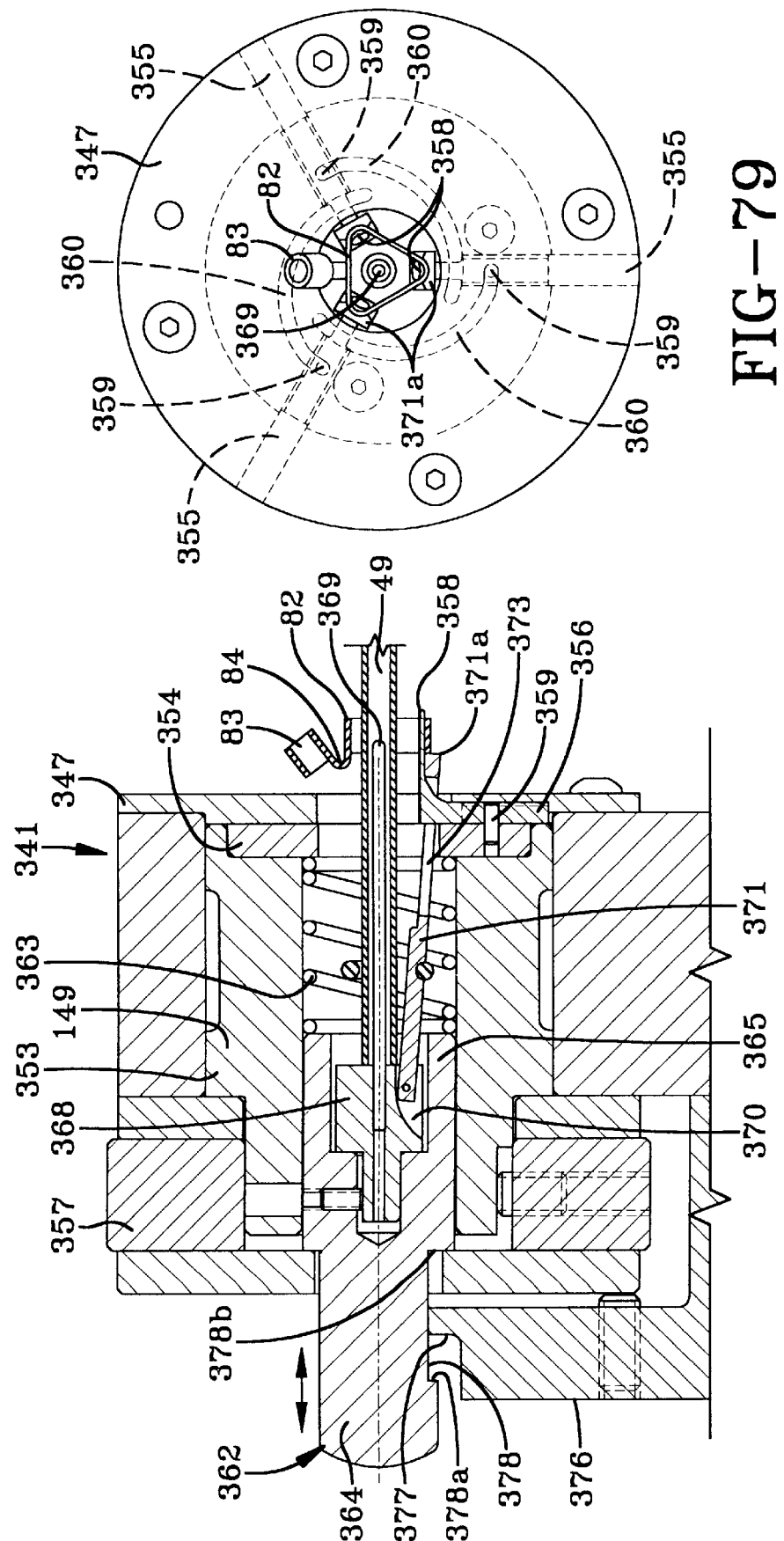

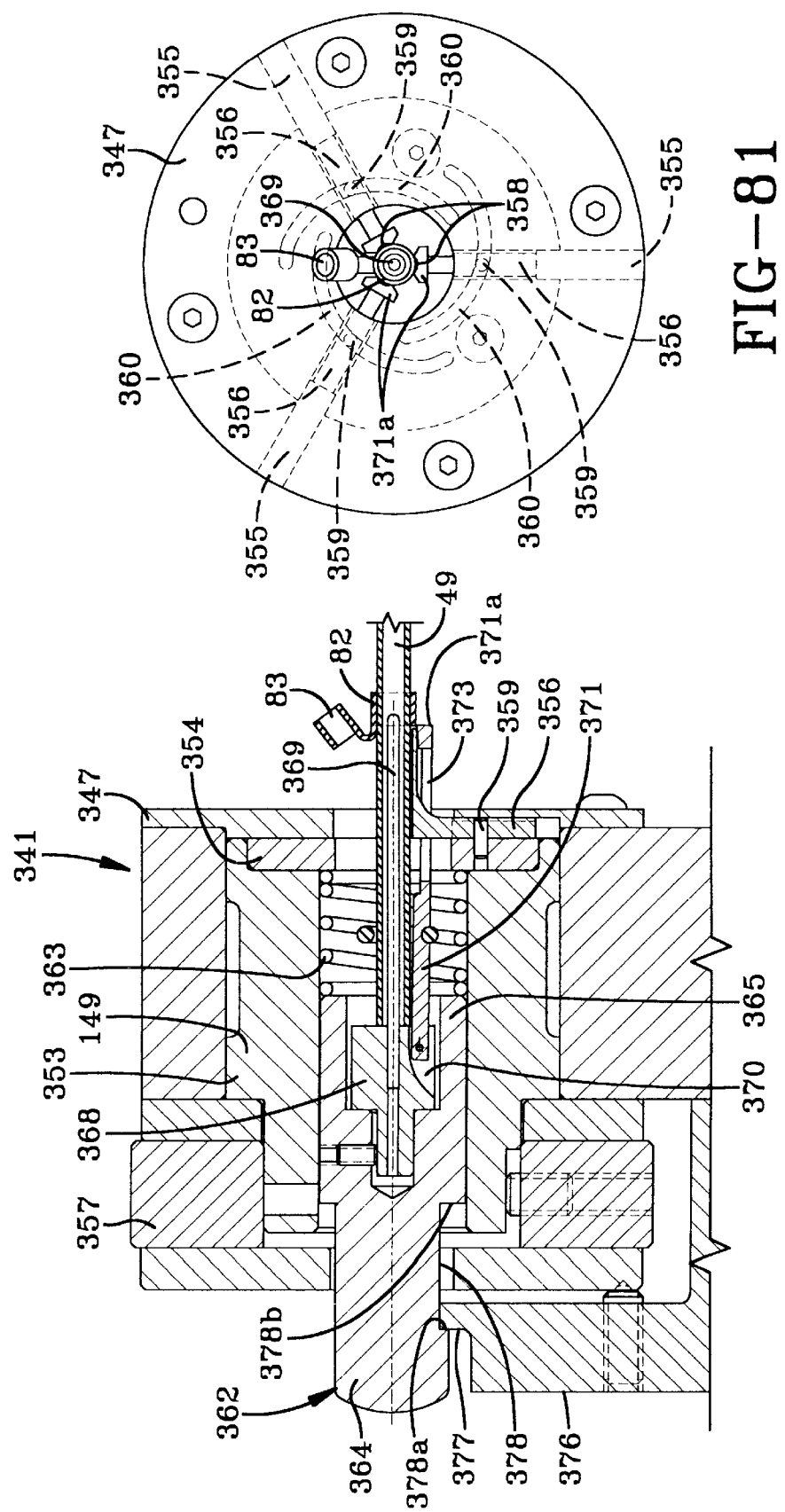

PERISTALTIC PUMP AND FLUID DELIVERY SET

FIELD OF THE INVENTION

The present invention relates to a combination of a peristaltic pump and a fluid delivery set, the latter commonly referred to as an administration set or a feeding set, for introducing an enteral fluid or a parenteral fluid into the body of a patient.

BACKGROUND OF THE INVENTION

The present invention is a combination of a rotary peristaltic pump and a fluid delivery set usable therewith that is adaptable for use on nearly any occasion wherein enteral or parenteral fluids are to be delivered to a patient through a flexible tubing. Parenteral fluids are delivered into the circulatory system of a patient. Enteral fluids are delivered into the gastrointestinal tract of the patient.

Rotary peristaltic pumps are well known and are described in a number of U.S. patents, such as, 5,250,027; 5,057,081; 4,913,703; 4,884,013; 4,832,584; 4,722,734; 4,720,636; 4,708,604; 4,690,673; 4,688,595; 4,545,783; and 4,513,796. Rotary peristaltic pumps commonly include a motor driven peristaltic rotor mounted on a shaft extending out through the front wall of the pump housing. The peristaltic rotor carries an array of two or more circumferentially, i.e., angularly, spaced rollers. The peristaltic rotor is designed to have a portion of the flexible tubing of the feeding set wrapped part way around the roller array under tension thereagainst or confined between the rollers and an opposing arcuate surface. As the motor within the pump housing rotates the shaft on which the peristaltic rotor is mounted, the spaced apart rollers are sequentially brought into contact with the flexible tubing with each revolution of the motor shaft and each roller in turn compresses a portion of the tubing to form an occlusion. The occlusion is advanced along the tubing as the peristaltic rotor turns and the roller advances along the tubing, the occlusion disappearing where the tubing diverges tangentially from the rotor. A predetermined amount of fluid is contained between successive occlusions so that a predetermined volume of fluid is advanced in a peristaltic manner through the tubing with each revolution of the rotor. Accordingly, the amount of fluid to be delivered to the patient may be regulated by controlling the rate of rotation of the peristaltic rotor and the time duration of the fluid delivery procedure.

Fluid delivery sets, also referred to herein as feeding sets, typically comprise a drip chamber having the outlet end connected to an elastically flexible tubing, such as a silicone rubber tube, or interconnected lengths thereof, that in turn connect, directly or through an adapter, to the requisite device, such as a needle or tube, for parenteral or enteral administration of fluid to the patient. The inlet of the drip chamber is adapted to receive, directly or through a connecting piece of flexible tubing, enteral or parenteral fluid from a supply container thereof, usually a hanging container. A portion of the flexible tubing is appropriately associated with a pump if the same is to be employed. For example, if the pump is a rotary peristaltic pump, the flexible tubing is usually wrapped partially, i.e., less than one complete turn, around the rotor as described above.

The fluid delivery set is typically changed every day. It is important that the fluid delivery set is manufactured according to fairly rigid manufacturing specifications so that delivery volumes are accurately predetermined and controlled and consistently produced from set to set. The portion of the flexible tubing, which together with the drip chamber makes up the fluid delivery set, i.e., feeding set, for mounting on the pump, for example, should be cut to a consistent length for each set and have a lumen of constant and consistent internal diameter and a consistent flexibility and elasticity as determined by durometer tests so that the internal diameter of the lumen will be consistent for each fluid delivery set when placed in tension around the rotor of the peristaltic pump. The drip chamber dimensions should also be consistent, especially in length, so that the drip chamber may be properly aligned with an adjacent drop sensor on the pump housing, if such a sensor is used.

The portion of each fluid delivery set that is typically assembled with a rotary peristaltic pump housing is placed into an operative position by inserting the drip chamber into a complementary retention recess or pocket formed in the housing, tangentially upward from a circumferential edge of the rotor. The flexible tubing which extends from the bottom of the drip chamber is stretched sufficiently around the roller array of the peristaltic rotor to provide for the peristaltic action of the rollers and back up along another channel or groove formed in the pump housing and leading tangentially upwardly from a circumferential edge of the rotor to supporting means such as a retention recess or pocket formed in the pump housing. Usually the flexible tubing will have formed thereon, or attached there around, a collar or flange that engages with an upper surface of the portion of the pump housing which defines the retention recess or pocket. The collar or flange is located along the flexible tubing at a linear position that will necessitate the flexible tubing being in tension in order to place the collar in the retention recess. In most known devices of the type generally described above, the flexible tubing more usually is positioned to extend out above the pump housing in a nearly vertical direction and arch over and away from the pump housing towards the patient being fed or treated, or, the flexible tubing is positioned in an arcuate groove formed in the pump housing leading upwardly as well as laterally away from the retention recess to the edge of the housing, from which point the flexible tubing arches on over and away from the pump housing towards the patient. The arcuate groove is of great enough radius, such as an inch, to not wrinkle or crimp the flexible tubing and reduce the cross-section of the lumen of the flexible tubing so as to significantly limit flow of liquid therethrough. Examples of the arrangement with the path of delivery of the fluid extending up above the pump housing are shown in U.S. Pat. Nos. 5,380,173; 5,250,027; 5,147,312; 5,133,650; 5,057,081; 4,913,703; 4,836,752; 4,832,584; 4,688,595; 4,552,516; 4,515,535; 4,513,796; and 4,231,725. An example of the arrangement with the delivery of the fluid through the tubing extending up from the peristaltic rotor and out laterally along an arcuate groove in the housing is shown in U.S. Pat. No. 4,884,013.

In still other arrangements the flexible tubing receiving fluid from the outlet of the drip chamber describes about a 180 degree arcuate bend mating the curvature of the peristaltic rotor and extends horizontally to and from the rotor about which it is to a large degree wrapped and held under tension by retaining means on the pump housing or by rotor compression as illustrated in U.S. Pat. Nos. 5,082,429; 4,886,431; 4,813,855; 4,722,734 and 4,545,783. In yet another arrangement the flexible tubing leading from the drip chamber or other supply means is brought upwardly from below the peristaltic rotor of the peristaltic pump and over the rotor and back downwardly to then extend laterally towards the patient. This configuration is illustrated in U.S.

Pat. Nos. 5,266,013; 5,110,270; 4,720,636; 4,708,604; 4,256,442; and 3,963,023.

With some of these designs or configurations it is possible for movement of a pole supporting a hanging container or other supply support, or indeed, movement of the supply container, per se, to cause the flexible tubing to become loosened or disengaged from the peristaltic rotor, or a restless patient may tug on and accidentally displace the flexible tubing from the retention recess or pocket on the downstream side of the peristaltic rotor, resulting in disengagement of the tubing from compression by the peristaltic rotor. In these situations, it is possible to have an uncontrolled rate of gravity-induced flow of the enteral or parenteral fluid to the patient because the rollers of the rotor are not properly compressing, i.e., occluding, the flexible tubing to restrict the flow of fluid through the feeding set to a pre-selected rate.

SUMMARY OF THE INVENTION

There is provided in accordance with the present invention an apparatus for supplying an enteral or parenteral fluid to a patient comprising a rotary peristaltic pump assembled with a fluid delivery set, the peristaltic pump having (a) a housing and (b) a peristaltic rotor projecting from the housing on a rotatable shaft, the housing having first and second receptacles for retaining and supporting the fluid delivery set, the fluid delivery set having (a) a drip chamber, (b) a plurality of flexible tubing portions, and (c) fluid connection elements therefor including the drip chamber and a retention/connector element, and the fluid delivery set as a whole defining a fluid pathway from a first end which is connectable to or integral with a supply container of the enteral or parenteral fluid to a second end which is connectable to or integral with a device for introducing the fluid into the patient, the fluid pathway extending substantially vertically downward through the drip chamber which is retained in the first receptacle in the pump housing, then downwardly around and against the peristaltic rotor and upwardly substantially vertically through the retention/connector element which is retained in the second receptacle in the pump housing, and horizontally from the second receptacle.

The special features of the pump housing and the fluid delivery set cooperatively inhibit unintended detachment of the fluid delivery set from the pump housing without sacrificing convenience in mounting and dismounting the fluid delivery set. Retentive mounting of the fluid delivery set helps assure regulated flow of the fluid to the patient.

Preferably the fluid delivery set is also provided with a tension responsive pinch valve associated with a portion of the flexible tubing, the pinch valve pinching the flexible tubing sufficiently to substantially prevent fluid flow therethrough when this portion of the flexible tubing is not under operative tension.

BRIEF DESCRIPTION OF THE DRAWINGS

FIG. 3A is a greatly enlarged view of the encircled portion of FIG. 3;

FIG. 4A is a fragmentary view in section taken along the line 4A—4A of FIG. 4;

FIG. 6 is a top view of the peristaltic pump and fluid delivery set assembly of FIG. 4, while within the encircled portion the cap-like or collar-like first retention element is partly broken away for purposes of illustration of the relationship of the retention element and one of the bosses on the floor of the first retentive recess;

FIG. 6A is an enlarged view of the encircled portion of FIG. 6 with the retention element shown only in dotted outline for purposes of illustration so that the nature of the floor of the first retentive recess and the connecting downwardly extending guideway will be better understood;

FIG. 7 is an enlarged fragmentary view in vertical section of the peristaltic pump and fluid delivery set assembly of FIG. 4 taken along the line 7—7 of FIG. 4;

FIG. 8 is a fragmentary view in horizontal section of the peristaltic pump and fluid delivery set assembly of FIG. 4 taken along the line 8—8 of FIG. 4;

FIG. 8A is a further enlarged fragmentary view in vertical section of the peristaltic pump and fluid delivery set assembly of FIG. 4 taken along the line 8A—8A of FIG. 8;

FIGS. 44 and 45 are perspective views similar to FIGS. 11 and 12, respectively, of an alternative pinch valve element assembled with a length of flexible tubing and of the pinch valve element by itself;

FIGS. 46 and 47 are perspective views similar to FIGS. 11 and 12, respectively, of an alternative pinch valve element assembled with a length of flexible tubing and of the pinch valve element by itself;

FIG. 47A is a rear view of the pinch valve element of FIG. 47;

FIGS. 56 and 57 are longitudinal and transverse cross-sectional views, respectively, of another form of tension responsive pinch valve in which a bent spring wire is embedded in the wall of a section of flexible tubing;

FIG. 57A is a transverse cross-sectional view of another form of tension responsive pinch valve similar in mode of action to that of the pinch valve of FIGS. 56 and 57, but in which the bent spring wire is bonded or adhesively attached longitudinally to the exterior of the wall of a section of flexible tubing;

FIG. 58 is a fragmentary side view of an assembly of yet another form of pinch valve element with a length of flexible tubing which assembly is a tension-responsive valve;

FIG. 78 is a fragmentary view in section of the assembly apparatus and stretched first tubular segment end portion of the pinch valve element shown in FIG. 77, and with the length of tubing inserted into the apparatus over the central guide rod and through the cluster of spreader fingers;

FIG. 79 is a front elevation of the portion of the assembly apparatus encompassed by the cover plate at the point of the assembly process illustrated in FIGS. 77 and 78;

FIG. 80 is a fragmentary view in section of the assembly apparatus with the tubular segment end portion of the pinch valve relaxed upon the length of tubing and with the ejector piston moved forward;

FIG. 81 is a front elevation of the portion of the assembly apparatus encompassed by the cover plate at the point of the assembly process illustrated in FIG. 80;

DETAILED DESCRIPTION OF THE INVENTION

As used herein and in the claims, descriptive terms such as top, bottom, upper, lower, above, below and the like are understood to refer to a fluid delivery set and a rotary peristaltic pump when they are assembled together in their intended operative manner and the shaft upon which the pump's perstaltic rotor is mounted is oriented in a substantially horizontal position.

Figure 1:
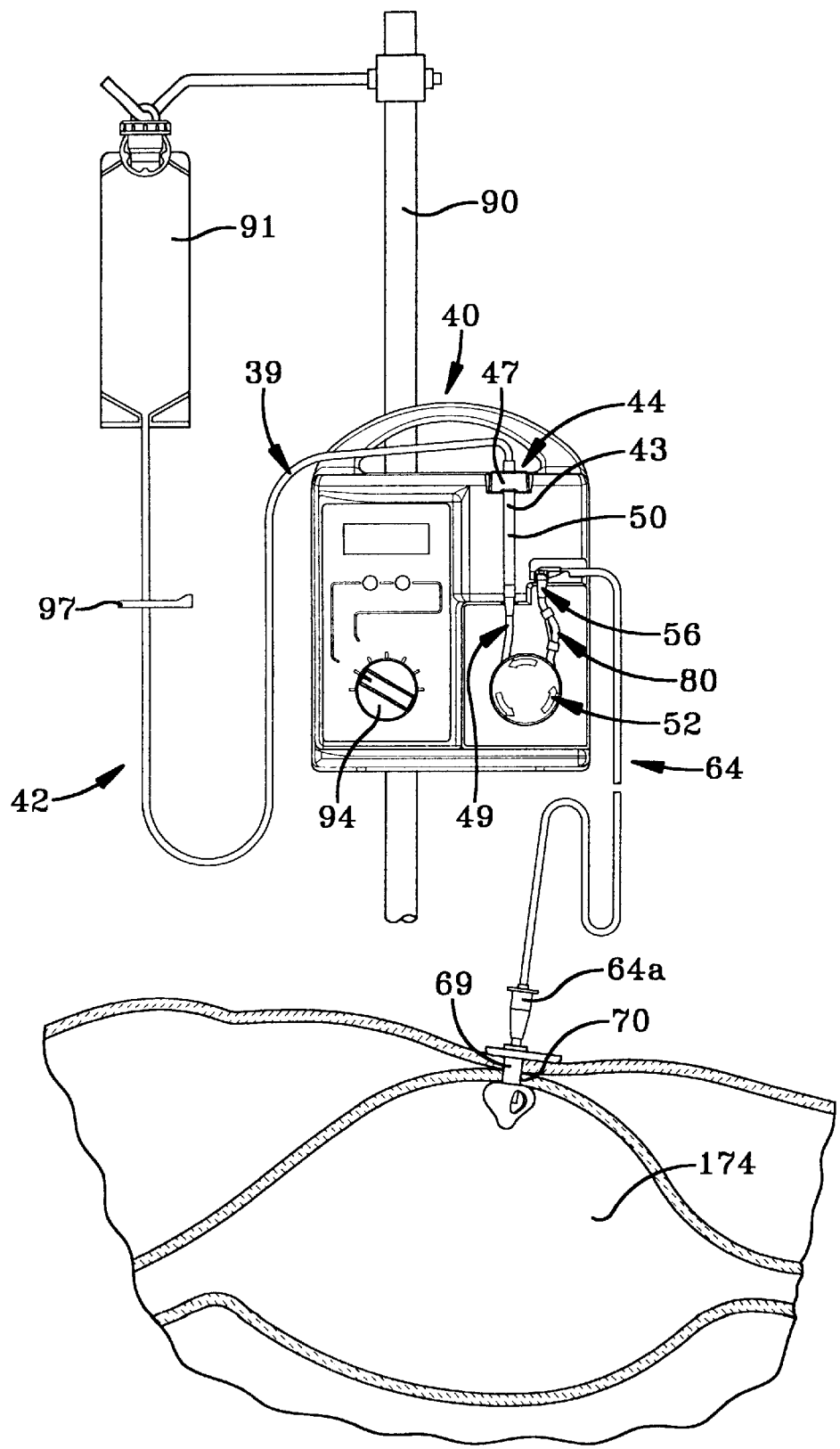
FIG. 1 is a view in front elevation of a peristaltic pump and fluid delivery set assembly according to the invention connected at the inlet end of the fluid delivery set to a supply container of liquid enteral nutritional product, here suspended from a support on a pole, and, connected at the discharge end of the fluid delivery set to a feeding tube extending into the stomach of a patient whose abdomen is shown in fragmentary view, partly broken away and in section.
Figure 2:
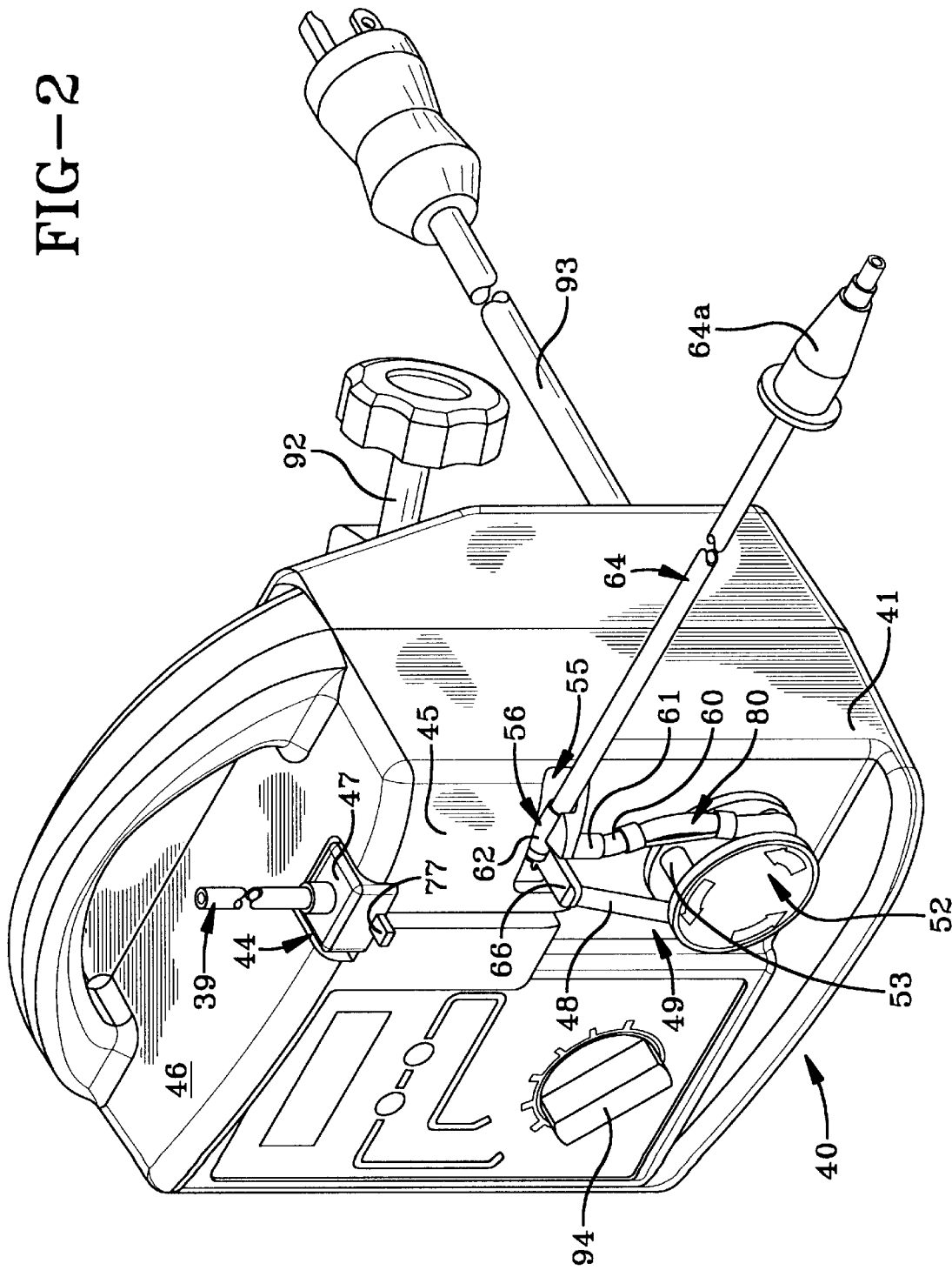
FIG. 2 is a perspective view of a peristaltic pump and fluid delivery set assembly according to the invention.

Referring now to the drawings in which like parts are referred to by like reference numerals, the co-acting apparatus assembly of the invention is seen in FIG. 1 to comprise a rotary peristaltic pump, indicated generally by the numeral 40, with a pump housing of novel configuration, and a fluid delivery set, indicated generally by the numeral 42, assembled with the rotary peristaltic pump.

The rotary peristaltic pump 40 is shown conveniently mounted on a conventional support pole 90, as is a supply container 91 of an enteral nutritional product. A suitable pole clamp 92 affixed to the back of pump housing 41 is best seen in top view in FIG. 6.

The assembly of the peristaltic pump and fluid delivery set is shown enlarged in FIGS. 2, 4, 4A, 5, 6, and 6A. The peristaltic pump is shown separately in FIGS. 3 and 3A. The fluid delivery set is shown separately in FIGS. 9–10, and 15–16.

Figure 17:
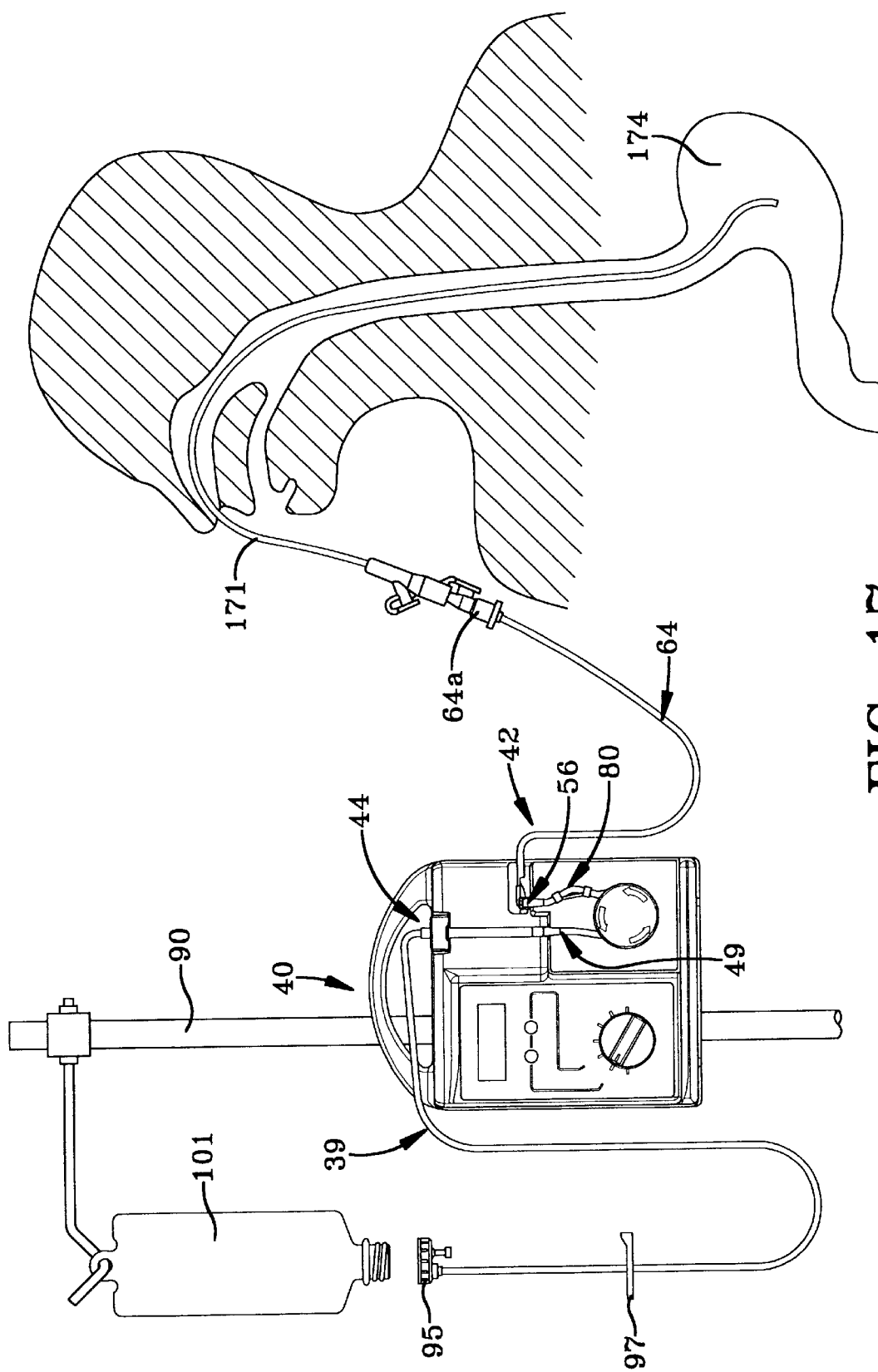
FIG. 17 is a view, partly in front elevation and partly fragmentary and in section, of the peristaltic pump-fluid delivery set assembly of the invention connectable at the inlet end to the screw cap opening of a hanging supply container of a liquid enteral nutritional product, and at the outlet end being connected to a nasogastric feeding tube extending into the stomach of a patient.
Figure 18:
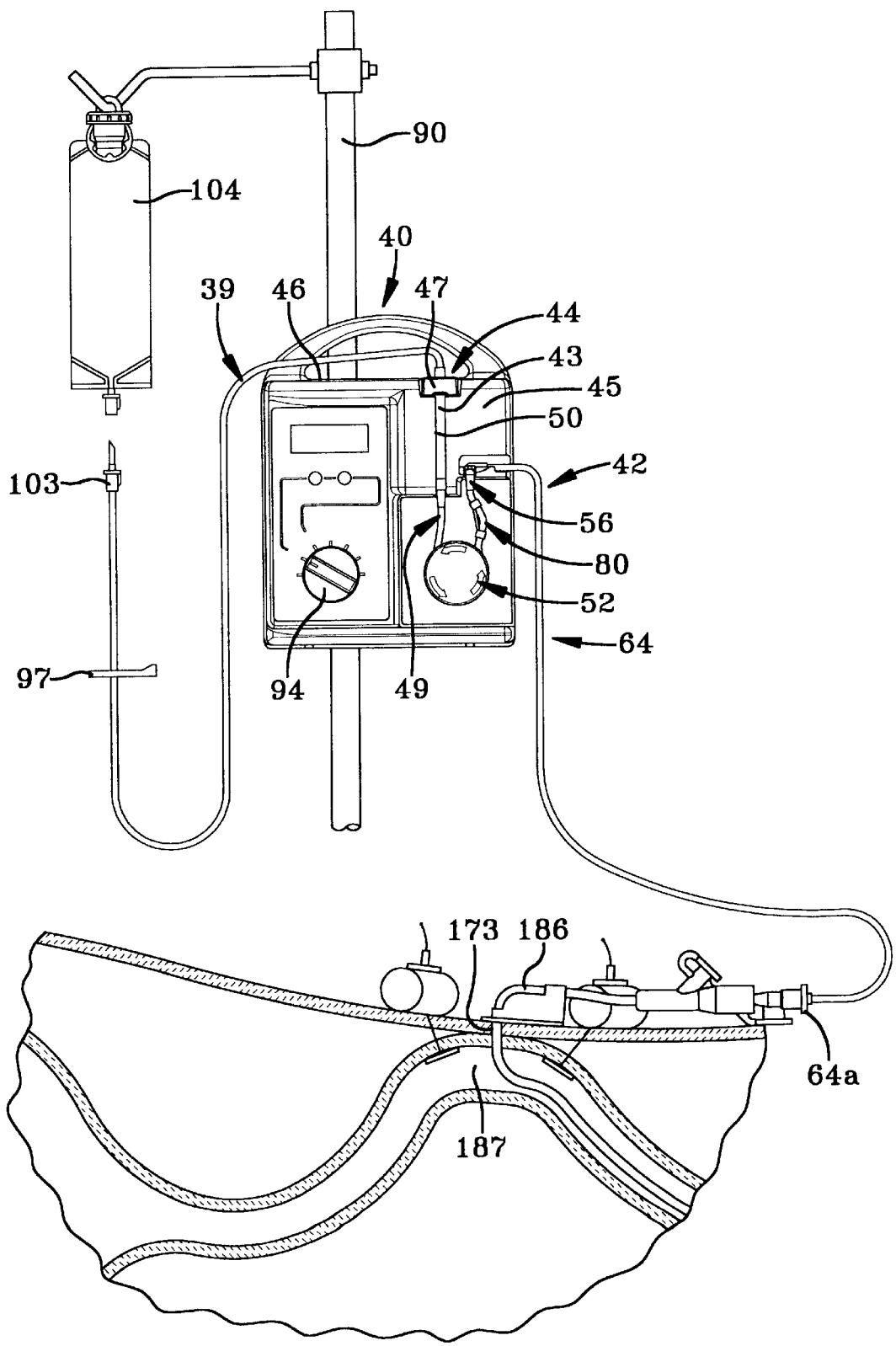
FIG. 18 is a view, partly in front elevation and partly fragmentary and in section, of the peristaltic pump-fluid delivery set assembly of the invention connectable at the inlet end to the pierceable cap of a hanging supply container of a liquid enteral nutritional product, and at the outlet end being connected to a feeding tube leading into the jejunum of a patient.
Figure 19:
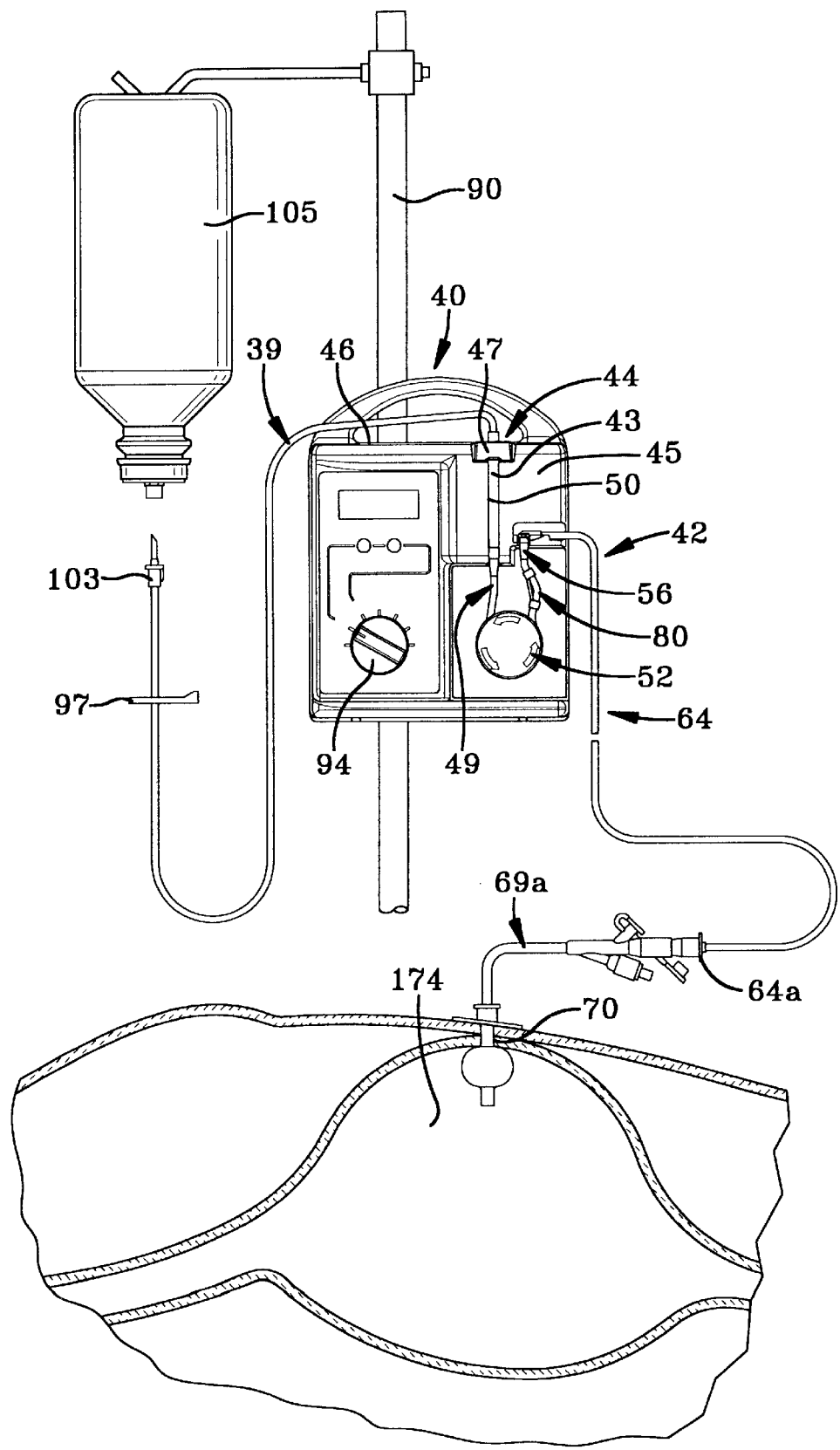
FIG. 19 is a view, partly in front elevation and partly fragmentary and in section, similar to FIG. 18 but with the outlet end of the fluid delivery set connected to a feeding tube extending through a stoma in the abdominal wall and into the stomach of the patient.

The fluid delivery set 42 provides a continuous fluid pathway from the supply container 91 of enteral or parenteral fluid to the tube or needle or other device directing the fluid into the body of the patient. While in this first embodiment a first end of the fluid delivery set is integral with a supply container, in alternative embodiments which are described herein a first end of the fluid delivery set is connectable to a supply container, and it is understood that either alternative may be employed in the practice of the invention described and claimed herein. For example, as shown in FIG. 17 a first end of the fluid delivery set may be connected to a supply container 101 using a threaded closure 95, or as shown in FIGS. 18 and 19 a first end of the fluid delivery set may be connected to a supply container 104, 105 by penetrating a membrane in the container or its closure with a spike or cannula 103.

Figure 4:
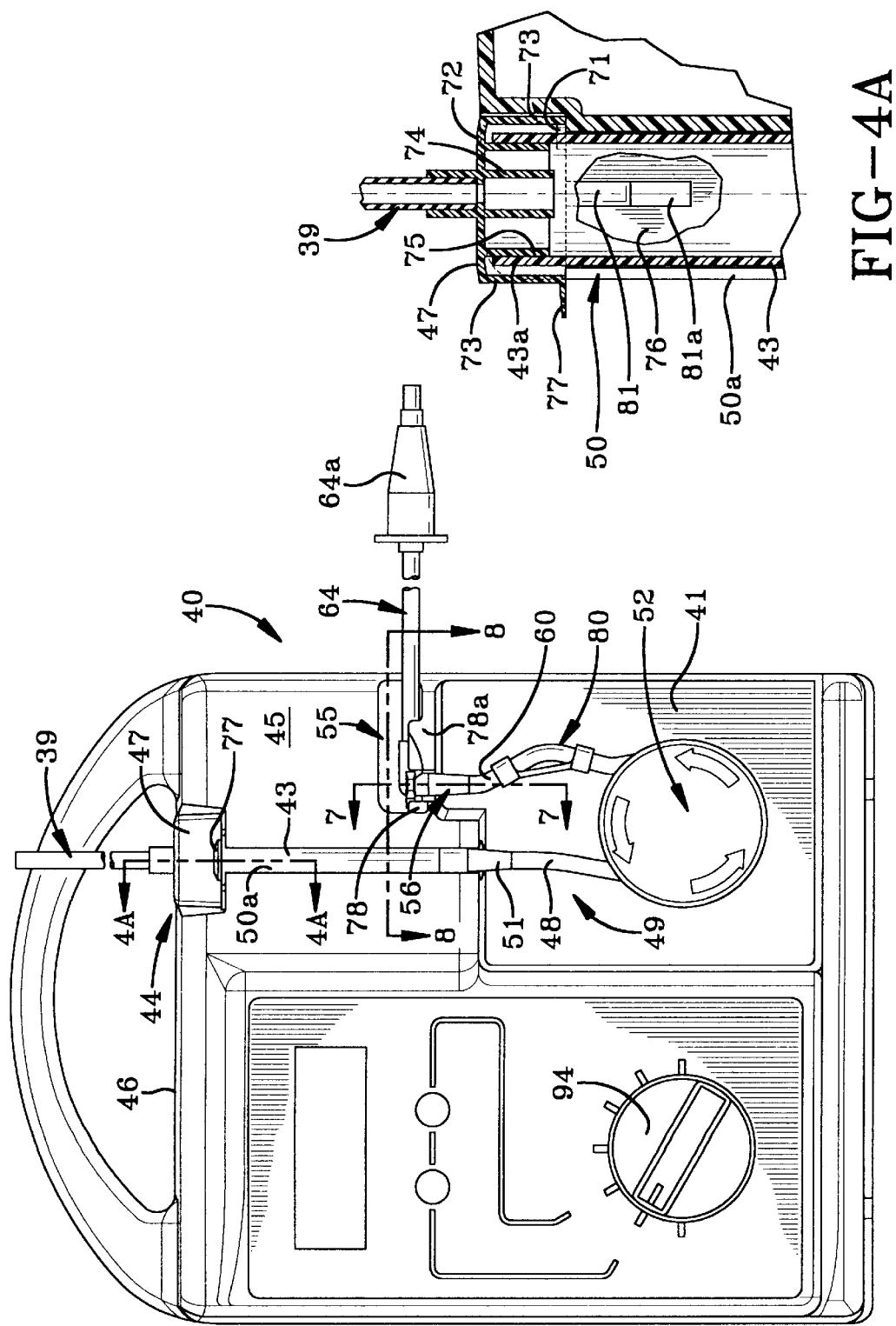
FIG. 4 is a view in front elevation of the peristaltic pump and fluid delivery set assembly of FIG. 2.

The fluid delivery set 42 is made up of a drip chamber 43 which is shown in FIGS. 1 and 4 partially hidden in a first retentive recess 44 formed in the juncture of the front wall 45 and top wall 46 of the pump housing 41. The drip chamber 43 is connected at the inlet thereof to a first length 39 of flexible tubing, shown foreshortened. Preferably, the first and third lengths of flexible tubing 39, 64 are made of polyvinyl chloride (PVC) and the second length of tubing 49 is made of an elastically flexible silicone rubber. The first length 39 of flexible tubing is connectable to or integral with the outlet of a supply container and may optionally have a second drip chamber (not shown) and/or a conventional slide clamp 97 assembled therewith. The outlet of the drip chamber 43 is connected to the first end 48 of a second length 49 of flexible tubing.

The drip chamber 43 is also provided with a collar-like or flange-like first retention element 47 press fit or adhesively attached thereto, preferably at the upper end 43a thereof as best seen in FIG. 4A. The first length 39 of flexible tubing is attached to the retention element 47 in a telescoping interference fit relationship. The first retention element 47, also referred to herein as a drip chamber retention element, shown here is rectangular and nearly square in outer shape and fits complementarily into the first retentive recess 44 of the pump housing. If desired, the drip chamber retention element 47 may be made with a different geometric shape, such as a triangular or oval or trapezoidal shape, so long as the retentive recess in the pump housing is shaped complementarily to receive and retain the drip chamber retention element.

The pump housing 41 is preferably molded from an impact resistant polymer or polymer blend such as an ABS (acrylate-butadiene-styrene) blend or ABS-polycarbonate blend. Extending from the bottom or floor 44a of the first retentive recess 44 of the pump housing is a substantially vertical guideway 50 formed in the front wall 45 of the pump housing. As may be seen in side view in FIG. 5, the upper part of the front wall 45 of the pump housing protrudes forwardly over the lower part, providing for vertical alignment of the drip chamber 43 and the second length 49 of flexible tubing depending therefrom with the pump's peristaltic rotor 52 positioned below the drip chamber 43. As seen in FIG. 4, the guideway 50 directs the drip chamber 43 downwardly from the first retentive recess 44 to the connection of the outlet 51 of the drip chamber 43 with the first end 48 of the second length 49 of flexible tubing.

Figure 3:
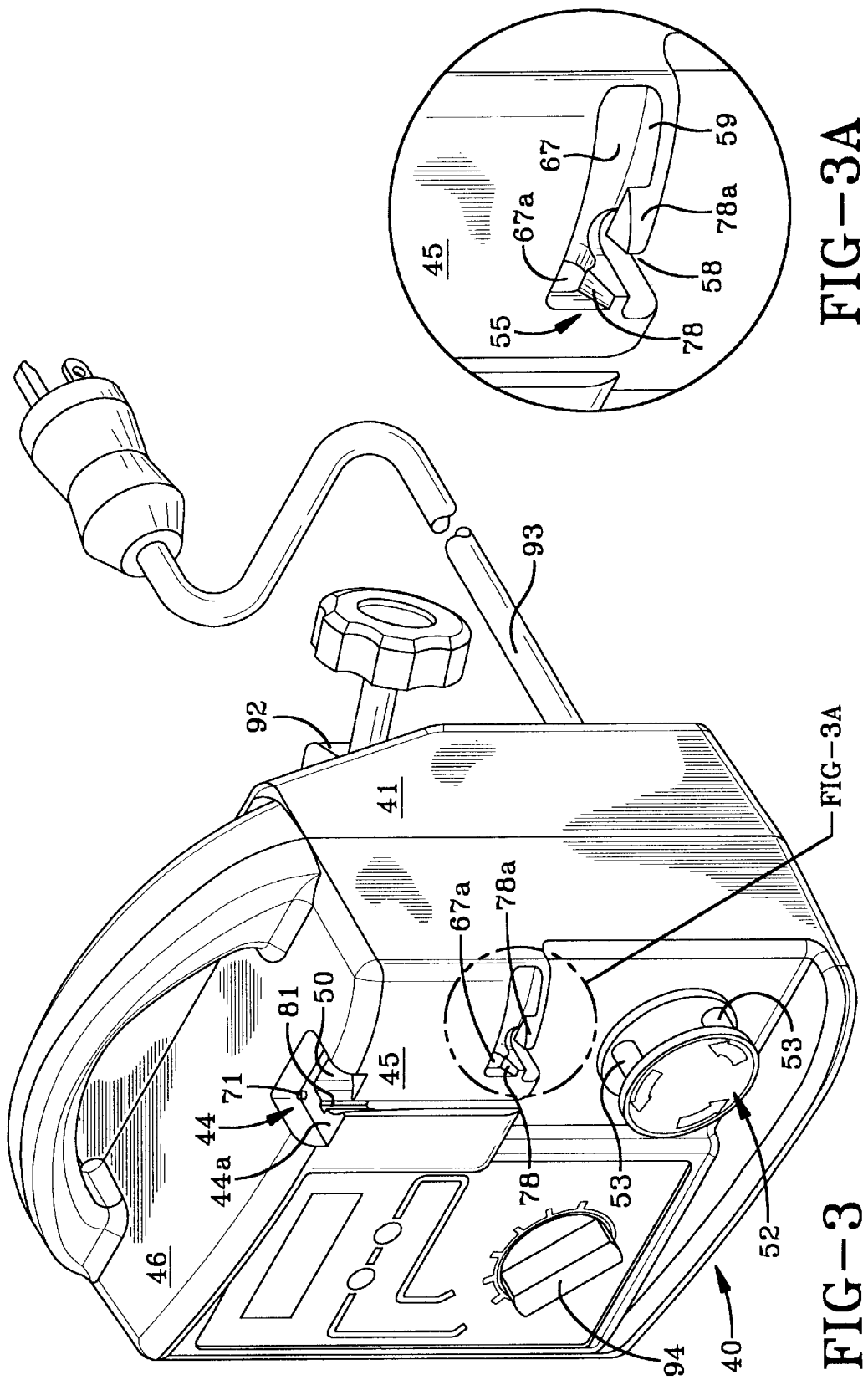
FIG. 3 is a perspective view of the peristaltic pump of FIG. 2, without the complementary fluid delivery set assembled therewith.
Figure 10A:
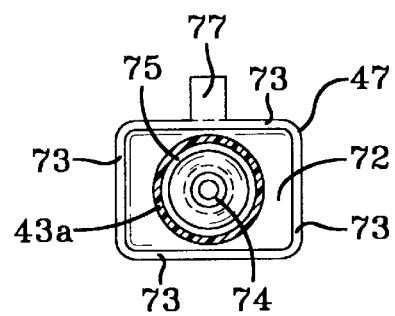
Fig. 10A is a view in section taken along the line 10A—10A of FIG. 10.

Referring to FIG. 3, a preferred form of configuration of the pump housing 41 of the peristaltic pump 40 is shown wherein the first retentive recess 44 is seen to have a substantially flat floor 44a surrounding the opening to the guideway 50. Two small upstanding bosses 71 extend upwardly at the left and right(not shown) back corners of the floor 44a. The first retention element 47 which supports the drip chamber is preferably made as an inverted hollow box that opens downwardly as may be seen in FIG.10A, a view in section taken along line 10A—10A of FIG. 10, looking up into the open side of the "box". When Fig. 10A is viewed in conjunction with FIG. 4A, which shows a cross-section of the first retention element 47, it is seen that this form of retention element has an upper rectangular wall 72 with depending sidewalls 73 that surround a short centrally located tubular inlet 74 that extends through the upper wall 72, providing for connection externally to the first length 39 of flexible tubing which is connectable to, or integral with, a supply container. Concentrically surrounding the tubular inlet 74 that extends slightly through the upper wall 72 and is surrounded by the sidewalls 73 is a foreshortened cylindrical sleeve portion 75 integrally formed with the upper wall 72. The cylindrical sleeve portion 75 serves as a support for the drip chamber 43, the upper end 43a of which, as indicated in FIG. 4A, is telescoped over the cylindrical sleeve portion 75 and press fit or adhered thereto.

It is further preferred that a small flange-like tab 77 be provided on the forward side of the sidewall 73 at the lower edge thereof. Such a flange-like tab is found to be readily grasped between the thumb and forefinger providing for convenient positioning or removal of the first retention element 47 and the attached drip chamber 43 and second length 49 of flexible tubing when mounting or removing the feeding set 42 from the pump housing 41.

Figure 5:
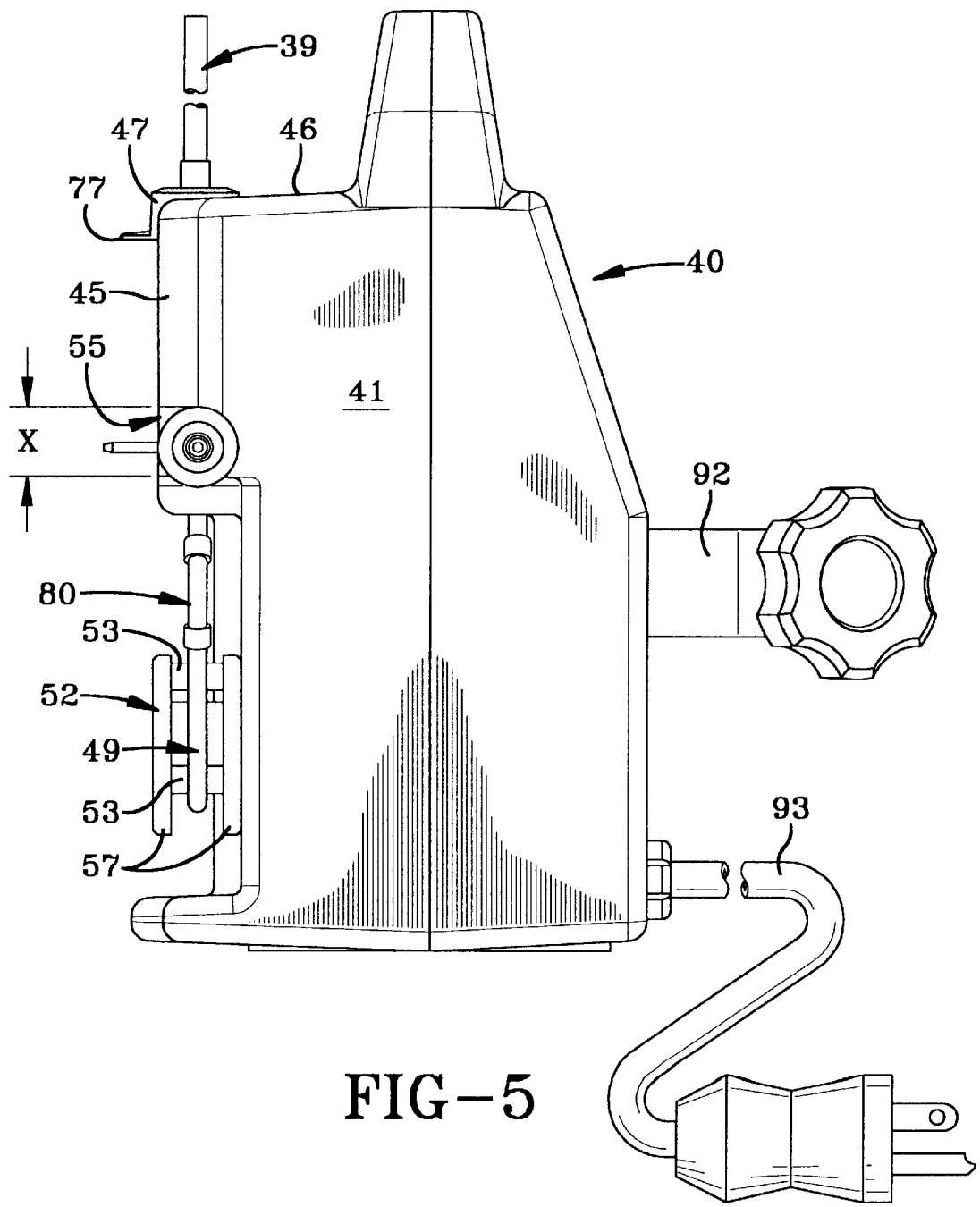
FIG. 5 is a side view of the peristaltic pump and fluid delivery set assembly of FIG.4.

The peristaltic pump rotor 52, as best seen in FIGS. 3 and 5, is conventional, having a plurality of rollers 53, for example, two to four, three being a practical number, that extend parallel to the axis of rotation of the rotor between opposing disc-like end face members 57 and are equiangularly disposed along a circumferential line about the axis of rotation of the rotor. Preferably the rollers 53 are each rotatable upon an axial rod or pin (not shown) which extends between the end face members 57. If desired, the rollers 53 may be fixed and not rotatable, but if fixed, will require more power to rotate the rotor against the second length 49 of flexible tubing held thereagainst under sufficient tension to provide peristaltic pumping action, and increased wear of the fixed rollers can be expected. The end face members 57 are supported axially on a shaft that is driven by a pump motor (neither the shaft nor the pump motor is shown), the pump motor being mounted within the pump housing 41 and the shaft extending forwardly through the front wall of the pump housing to support and rotate the peristaltic rotor 52. The pump motor is provided electrical power through a conventional electric appliance cord 93. A control knob 94 for selecting the fluid delivery rate is provided on the front of the pump housing.

Figure 9:
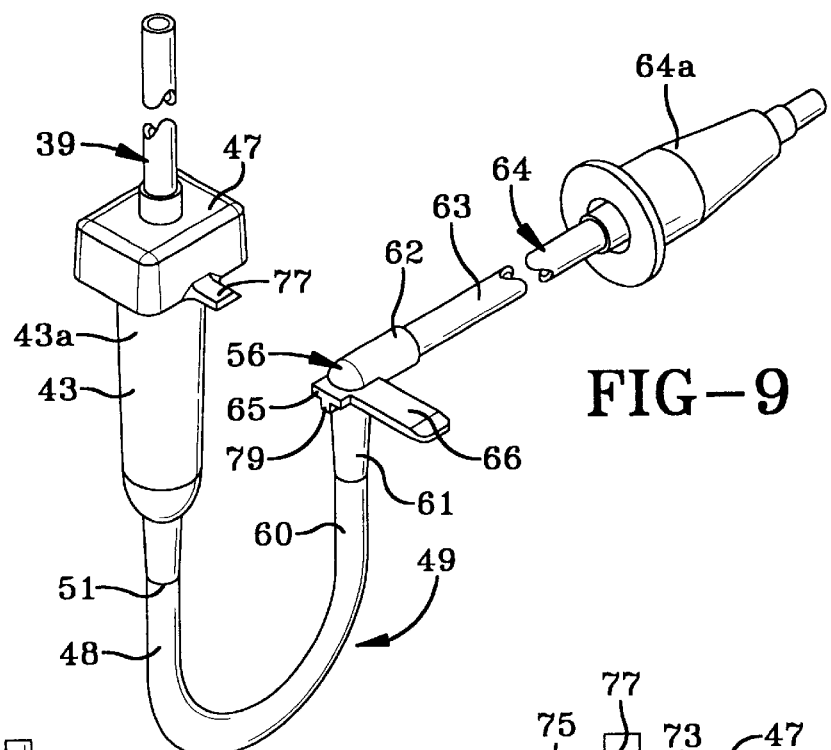
FIG. 9 is a perspective view of a fluid delivery set according to the invention with the first and third flexible tubing portions truncated and foreshortened.
Figure 10:
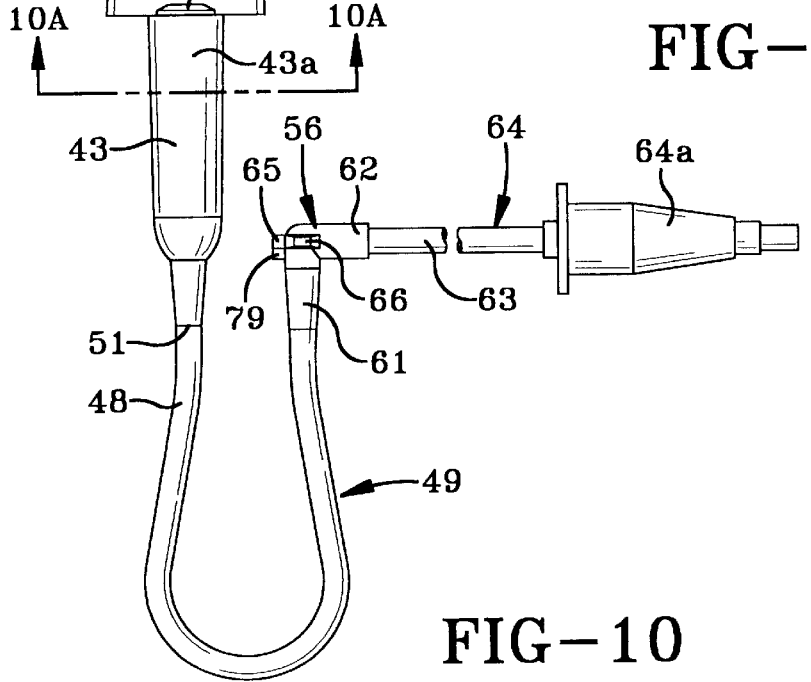
FIG. 10 is a front view of the fluid delivery set of FIG. 9.

Referring now to FIGS. 4, 9 and 10, the second length 49 of flexible tubing is wrapped down, around and against the peristaltic rotor 52 and is held under tension against the rollers 53 of the rotor 52 as the second length 49 of flexible tubing is brought back up the other side of the rotor to a connection of the second end 60 of the second length 49 of flexible tubing with a first leg 61 of a second retention element 56, referred to hereafter as a retention/connector element. The retention/connector element 56 is retained in the second retentive recess 55 of the pump housing when the peristaltic pump and fluid delivery set are assembled together. The second leg 62 of the retention/connector element 56 is connected to the first end 63 of a third length 64 of flexible tubing. The connection of the respective ends of the second length 49 of flexible tubing to the retention/connector element 56 and to the outlet of the drip chamber 43 is made by placing the tubing ends on the one hand, and the retention/connector or drip chamber outlet on the other hand, in a male/female, or telescoping, relationship, or interference fit, and if desired, using adhesives, welding, etc., to secure the joint so-made.

The retention/connector element 56, is retentively but replaceably held in the second retentive recess, or receptacle, 55 which is formed in the protruding upper part of the front wall 45 of the pump housing 41 and is substantially vertically aligned with the side of the peristaltic rotor 52 opposite the side aligned with the drip chamber 43. As best seen in FIG. 3A, a notch or slot 58 extending through the floor 59 of the retentive recess 55 and opening to the front of the housing wall 45 admits the vertical first leg 61 of the retention/connector element 56.

In a preferred form shown in greater detail in FIGS. 23–28, the retention/connector element 56 is preferably molded into a substantially hollow tubular form and the continuous fluid pathway 54 as it extends therethrough forms about a right angle bend, whereby the retention/connector element 56 has first and second legs 61 and 62, that are joined at about a right angle. The fluid pathway 54 through the retention/connector element 56 has preferably about the same cross-sectional area throughout as the lumen of the lengths of flexible tubing connected thereto so that there is substantially no constriction of fluid flow around the right angle bend. The bend in the preferred retention/connector element has a radius, at the location indicated by "R" in FIG. 25, of less than about 0.9525 cm. (0.375 inch), preferably less than about 0.635 cm. (0.25 inch) in order to fit retentively into the recess 55. Comparative testing has indicated that the retention/connector element of the fluid delivery set disclosed herein is more securely attached to the rotary peristaltic pump disclosed herein than the analagous prior art retention device/perstaltic pump of the prior art shown in FIGS. 21 and 22.

Figure 27:
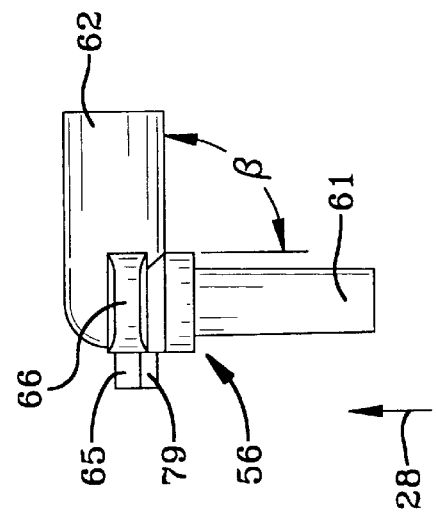
FIG. 27 is a front view of the retention/connector element of FIG. 23.
Figure 28:
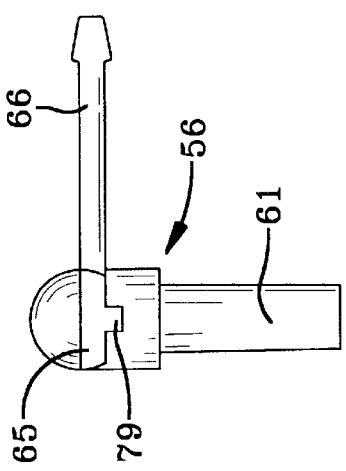
FIG. 28 is a bottom view of the retention/connector element of FIG. 23 looking in the direction indicated by the arrow 28 in FIG. 27.
Figure 31:
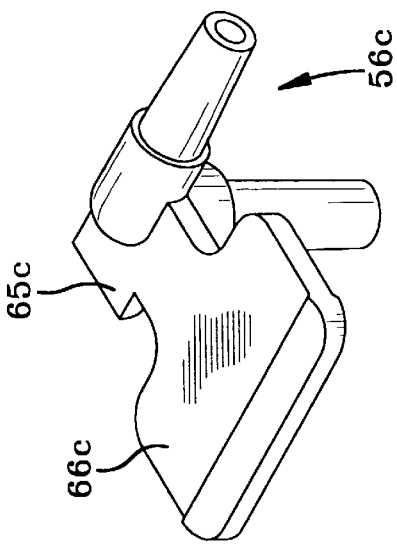
FIGS. 29 to 34 show alternative embodiments of right angle retention/connector elements with various forms of tabs for grasping, except for the retention-connector element of FIG. 29 which has only a retention tab.
Figure 34:
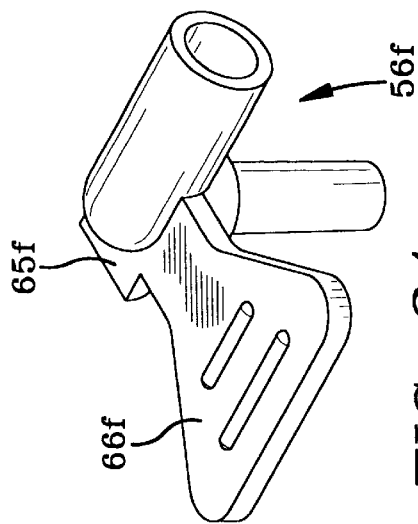
Figure 30:
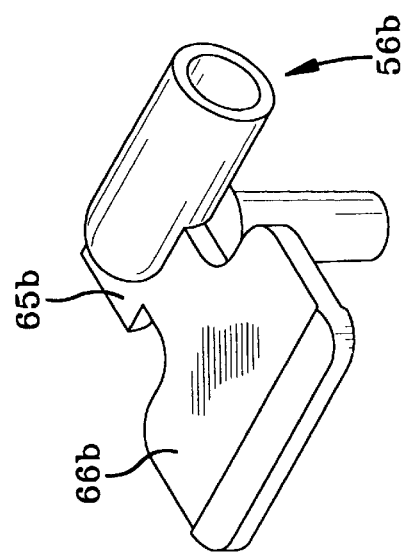
Figure 33:
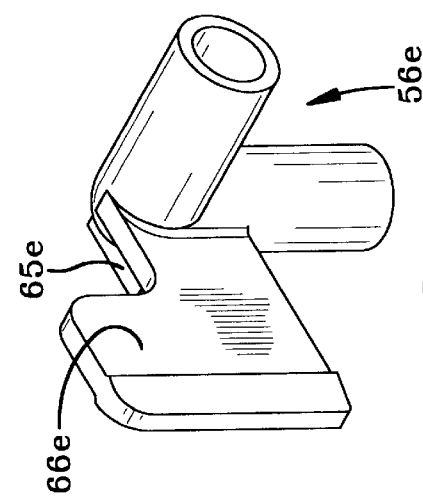

In order to have good retention of the retention/connector element 56 in the second retentive recess or receptacle 55 so that accidental total or partial removal of the fluid delivery set 42 from the pump housing 41 is difficult and thus unlikely, with the retentive recess 55 having an opening with a vertical height, as represented by dimension "X" in FIG. 5, of about 1.12 cm.(0.44 inch), the angle of the bend, as represented by the angle "β" in FIG. 27, in the retention/connector element 56 may vary from a right angle by not more than about plus or minus 11.8 degrees, or at a maximum of about 12 degrees variation. Thus, the angle "β" of the bend may vary from about 78 to about 102 degrees, but is preferably between about 85 to about 95 degrees for ease in insertion and removal of the retention/connector element 56 and also for good interlocking thereof with the retentive recess 55. Comparative testing has indicated that the retention/connector element 56 of the fluid delivery set disclosed herein is more securely attached to the rotary peristaltic pump disclosed herein, than the analogous prior art retention device rotary peristaltic pump of the prior art shown in FIGS. 21 and 22.

A highly preferred feature of the retention/connector element 56 is a foreshortened retention tab 65 that extends laterally from the retention/connector element 56 at about the level of the right angle bend and in a direction opposed to the second, i.e., horizontal, leg 62. As best seen in FIGS. 8 and 8A, the retention tab 65 serves to help retain the retention/connector element 56 in the second retentive recess 55 of the pump housing and also helps support the retention/connector element 56 on the floor 59 of the second retentive recess and prevent it slipping down through the notch or slot 58 in the floor 59. Preferably, the retention/connector element 56 is also provided with a forwardly extending handle or tab 66 for grasping that is conveniently grasped between the thumb and forefinger when inserting the retention/connector element 56 into, or removing it from, the second retentive recess 55. The handle or tab 66 for grasping is also located at about the level of the right angle bend in retention/connector element 56 and extends at about a right angle to each of the first and second legs 61,62 and to the retention tab 65.

In FIGS. 23 to 28 retention/connector element 56 is shown with the first leg 61 having a smaller outer diameter over which the second end 60 of the second length 49 of flexible tubing is to be telescoped in connecting the two, as shown in FIGS. 9, 10, 15 and 16, and the second leg 62 is shown with a larger inner diameter into which the first end 63 of the third length 64 of flexible tubing would be telescoped in making the connection therebetween. This is merely a matter of choice and either connection may be made with the flexible tubing being the inner or outer member of the connection.

Figure 29:
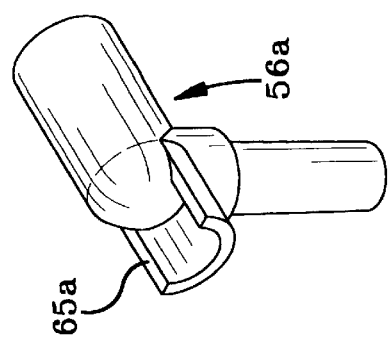
Figure 32:
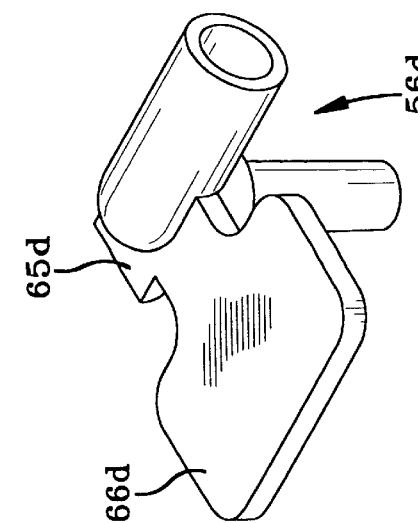
Figure 35:
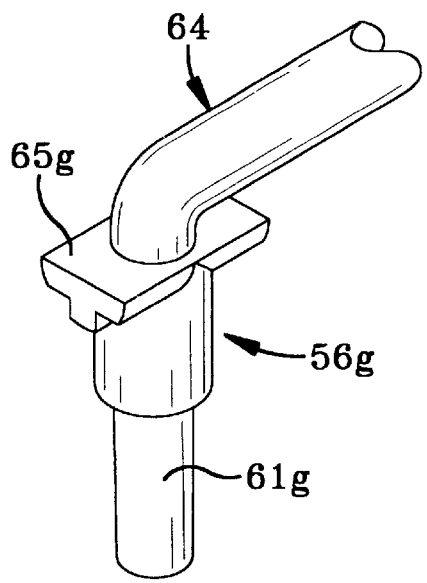
FIGS. 35 to 38 are perspective views of more alternative embodiments of retention/connector elements with various shaped retention tabs and not having a right angle formed in the channel within the retention/connector element.
Figure 36:
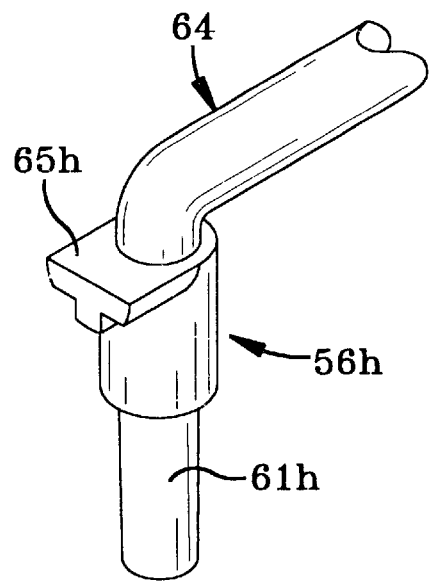
Figure 37:
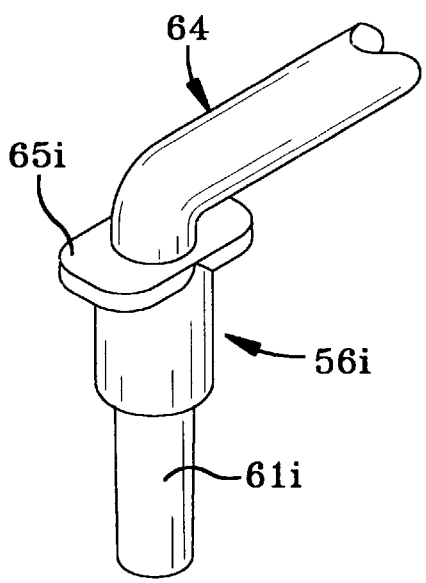
Figure 38:
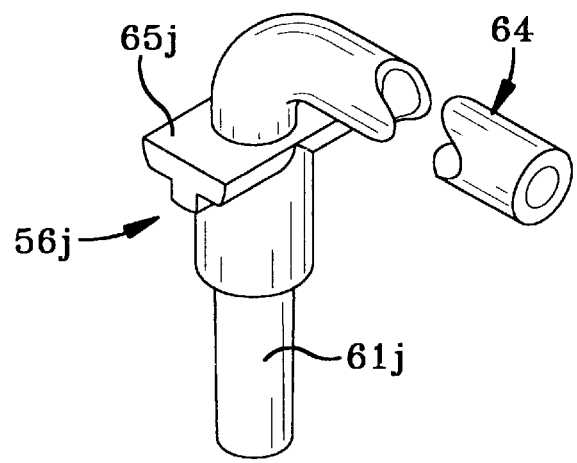

Alternative embodiments 56a–56f of retention/connector elements which may be used in the practice of the present invention and that incorporate a right angle bend within the retention/connector element are shown in FIGS. 29 to 34 with various shapes and sizes and orientations of the tabs 66b–66f for grasping the retention/connector element corresponding to tab 66, or absence thereof as shown in embodiment 56a in FIG. 29, and with a variation in the shape of the retention tab 65a in FIG. 29 corresponding to retention tab 65. It is understod that the retention tab may take a wide variety of shapes so long as there is provided a complementary cavity in the pump housing with retention characteristics that facilitate ready insertion and removal of the retention/connector element.

Retention/connector elements that have only one leg but have various shaped retention tabs are depicted in FIGS. 35–38. The approximate right angle bend in the fluid pathway needed to fit into the second retentive recess 55 and horizontal guideway 67 of the pump housing 41 is made in the third length 64 of flexible tubing which is bent immediately adjacent the connection thereof to the retention/connector element 56g–56j. Such bends in the third length 64 of flexible tubing are shown in FIGS. 35–38. The flexible tubing must be of material that does not unduly restrict fluid flow from a peristaltic pump when bent at about a right angle over a radius of less than about 1.25 cm and preferably not when bent over a radius of about 0.9525 cm (0.375 inch). However, it is understood that a retention/connector element used for connecting the second and third lengths of flexible tubing must have a retention tab 65g–65, extending substantially normal to the vertical leg 61g–61, to complementarily engage a retentive recess 55 in the pump housing 41. Most preferably the retention tab has a flange 79 extending substantially normally therefrom to mate with a retentive recess in the pump housing.

Figure 20:
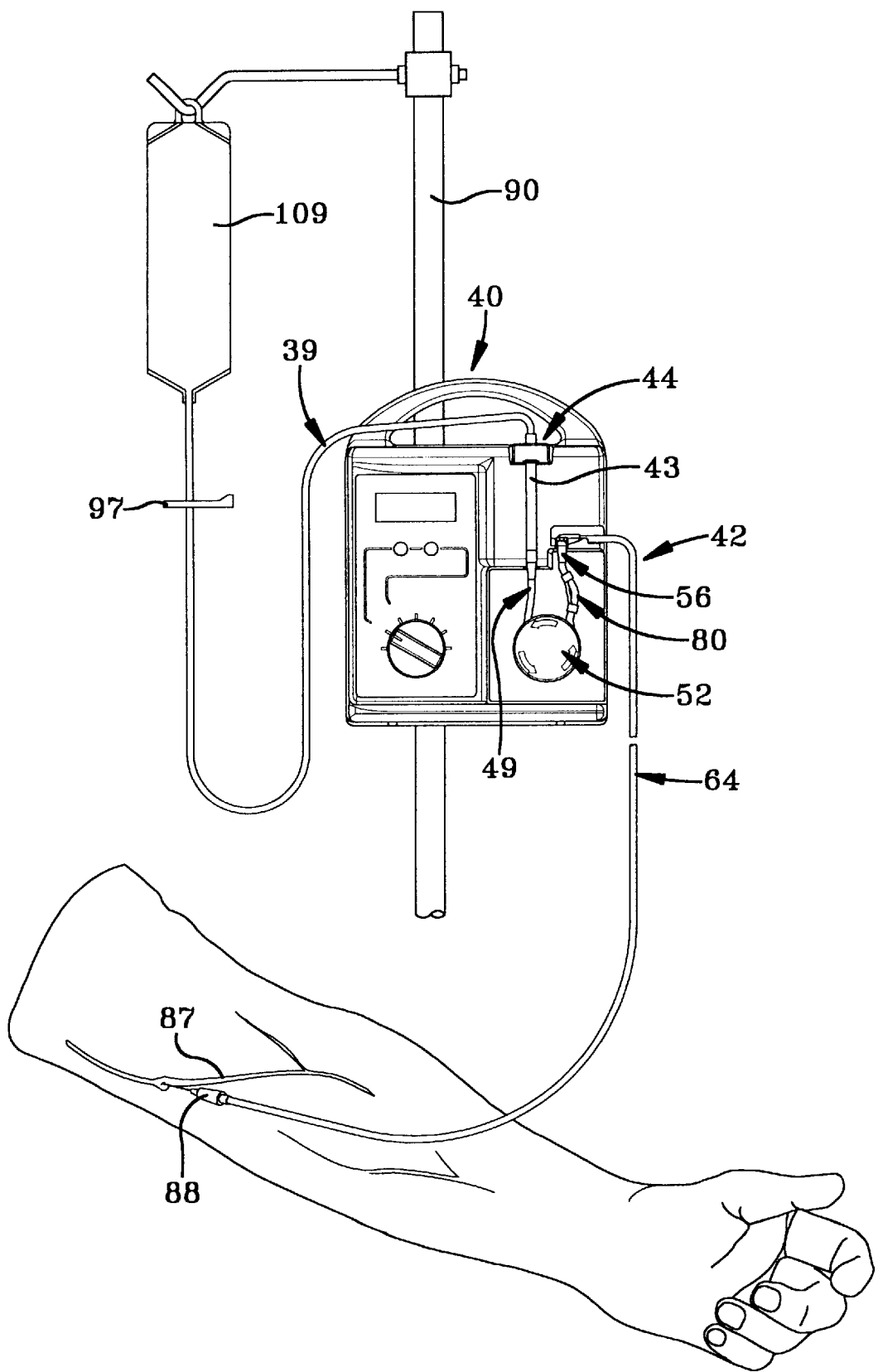
FIG. 20 is a view, partly in front elevation and partly fragmentary, of a peristaltic pump-fluid delivery set assembly of the invention with the inlet end of the first length of flexible tubing connected to a hanging supply container of a parenteral fluid and the outlet of the third length of flexible tubing connected to a needle extending into a vein in the arm of a patient.

When the fluid delivery set is assembled with the peristaltic pump, the third length 64 of flexible tubing extends from the connection of the first end 63 thereof with the second leg 62 of retention/connector element 56 along horizontal guideway 67 formed in the front wall 45 of the pump housing 41. As best seen in FIG. 3A, the guideway 67 is connected to and leads from the second retentive recess 55 to a lateral side of the front wall 45 of the pump housing 41, here the closest lateral side. In a preferred embodiment, the third length 64 of flexible tubing extends horizontally from the retention/connector element to a lateral side of the front wall of the pump housing and thereafter extends to an adapter or connector 64a for connecting the second end of the third length of flexible tubing to a device, such as a feeding tube or needle, leading into the body of a patient. Some examples of such devices are, in enteral administration: a feeding tube 69 seen in FIG. 1, and feeding tube 69a seen in FIG. 19, each extending through a gastrostomy 70 into the stomach 174; a nasogastric tube 171 leading down the esophagus into the stomach 174 as seen in FIG. 17; a jejunal feeding tube 186 extending through a jejunostomy 173 to the jejunum 187 as seen in FIG. 18; or, in parenteral administration: a needle or other tubular inlet 88 leading into the vein 87 of a patient as seen in FIG. 20. As already stated above, it is also understood that the third length of tubing may be integral with a device suitable for insertion into the body of a patient.

Figure 21:
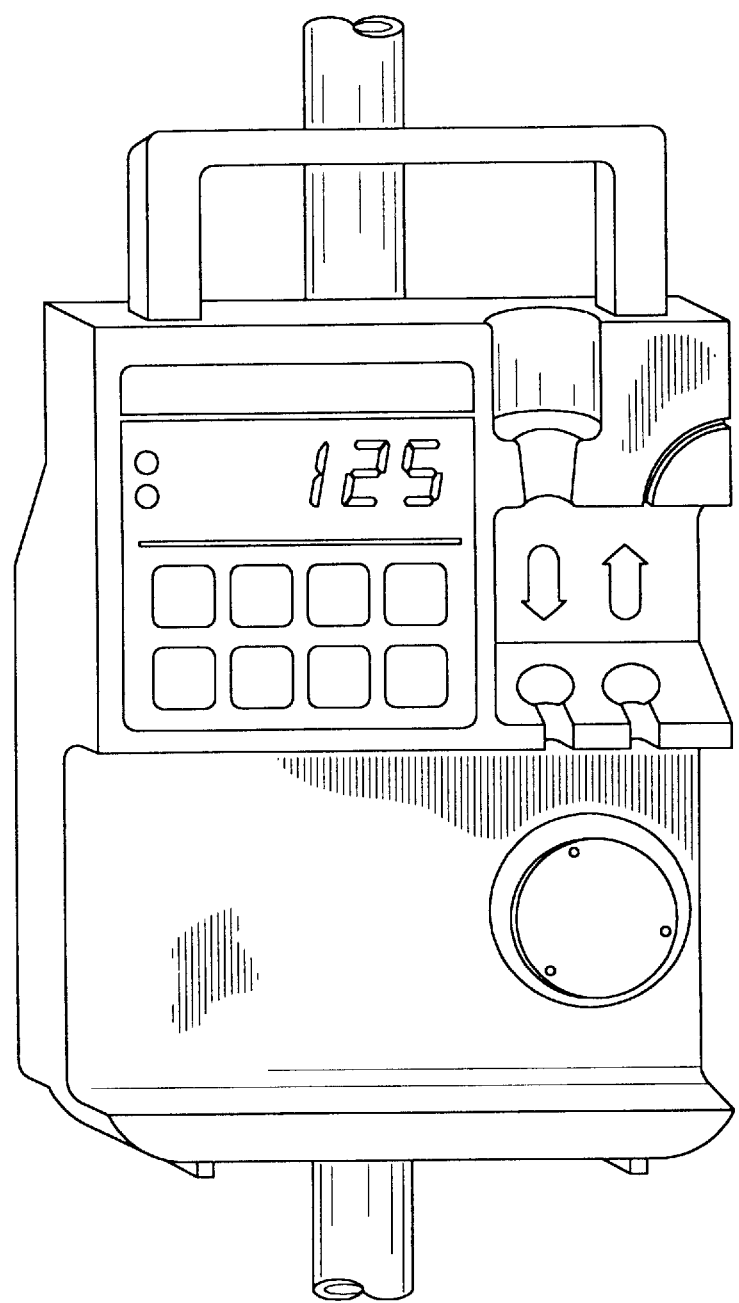
FIG. 21 is a perspective view of a peristaltic pump according to the prior art.
Figure 22:
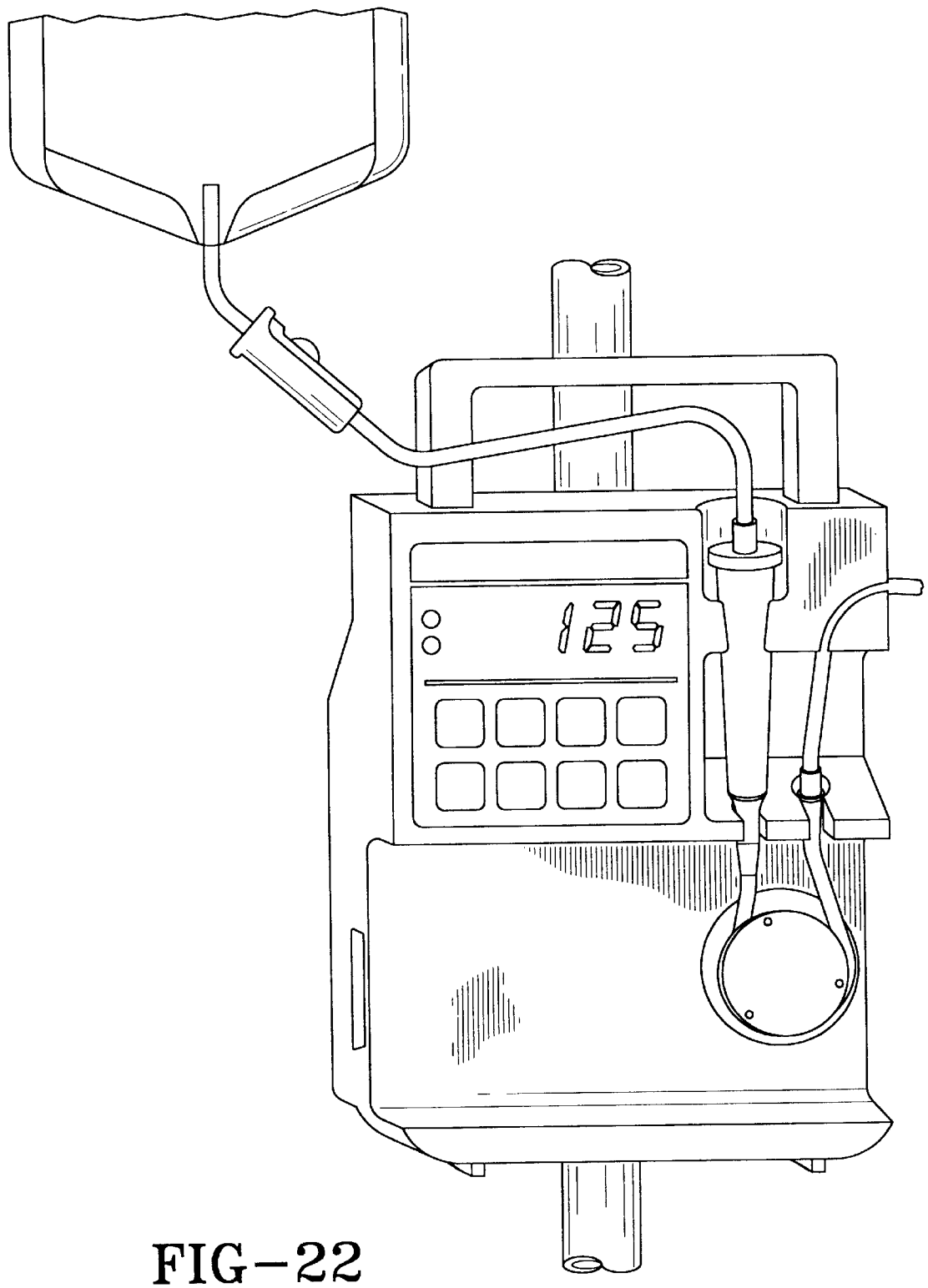
FIG. 22 is a partly fragmentary perspective view of a hanging supply container of an enteral or parenteral fluid shown connected to the inlet end of a fluid delivery set-peristaltic pump assembly according to the prior art, the fluid delivery set assembled with the prior art peristaltic pump of FIG. 21.
Figure 23:
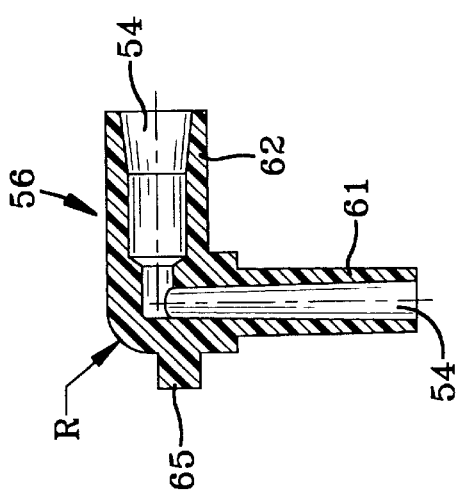
FIG. 23 is a perspective view of a preferred form of right angle retention/connector element suitable for connecting the second and third lengths of the flexible tubing of the fluid delivery set of the invention.
Figure 24:
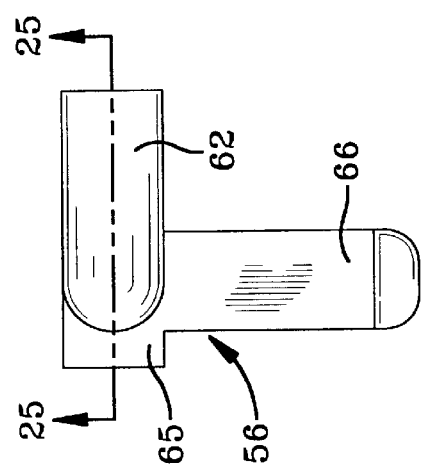
FIG. 24 is a top view of the retention/connector element of FIG. 23.
Figure 26:
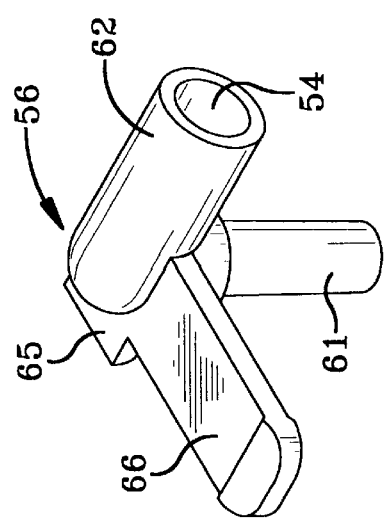
FIG. 26 is a side view of the retention/connector element of FIG. 23.
Figure 25:
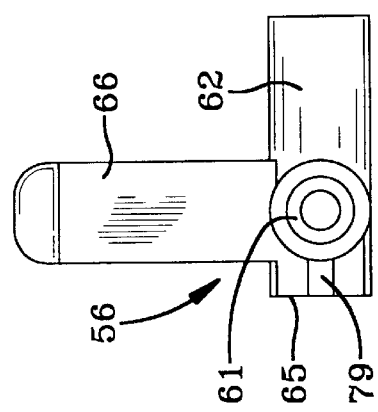
FIG. 25 is a view in vertical section of the retention/connector element of FIG. 23 taken along the line 25—25 of FIG. 24.

Positioning the guideway 67 horizontally to bring the third length 64 of flexible tubing out horizontally from the pump housing 41 is believed to be preferred by care givers over a disposition of the flexible tubing in an upward arc as it emerges along a guideway from a pump housing according to the prior art as seen in FIGS. 21 and 22. Care givers have less difficulty with maintaining the present apparatus in carefree, uncomplicated working order, especially when caring for restless patients.

The retention/connector element used in the practice of the present invention may also take one of the forms 56g–56j shown in FIGS. 35 to 38 in each of which the right angle bend of the fluid pathway is achieved in a segment of the third length 64 of flexible tubing immediately adjacent the retention/connector element instead of within the retention/connector element. In using the retention/connectors 56g–56j of FIGS. 35 to 37, the third length 64 of flexible tubing must be bent within the horizontal guideway 67, but not bent so sharply as to unduly restrict fluid flow through the bend. In using the retention/connector element 56j of FIG. 38 the third length 64 of flexible tubing is directed forwardly horizontally and special care should be taken to avoid unsupported tubing bending downwardly too sharply so as to block the flow of fluid therethrough. The use of retention/connector elements with the right angle bend within the retention/connector element is preferred.

Figure 39:
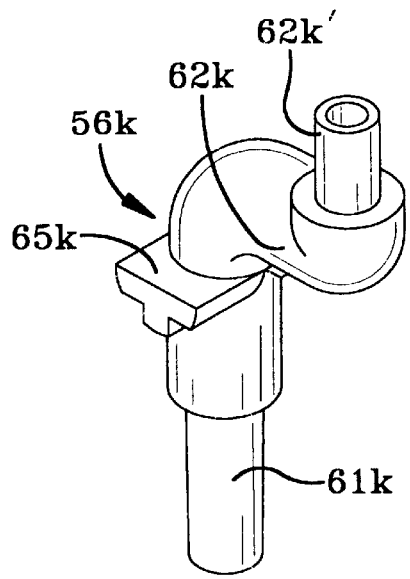
FIG. 39 is a perspective view of yet another alternative embodiment of the retention/connector element which provides a right angled passageway therethrough but supports the third length of flexible tubing forwardly of the pump housing.
Figure 41:
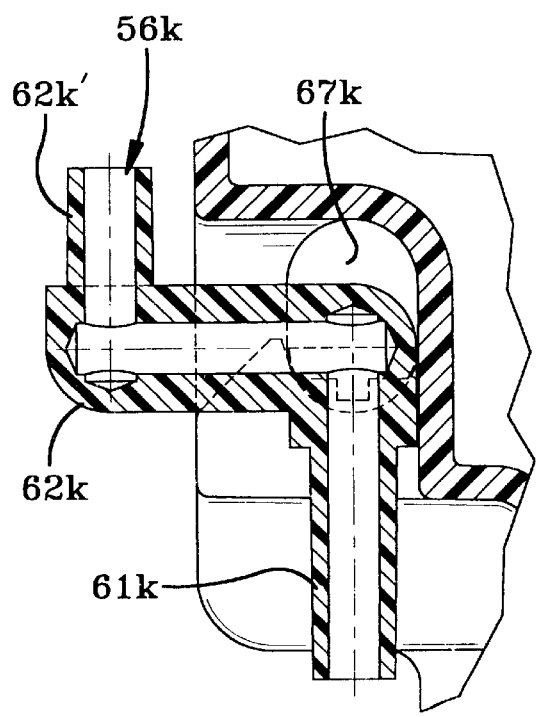
FIG. 41 is a fragmentary portion of FIG. 40 further enlarged to more clearly show the flanges of the recess as well as of the retention/connector element.
Figure 40:
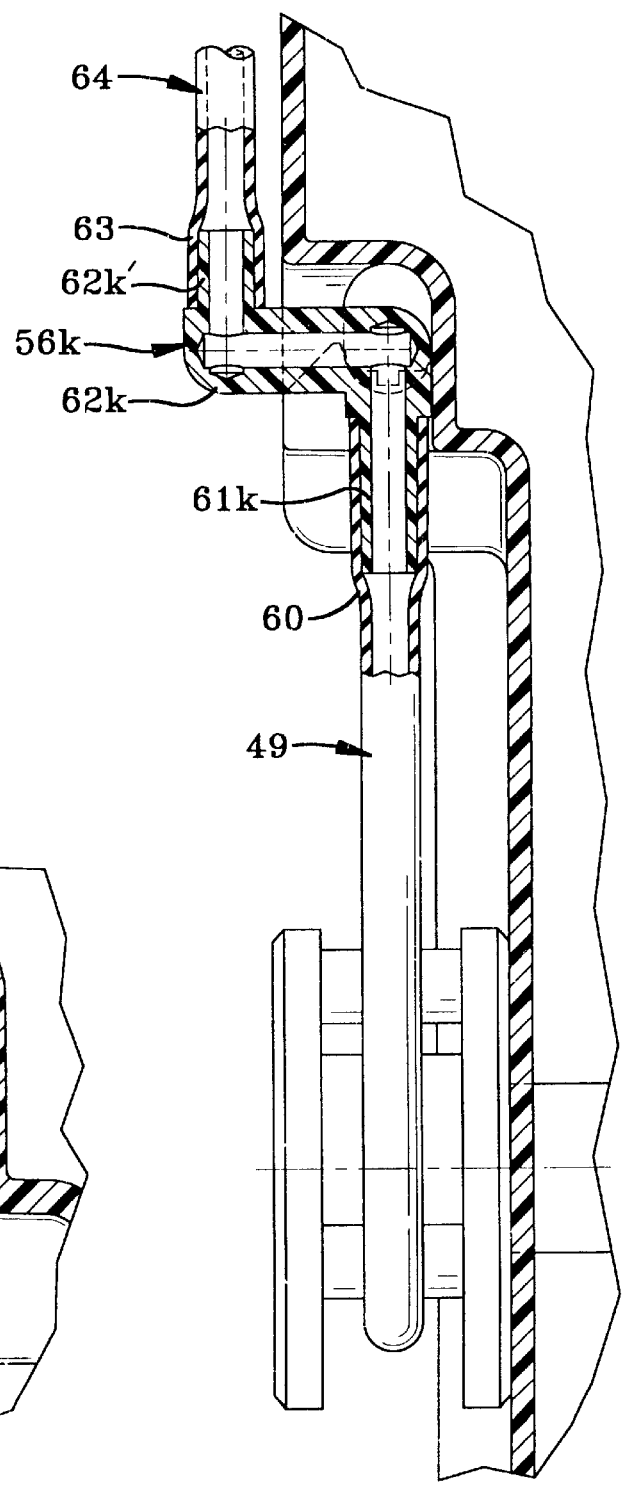
FIG. 40 is a fragmentary view mostly in vertical section taken through the front wall of the pump housing adjacent the pump rotor showing the retention/connector element of FIG. 39 assembled with a peristaltic pump of the invention.

If desired, however, the assembly of the invention having a retention/connector element 56k in the alternative form shown in FIG. 39 may be employed. In retention/connector element 56k the right angle bend of the retention/connector element projects forwardly and horizontally from the second retentive recess 55 and not towards the horizontal guideway 67. As seen in the fragmentary sectional views of FIGS. 40 and 41, the second end 60 of the second length 49 of flexible tubing connects to the lower leg 61k of the retention/connector element 56k and the retention/connector element 56k with its retention tab 65k fits interlockingly into the second retentive recess 55 with the other leg 62k of the retention/connector element 56k projecting forwardly and in dog-legged shape into a second right angle bend with a third leg 62k' extending upwardly. The first end 63 of third length 64 of flexible tubing telescopes over the third leg 62k' in making connection to this form of retention/connector element 56k, and the third length 64 of flexible tubing is allowed to arch over and down to the connection to the patient.

In assembling the fluid delivery set 42 with the peristaltic pump 40, the second length of flexible tubing 49 is slipped laterally into the guideway 50 via a vertically extending slot 50a (see FIG. 8) and then the drip chamber 43 is slid down into the guideway from the top of the pump housing until the first retention element 47 is seated in the first retentive recess 44 with the lower edge of the sidewall 73 at the back side of the recess retentively situated between the bosses 71 and the back wall of the first retentive recess 44, as may be seen in cross section in FIG. 4A.

In FIG. 4 the fluid delivery set 42 is shown assembled with the pump housing 41 with the second length 49 of flexible tubing under sufficient tension between the first retentive recess or receptacle 44 and the second retentive recess or receptacle 55 so that the second length of flexible tubing 49 is under tension and is pressed against the rollers of the peristaltic rotor 52 to facilitate peristaltic pumping when the peristaltic rotor is rotated.

As may be seen in FIG. 3 and FIG. 4A, the guideway 50 of the retentive recess 44 is very preferably provided with a substantially vertical groove 81 in the sidewall 76 of the guideway with an aperture 81a formed in the wall of the groove 81, the aperture opening to the interior of the pump housing 41. A like groove and aperture (not shown) is provided on the opposing side of the guideway 50 and the aperture aligned with aperture 81a so that a light or signal source (not shown) within the pump housing 41 may be directed through the opposing apertures, and the drip chamber 45 therebetween, to a conventional detector such as a photocell (not shown) for the detection of drops of fluid moving through the drip chamber 43. Electronic means within the pump housing may be programmed to halt the pumping operation if a continuous series of drops of fluid are not detected. Use of such a system is highly preferred as a good precautionary practice. If desired, an aperture 67a between the horizontal guideway 67 and the vertical guideway 50 may be provided, as shown in FIGS. 3 and 3A, to facilitate molding of the pump housing.

Turning again to FIGS. 2 and 3, and particularly to FIG. 3A, and having reference also to the sectional views in FIGS. 7, 8 and 8A, the second retentive recess 55 is preferably formed with flanges 78,78a at the front edge of the recess and most preferably one of these flanges is formed at the front edge at each side of the slot or notch 58 for the better retention of the retention/connector element 56. As seen more clearly in FIG. 8A the retention tab 65 of the retention/connector element is preferably formed with a flange portion 79 on the underside thereof to fit complementarily behind the flange 78 on the left side of the slot 58 as viewed from the front of the housing 41. The second retentive recess 55 is also provided with sufficient lateral depth to the left of the slot 58 to accommodate the retention tab 65 behind the flange 78 and recess wall, as may be seen illustrated in FIG. 8. In this setting the retention tab 65 is much preferred for the positive interlocking achieved with the flange or flanges 78, 78a, of the second retentive recess.

Figure 12:
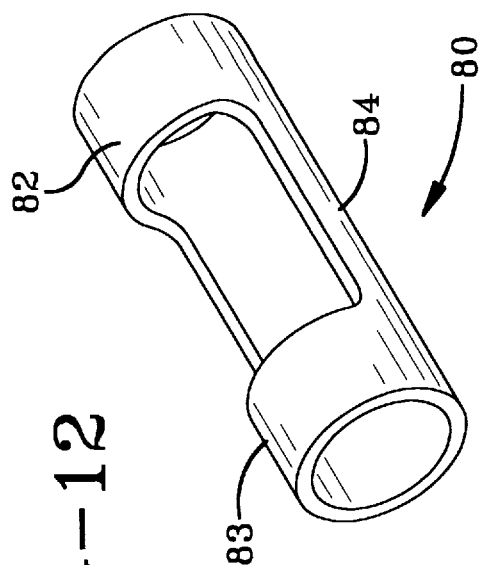
FIG. 12 is an enlarged perspective view of the pinch valve element of FIG. 11 before being telescopically mounted on the flexible tubing to provide valving action.
Figure 11:
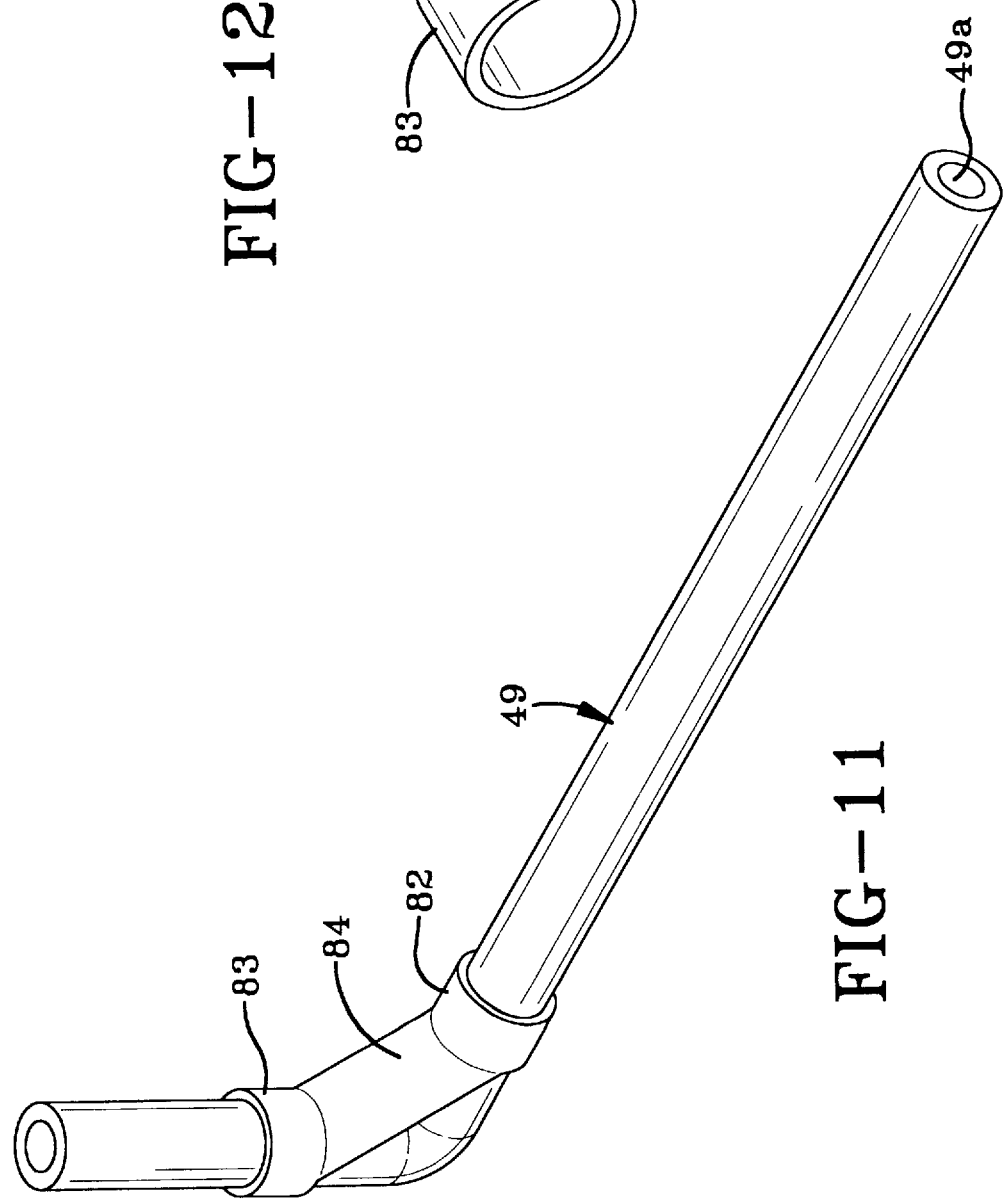
FIG. 11 is a perspective view of a length of the flexible tubing of a fluid delivery set of the invention, such as the second length 49, with a novel pinch valve element telescoped thereon kinking the tubing in valving action when the tubing is not under tension.

It is preferred that a pinch valve 80 be employed as a component of the fluid delivery set as a precaution against unintended and uncontrolled fluid flow in the event the fluid delivery set 42 is dislodged from the pump housing whereby the rollers 53 of the peristaltic pump rotor 52 do not control fluid flow. Referring to FIGS. 2–5 and 12–16, a pinch valve 80, such as that depicted in FIG. 12, is shown mounted on the second length 49 of flexible tubing between the peristaltic rotor 52 and the second retentive recess 55, which is a preferred location for the pinch valve. However, it should be understood that the pinch valve may be located between the outlet of the drip chamber and the peristaltic rotor if desired. The tension on the second length 49 of flexible tubing should also be sufficient to unkink or unpinch the pinch valve 80 sufficiently for substantially unimpeded flow of fluid therethrough and the pinch valve should be responsive to the level of tension that is sufficient for proper action of the peristaltic rotor.

As indicated, it is preferred to employ with the fluid delivery set of the invention a pinch valve that may be used to pinch shut the flexible tubing at some point along the fluid pathway, and preferably the pinch valve is automatic in operation and responsive to tension, especially the lack thereof. The preferred pinch valves pinch or kink the flexible tubing sufficiently to block fluid flow through the flexible tubing when there is not sufficient tension on the flexible tubing where the pinch valve is located. Thus, if the fluid delivery set is dislodged from the pump housing or the fluid delivery set is not properly assembled with the pump housing and the flexible tubing is not pressed against the rollers of the peristaltic rotor, the pinch valve will substantially prevent flow of fluid through the fluid delivery set.

A preferred form of pinch valve element is shown in FIG. 12 and consists of a single member 80 formed of elastically flexible polymeric material such as silicone rubber like, or similar to, the silicone rubber employed in the second length of flexible tubing of the fluid delivery set, but having foreshortened cylindrical tubular segment end portions 82, 83 connected by a nearly hemi-cylindrical shank portion 84 integrally formed therewith. In a working embodiment the inside diameter of the pinch valve element 80 prior to assembly is actually less than the outside diameter of the second length of flexible tubing of the feeding set 42 which results in good position retention on the length 49 flexible tubing when assembled. In the working embodiment the pinch valve element is die cut from the same kind of flexible tubing that is employed as the second length of flexible tubing in the fluid delivery set.

Figure 13:
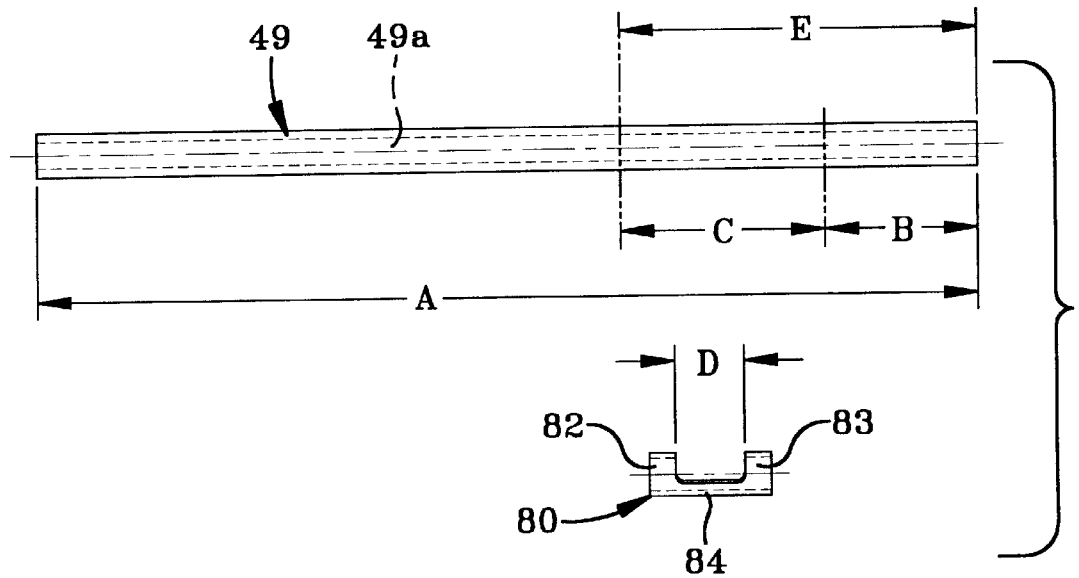
FIG. 13 is a side elevation view of the components of a pinch valve.
Figure 14:
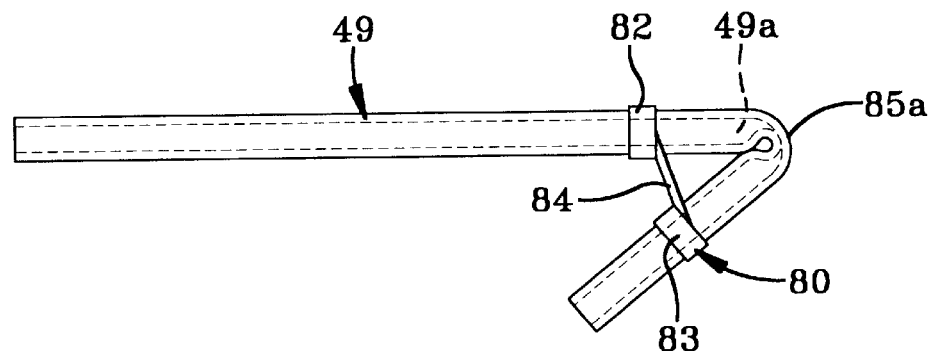
FIG. 14 is a side view of a section of flexible tubing that has been kinked by the novel pinch valve element of FIG. 12.
Figure 15:
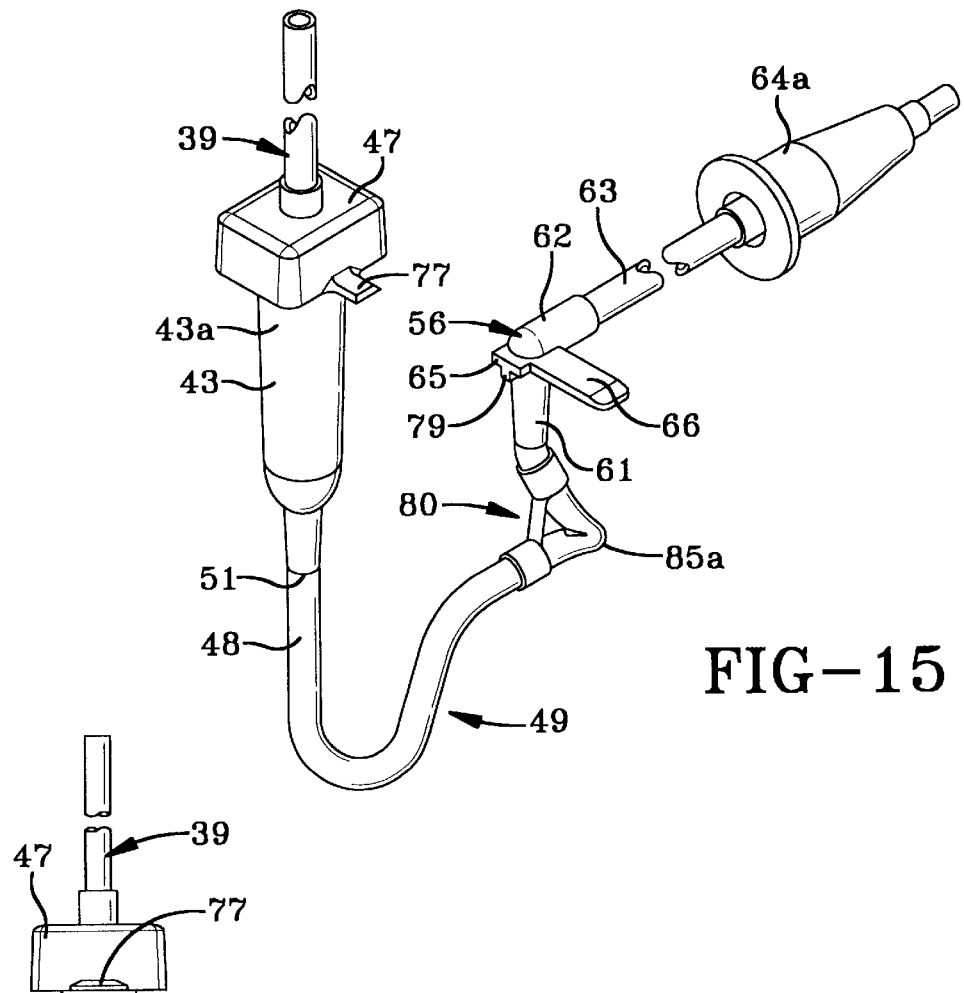
FIG. 15 is a perspective view of a fluid delivery set like that shown in FIG. 9 but having a pinch valve element telescoped on the flexible tubing near the second retention element.
Figure 16:
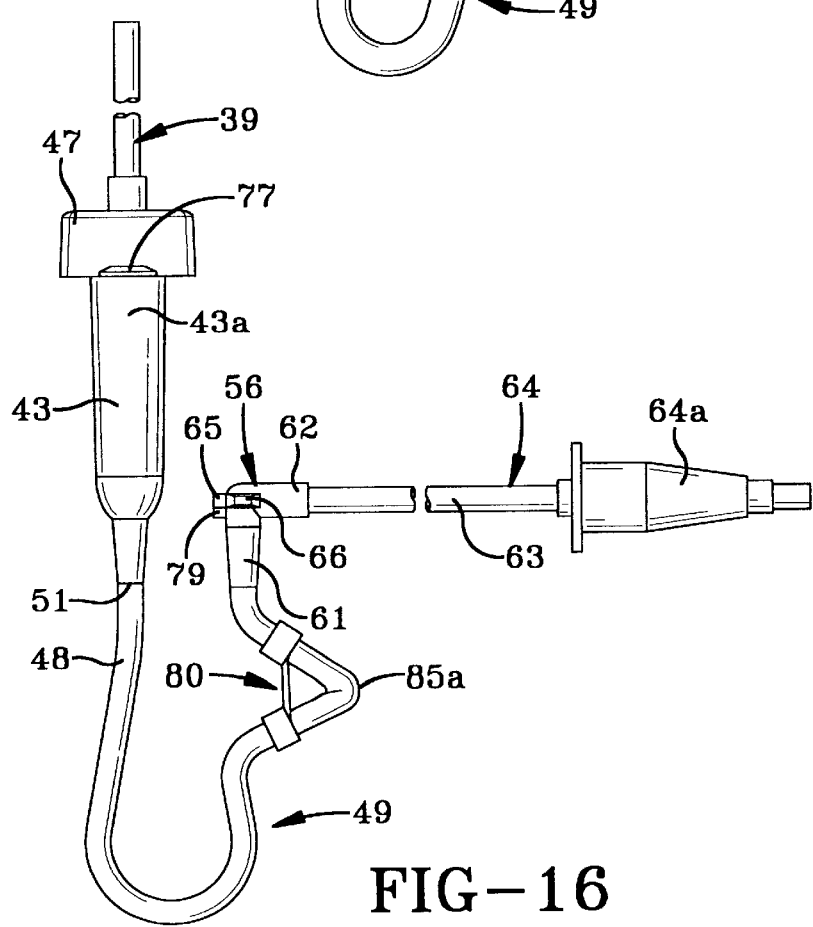
FIG. 16 is a front view of the fluid delivery set of FIG. 15.

Referring now to FIGS. 13 and 14, the pinch valve element 80 is installed on flexible tubing such as second length 49 with one end of the pinch valve element located a distance "E" from the end of the tubing such that the other end of the pinch valve element is located a distance B from the end of the tubing sufficient to facilitate connecting the tubing to another component. The tubular segment end portions 82, 83 of the pinch valve element are spaced apart a distance "C" along the flexible tubing 49 whereas the shank portion 84 assumes a length "D" when not under tension, the length "D" being sufficiently shorter than the length "C" to bend over and pinch the tubing shut when not under sufficient tension to stretch the shank portion 84. As an example, with a flexible silicone rubber tubing of 0.33 cm. (0.131 inch) inner diameter, 0.51 cm. (0.199 inch) outer diameter and a wall thickness of about 0.086 cm. (0.034 inch), and with a pinch valve 80 element die cut from the same type of tubing having the inner edges of the tubular end portions 82, 83 spaced apart by a shank portion about 0.51 cm. (0.199 inch) in length when not under tension, the inner edges of the tubular end portions 82, 83 should be separated by a distance of about 2.0 cm. (0.80 inch) when installed telescopically on the second length 49 of flexible tubing, in order to obtain a desired tightness of pinching or kinking to block fluid flow. For a given elastically flexible tubing, the dimensions are very important to obtain the desired valve action with good opening and sufficiently positive shut off. The length of the flexible tubing embraced between the tubular segment end portions of the pinch valve element is especially important to get sufficient doubling over for a sharp bend, but not so much as to form a looser loop. This can be determined empirically by trial and error for a given size flexible tubing made of a material with a given modulus of elasticity.

Figure 43:
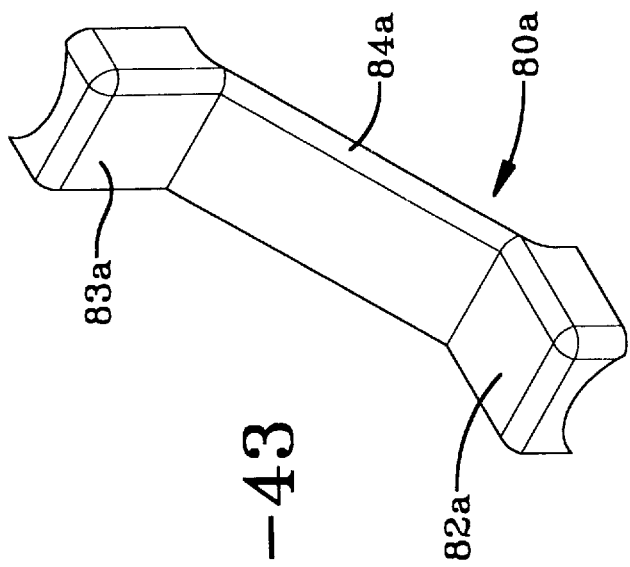
FIGS. 42 and 43 are perspective views similar to FIGS. 11 and 12, respectively, of an alternative pinch valve element assembled with a length of flexible tubing and of the pinch valve element by itself.
Figure 42:
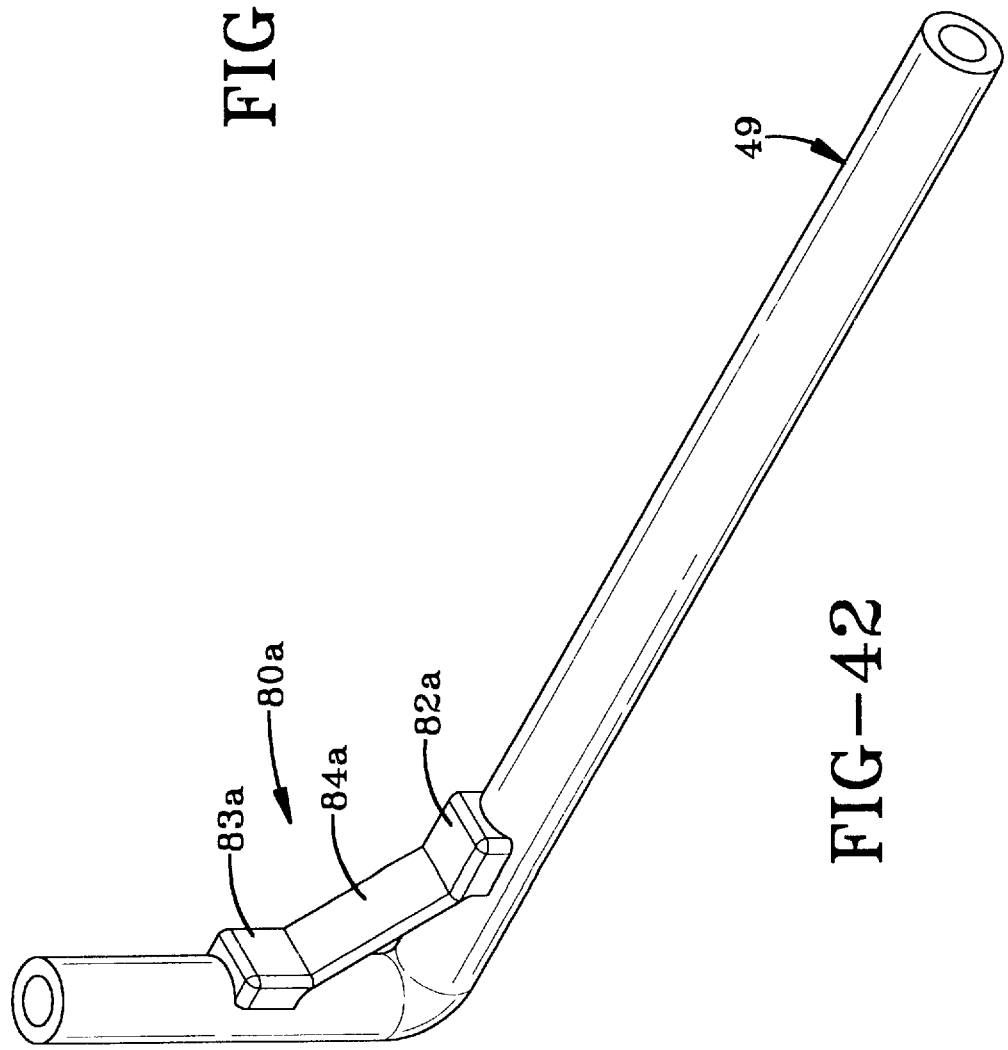

In FIG. 43 there is shown an alternative pinch valve element 80a having a rectangular substantially planar shank portion 84a connecting rectangular substantially planar end portions 82a,83a. The end portions 82a,83a each have a concave surface adapted to fit conformingly against the outer cylindrical surface of the flexible tubing 49 and are bonded or cemented thereto, as seen in FIG. 42, after bending the flexible tubing section encompassed by the pinch valve element so that attachment can be made with the length of the shank portion 84a much shorter than the length of encompassed flexible tubing section in the resulting pinch valve.

In FIG. 45 there is seen another alternative pinch valve element 80b that is shaped like the capital letter "I" and formed of a flat, sheet-like, elastic, flexible, polymeric material. The pinch valve element 80b is attached to the flexible tubing 49 by wrapping the wider sheet-like end portions 82b, 83b substantially around the flexible tubing and bonding or cementing them thereto as seen in FIG. 44 at locations spaced further apart longitudinally of the flexible tubing 49 than the length of the shank portion 84b whereby the flexible tubing section encompassed by the end portions 82b,83b is doubled over and pinched shut as shown in FIG. 44 when the flexible tubing 49 is not under longitudinal tension.

Yet another alternative pinch valve element 80c is seen in FIG. 47 in which a shank portion 84c having an arcuate cross section of half-cylinder or hemi-cylindrical shape joins arcuate end portions 82c,83c that are accurately slotted on the concave surface that is mated with the cylindrical outer surface of the flexible tubing 49 as shown in FIG. 47A. As in the case of the other pinch valve embodiments depicted herein, the flexible tubing 49 is bent during the assembly of the pinch valve seen in FIG. 46 so that the encompassed section of the flexible tubing will be much longer than the shank portion 84c of the pinch valve element. Thermal bonding or cementing of the pinch valve element end portions 82c,83c to the flexible tubing 49 completes the manufacture of the pinch valve shown in FIG. 46.

Figure 49:
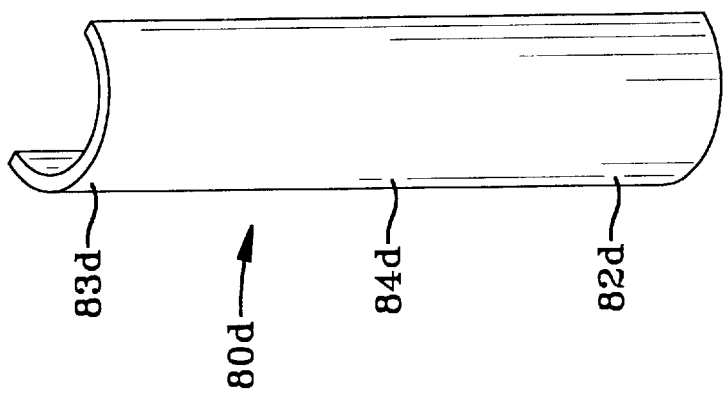
FIGS. 48 and 49 are perspective views similar to FIGS. 11 and 12, respectively, of an alternative pinch valve element assembled with a length of flexible tubing and of the pinch valve element by itself.
Figure 48:
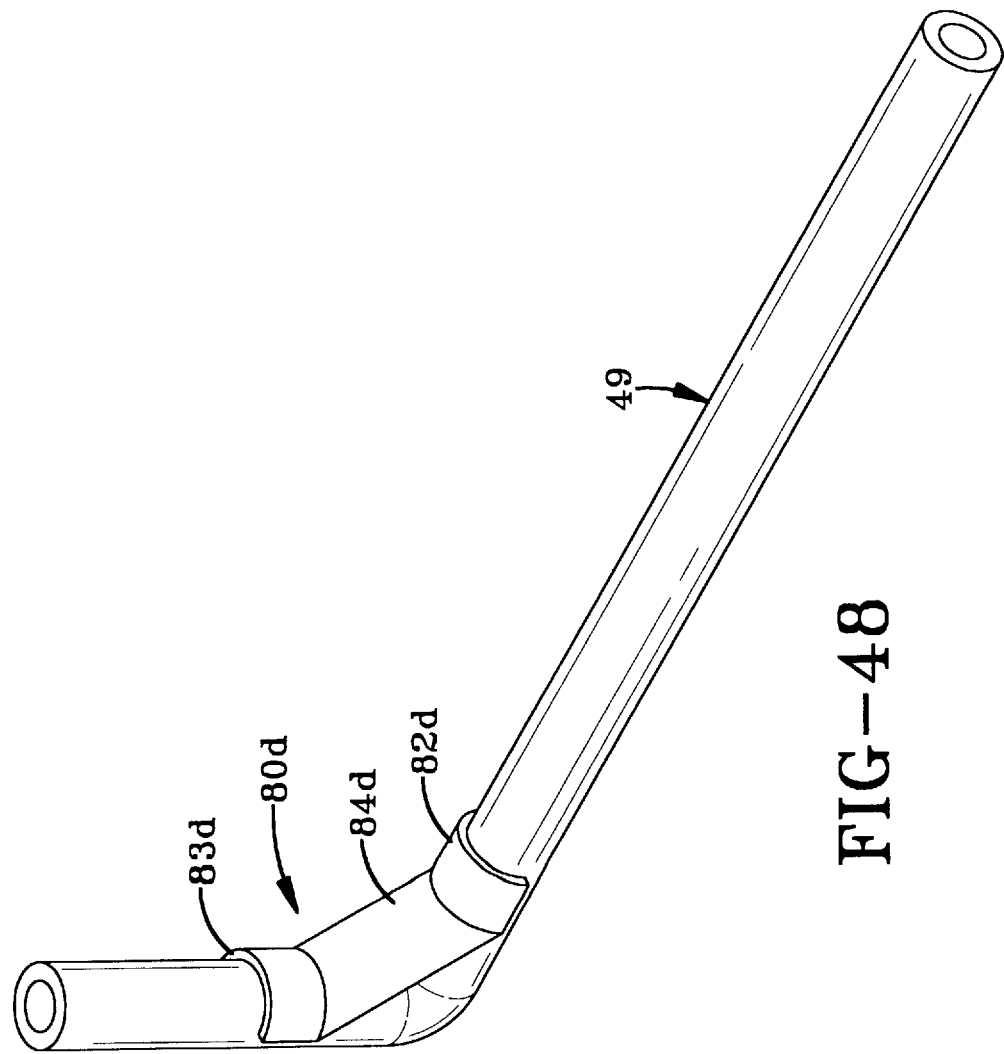

Still another alternative pinch valve element 80d is shown in FIG. 49 in which a shank portion 84d and end portions 82d, 83d are all part of one hemi-cylindrical sleeve-shaped piece of elastically flexible polymeric material which is shown in FIG. 48 attached, for example by bonding or an adhesive, to flexible tubing 49 to form another embodiment of the pinch valve of the invention. Again, in bonding or cementing the shank portion 84d to the flexible tubing 49, the tubing section encompassed by the pinch valve element is bent sharply so that the end portions 82d,83d of the pinch valve element will be attached at locations longitudinally spaced along the flexible tubing 49 such that tubing section encompassed by the pinch valve element will be substantially longer than shank portion 84d to provide the tension responsive valve effect.

Figure 50:
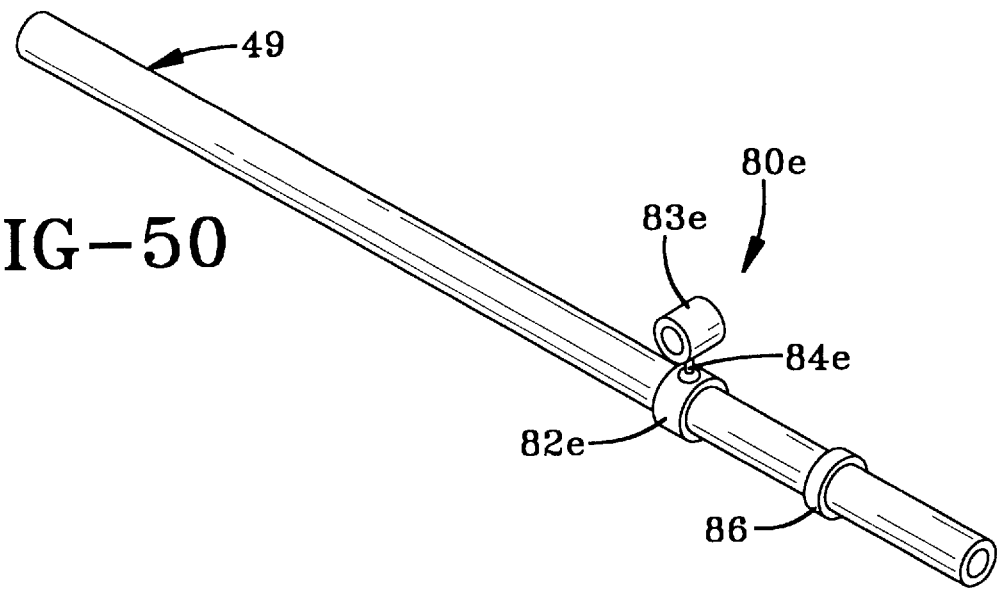
FIG. 50 is a perspective view of a length of flexible tubing partly assembled with an alternative pinch valve element.
Figure 51:
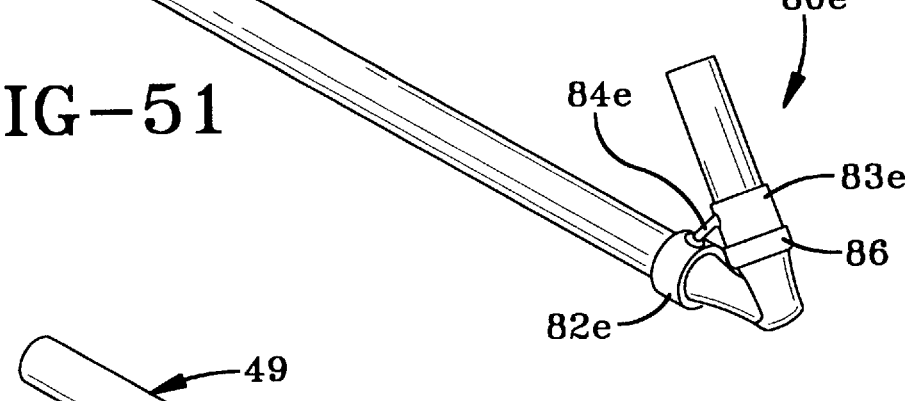
FIG. 51 is a perspective view of the pinch valve of FIG. 50 fully assembled, the flexible tubing not being under tension.
Figure 52:
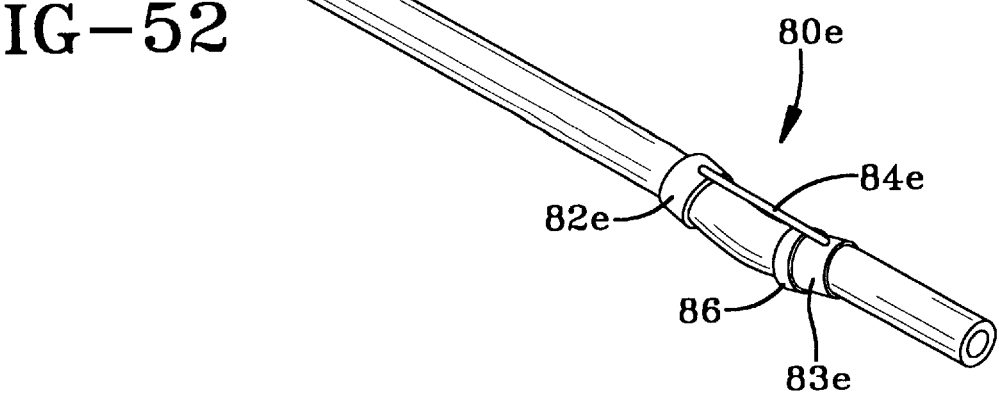
FIG. 52 is a perspective view of the flexible tubing and pinch valve of FIG. 51 with the tubing under sufficient tension to open the pinch valve.

Another embodiment of a pinch valve element 80e is depicted partly, and also entirely, assembled with a length of flexible tubing in FIGS. 50–52. Pinch valve element 80e comprises foreshortened tubular segment end portions 82e, 83e joined by a strip or rod-like shank portion 84e. The end portion 82e is initially insert molded to the flexible tubing 49, as is positioning collar 86 which is spaced apart from the end portion 82e by the intended length of encompassed flexible tubing section. The section of the flexible tubing 49 positioned between the tubular segment end portion 82e and positioning collar 86 is then bent sharply and tubular segment end portion 83e is slipped over the adjacent end of flexible tubing 49 until the end portion 83e is against the positioning collar 86 where the tubular segment end portion 83e is bonded or cemented in place, thus forming the pinch valve depicted in FIG. 51. As shown in FIG. 52, when the tubing 49 is placed under sufficient longitudinal tension, shank portion 84e yields and encompassed flexible tubing section straightens out sufficiently that fluid may flow therethrough.

Figure 55:
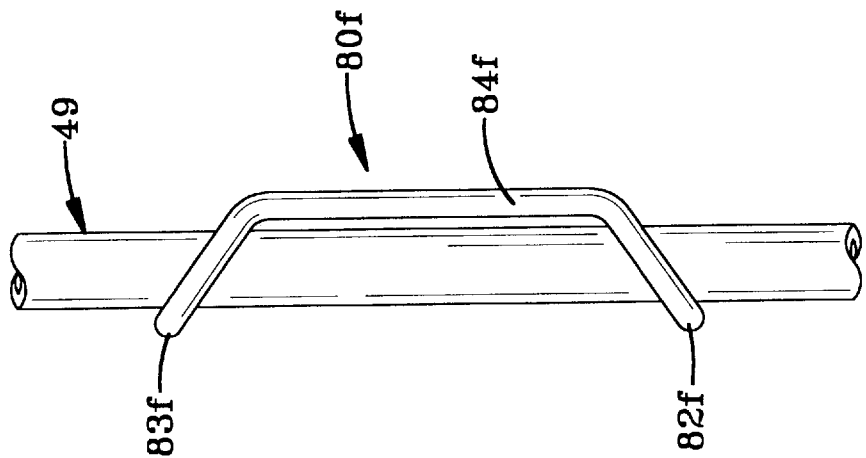
FIG. 55 is a view in side elevation of the assembly of FIG. 54 with the flexible tubing under sufficient tension to open the pinch valve.
Figure 54:
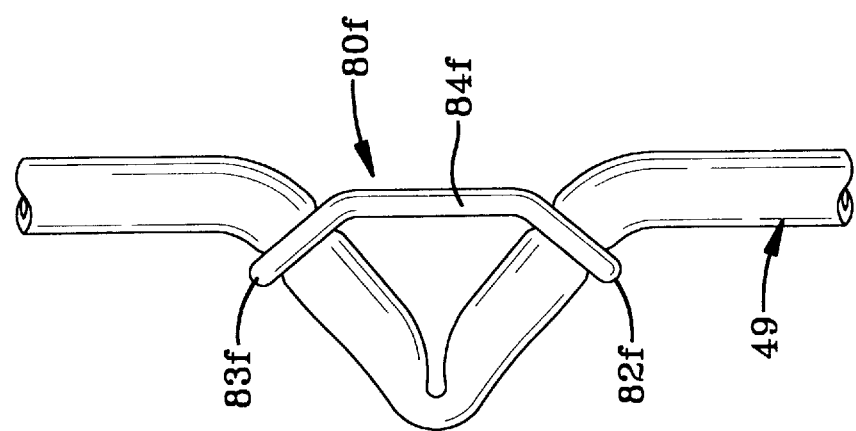
FIG. 54 is a view in side elevation of an assembly of the pinch valve element of FIG. 53 and a length of flexible tubing, the tubing being in a relaxed state.
Figure 53:
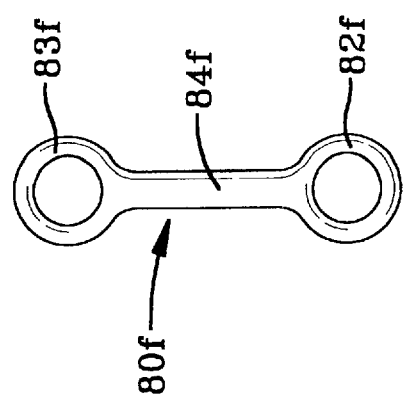
FIG. 53 is a view in front elevation of yet another alternative pinch valve element.

Referring now to FIGS. 53–55, another embodiment of a pinch valve element 80f is seen having closed loop or eye-like end portions 82f,83f joined by a narrower shank portion 84f. An end portion 82f of the pinch valve element is emplaced telescopically around the flexible tubing 49 a selected distance from an end thereof and the flexible tubing is then bent sharply between the position of the end portion of the pinch valve element 82f and the nearest end of the flexible tubing and the other end portion 83f is telescopically emplaced around the flexible tubing to a position defining an encompassed flexible tubing section and the end portions are bonded or cemented in place. For example a room temperature vulcanizing silicone polymer composition may serve as a suitable adhesive to be inserted along or just under the margins of the pinch valve element end portions. The completed pinch valve is tension responsive, kinking shut when not under tension as seen in FIG. 54 and being openable under sufficient tension as depicted in FIG. 55.

Referring now to FIG. 56, still another form of tension responsive pinch valve is made by molding a sharply bent piece of a highly elastic springy material, such as metallic spring wire 181, or a suitable polymeric material, in the wall 182 of a length of flexible tubing. The memory of the sharply bent springy material causes the flexible tubing to be pinched shut when there is not enough longitudinal tension applied to the flexible tubing. As seen in section in FIG. 57, the wall of the tubing is made thicker along a longitudinal side to accommodate the molding of the high elastic springy material therewith. In yet another form of tension responsive pinch valve 80*h* a sharply bent piece of a highly elastic springy material, such as a spring wire 181, or a suitable polymeric material, may also be molded onto or adhered onto, the outside of the wall 183 of the flexible tubing as indicated in section view in FIG. 57A.

Utilizing another mode of action a tension responsive pinch valve is made using a springy pinch valve element that is pre-formed with a memory that causes the ends of the valve element to twist sufficiently to close the lumen of a flexible tubing telescopically embraced by the valve element. Such a pinch valve element is identified by the reference numeral 80*i* in FIG. 58 where the pinch valve element, having tubular segment end portions 82*g*,83*g* and a shank, in the form of a plurality of longitudinal ribs 84*g* that are helically twisted, connecting the end portions, is shown assembled telescopically on a length of a length of flexible tubing. During assembly, the pinch valve element 80*g* is placed under longtidinual tension to straighten the longitudinal ribs 84*g* while the length of flexible tubing 49 is inserted through the pinch valve element and bonded or adhesively attached thereto while the longitudinal tension on the pinch valve element 80*g* is maintained. On relexing the longitudinal tension on the assembled pinch valve, the pinch valve element 80*g* twists the encompassed section of the flexible tubing, kinking it shut. Under tension, the resulting pinch valve untwists to unpinch the flexible tubing, permitting fluid passage therethrough.

It is thus evident that many embodiments of the pinch valve element employed herein may be made in many different forms from elastically flexible polymeric material and shaped to have two end portions connected by a shank portion. The end portions must be attachable to the flexible tubing of which the pinch valve is formed and must be attached with the end portions spaced apart a greater linear distance along the flexible tubing than the length of the unstretched shank portion of the pinch valve element, a relative distance in the range of about 4:1, varying only slightly as will at once be apparent, according to the elastic yield strength of the shank portion of the pinch valve element and the bend strength modulus of the flexible tubing, so that the encompassed tubing section will be pinched or kinked sharply enough by the pull of the shank portion when the pinch valve is not under tension that shut-off or occlusion of fluid flow through the flexible tubing will take place.

In all embodiments the shank portion must deform elastically under appropriate tension for the setting in which the valve is used that the pinch valve will open under longitudinal tension applied to the flexible tubing for the operations or procedures being carried out, yet close when the tension is released or absent.

A tension responsive pinch valve of the type shown in FIGS. 11–16 has been assembled by emplacing the pinch valve element upon a length of tubing using the assembly apparatus disclosed herein which has utility for placing a flexible, and at least somewhat elastic, foreshortened tubular segment telescopically upon and near an end of a length of tubing having an outer diameter substantially the same or greater than the inner diameter of the tubular segment. A very important aspect of the assembly apparatus disclosed herein is the capacity to eject the assembled combination of a flexible tubular segment and a length of tubing from the assembly apparatus without displacing the flexible tubular segment longitudinally along the length of tubing.

For the purposes of the specification and claims it should be understood that the front side or surface, also referred to herein as a first surface, of the assembly apparatus is the side or surface into which the length of tubing is inserted for emplacement of a flexible tubular segment thereon, while the back or rear side or surface is opposite the front side or surface. A forward motion is a motion towards the front side or surface as here defined, while a rearward motion or extension is taken in the opposite direction.

Figure 59:
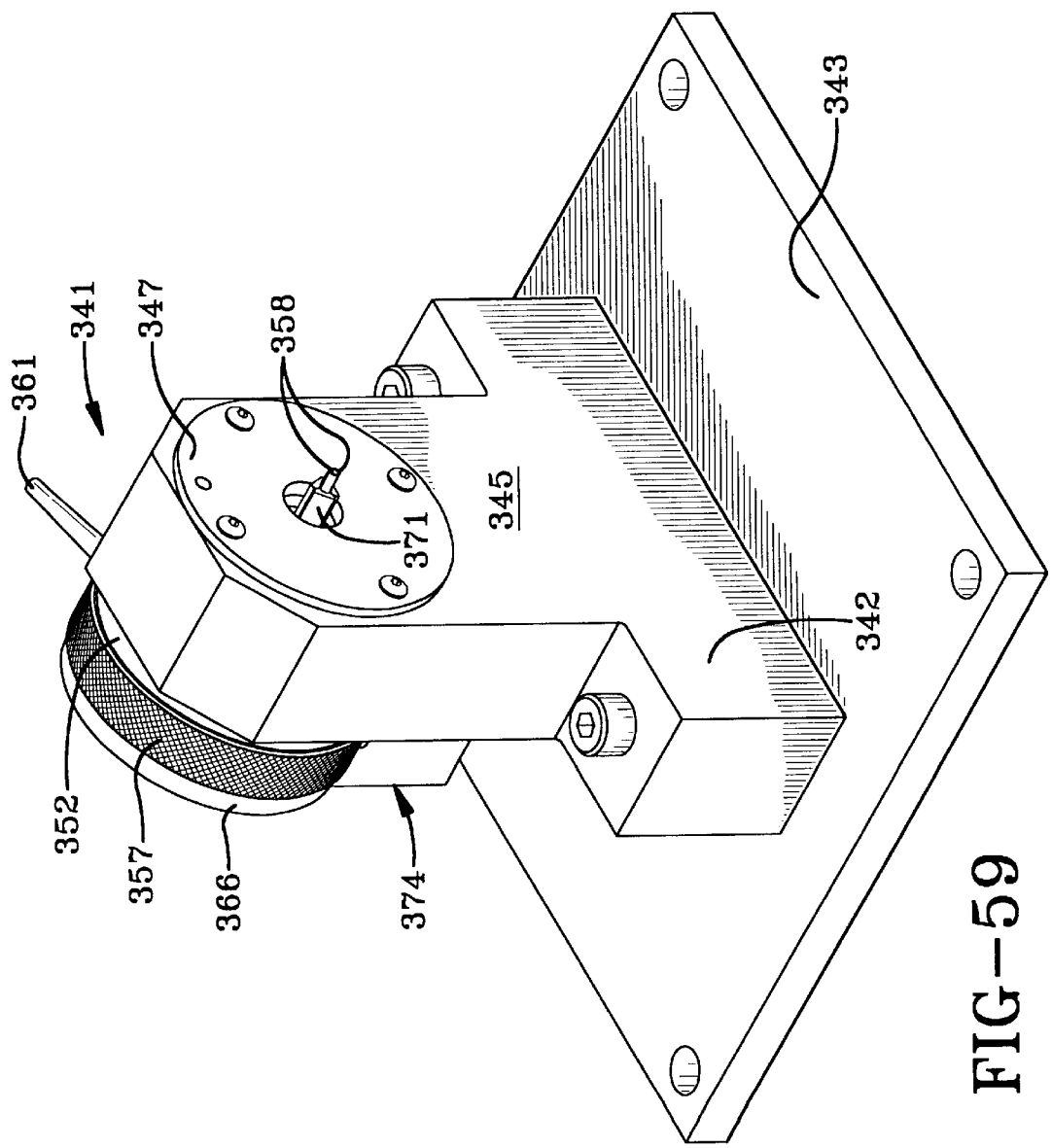
FIG. 59 is a perspective view of the front and side of an assembly apparatus which has been used to assemble a pinch valve element with a length of tubing.
Figure 60:
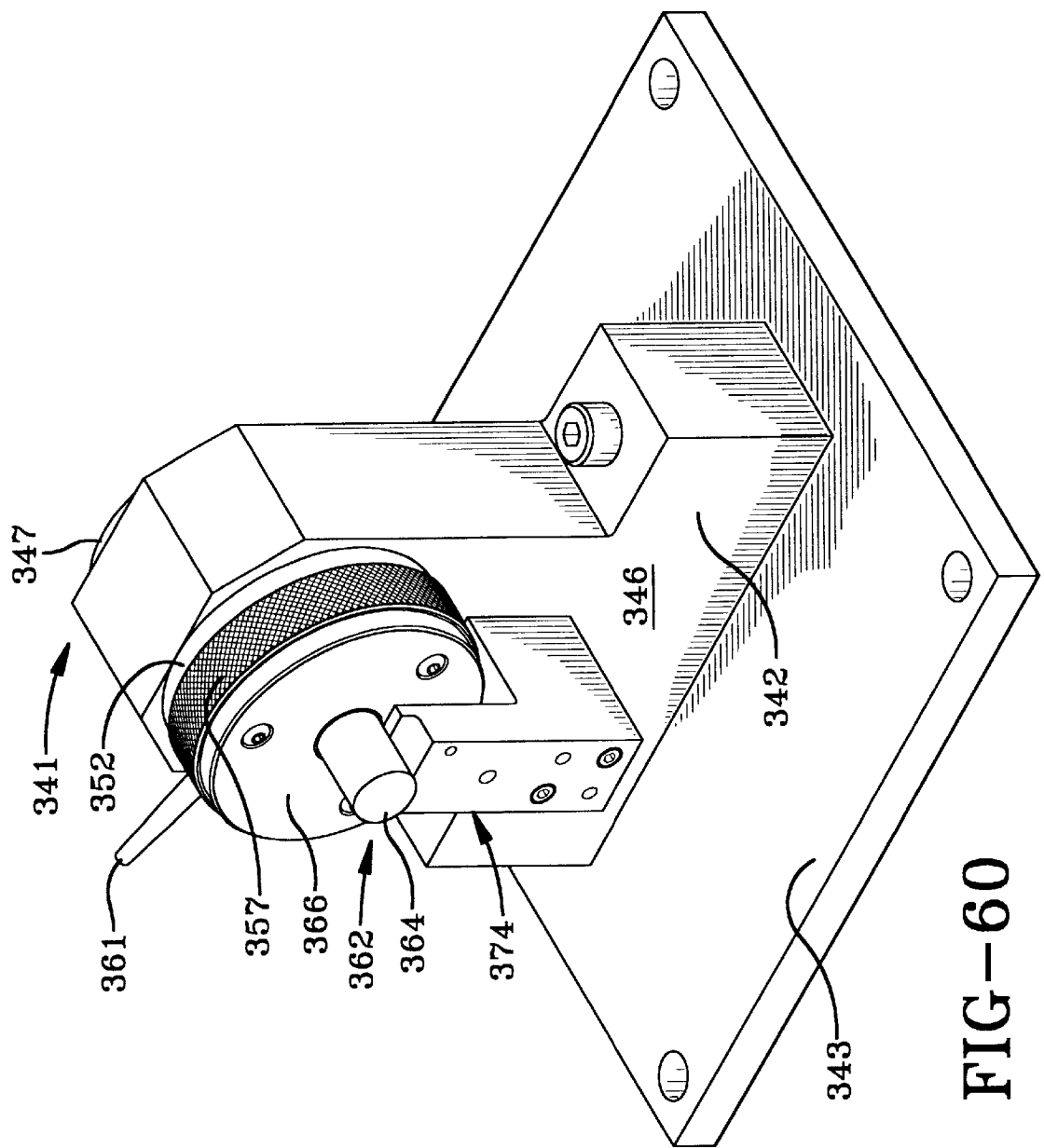
FIG. 60 is a perspective view of the back and side of the assembly apparatus of FIG. 59.
Figure 61:
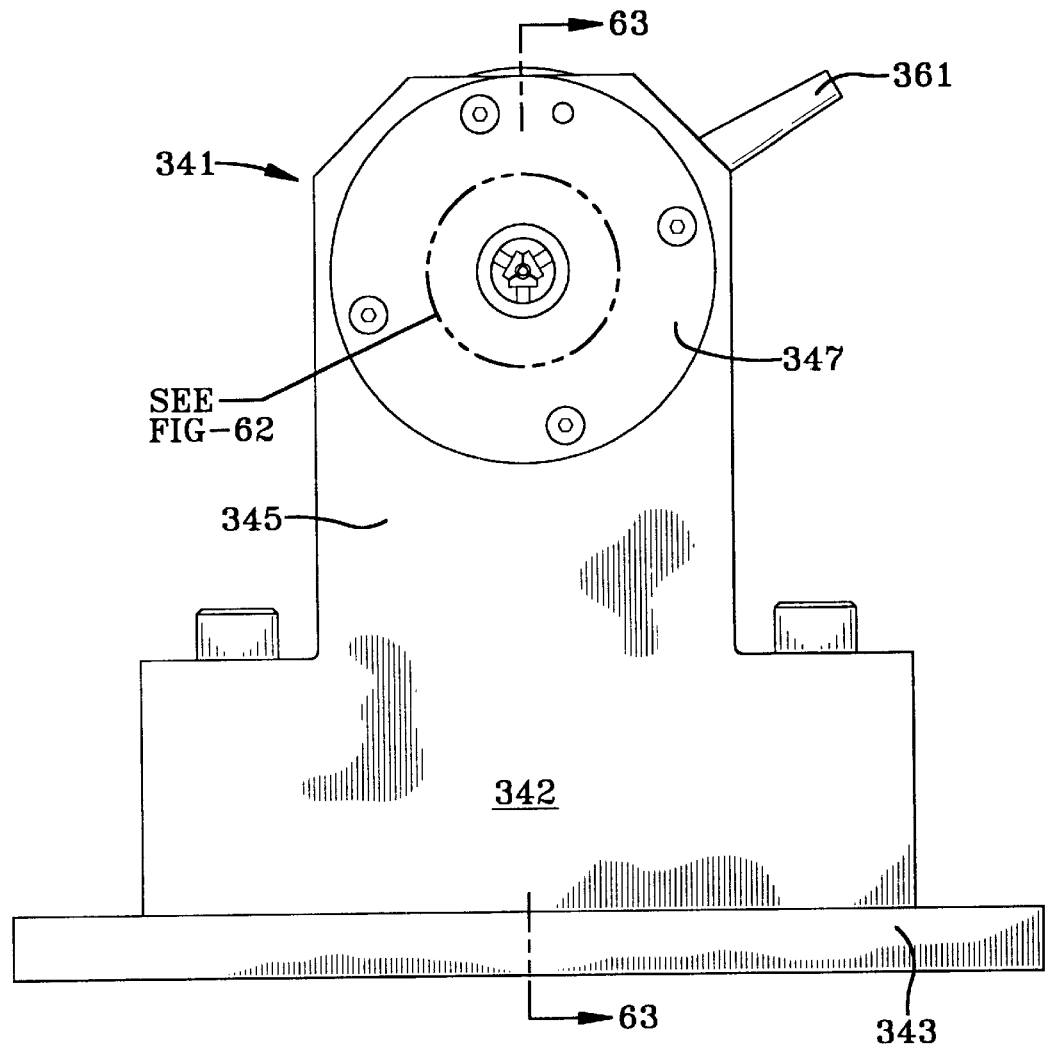
FIG. 61 is a front elevation view of the assembly apparatus of FIG. 59.
Figure 62:
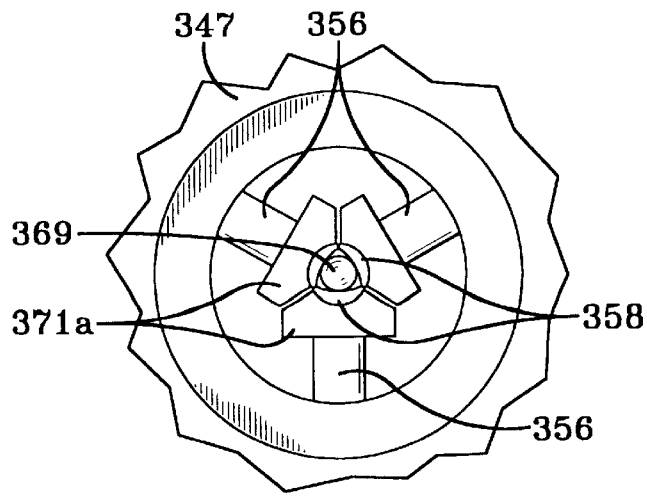
FIG. 62 is very greatly enlarged fragmentary view of the portion of FIG. 61 encircled by a dashed line.
Figure 63:
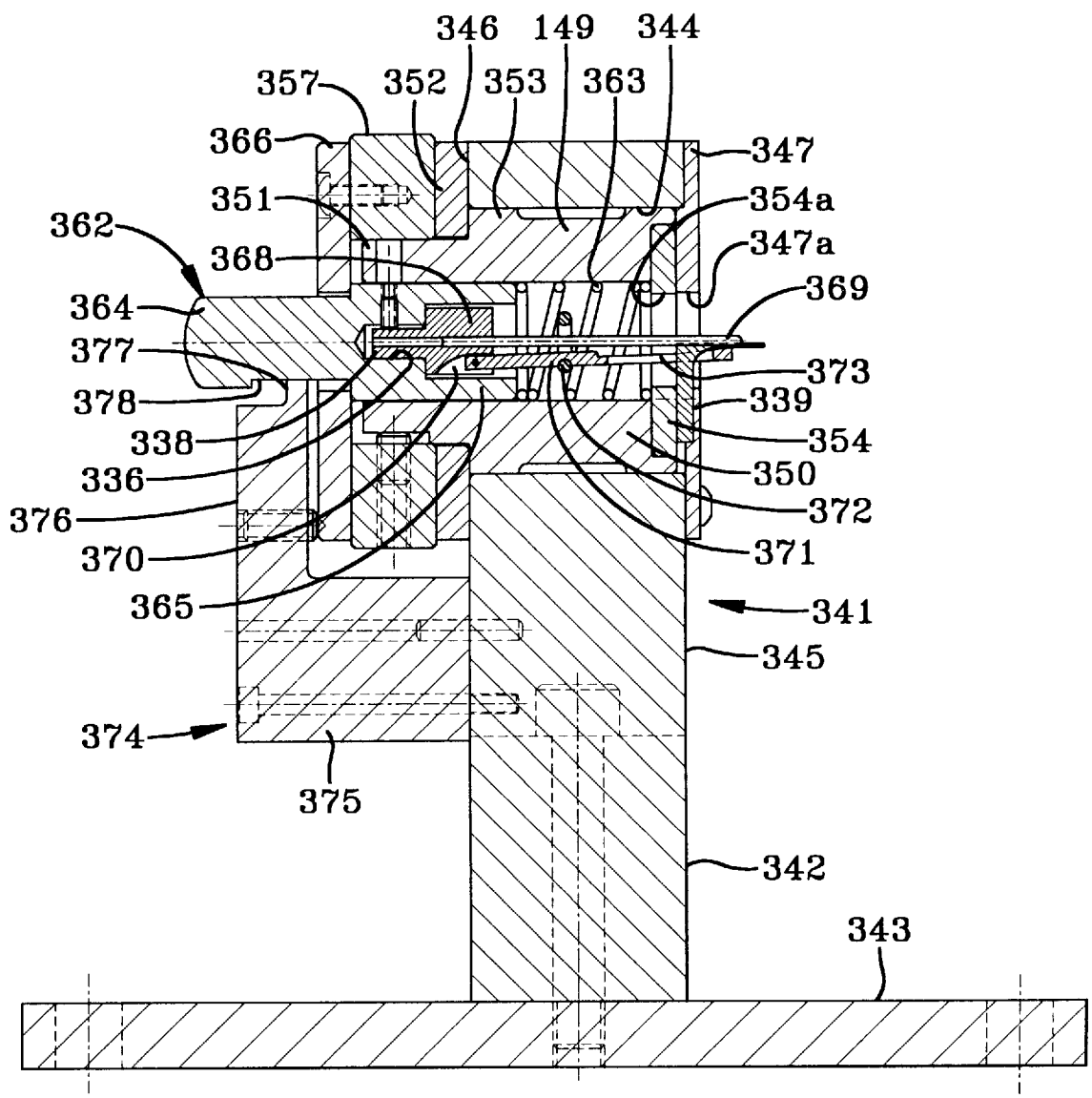
FIG. 63 is a view in vertical section of the assembly apparatus taken along the line 63—63 of FIG. 61.
Figure 64:
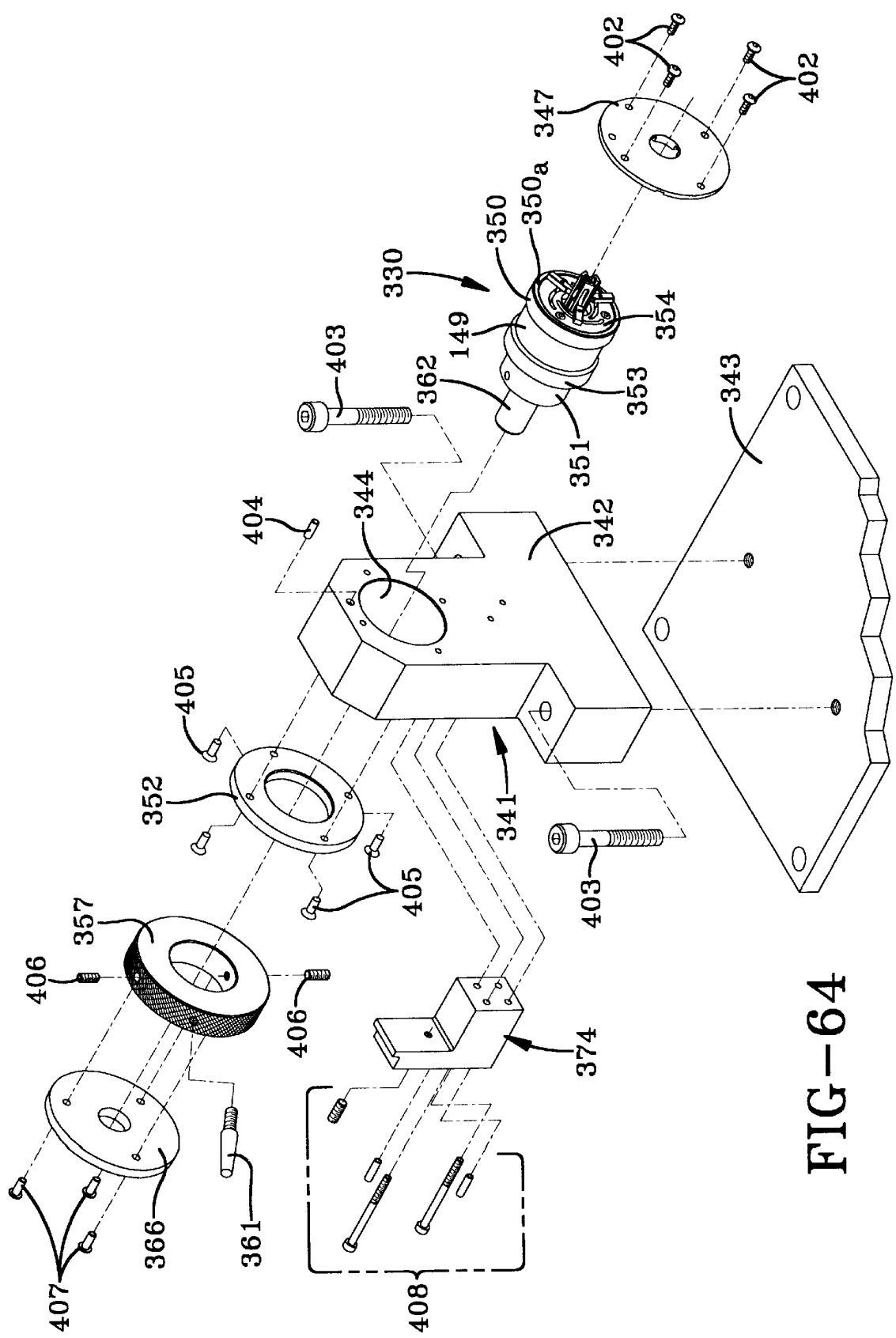
FIG. 64 is an exploded perspective view of the components of the assembly apparatus with a corner of the base plate cut away for purposes of illustration.

As seen in the exemplary embodiment shown in FIGS. 59–61, and the view in section in FIG. 63, along with the exploded view in FIG. 64, the present assembly apparatus is made up of a body portion, indicated generally by the reference numeral 341; which may if desired have a base support portion 342, which may be secured to a base plate 343, for example by bolts 403, if desired, for stability during use. It is to be understood that the support structure may take any suitable shape and orientation and the parts thereof attached together by any suitable means such as welding or clamping.

As seen in FIG. 64, the exemplary assembly apparatus consists mainly of the body portion and suitable base or support portions, in addition to a sub-assembly, indicated generally by the reference numeral 330, a cover plate 347, a first retainer ring 352, a control ring 357, a second retainer ring 366 and a rear support element 374. In the assembled apparatus the sub-assembly 330 having controllably spreadable and retractable spreader finger portions is positioned in a cylindrical bore 344 that extends through the body portion 341 from the first, or front, face to the second, or rear, face and the other components are attached in the sequence and positions indicated, using screws and bolts 402, 405, 406, 407, 408 or other suitable fastening means.

Figure 68:
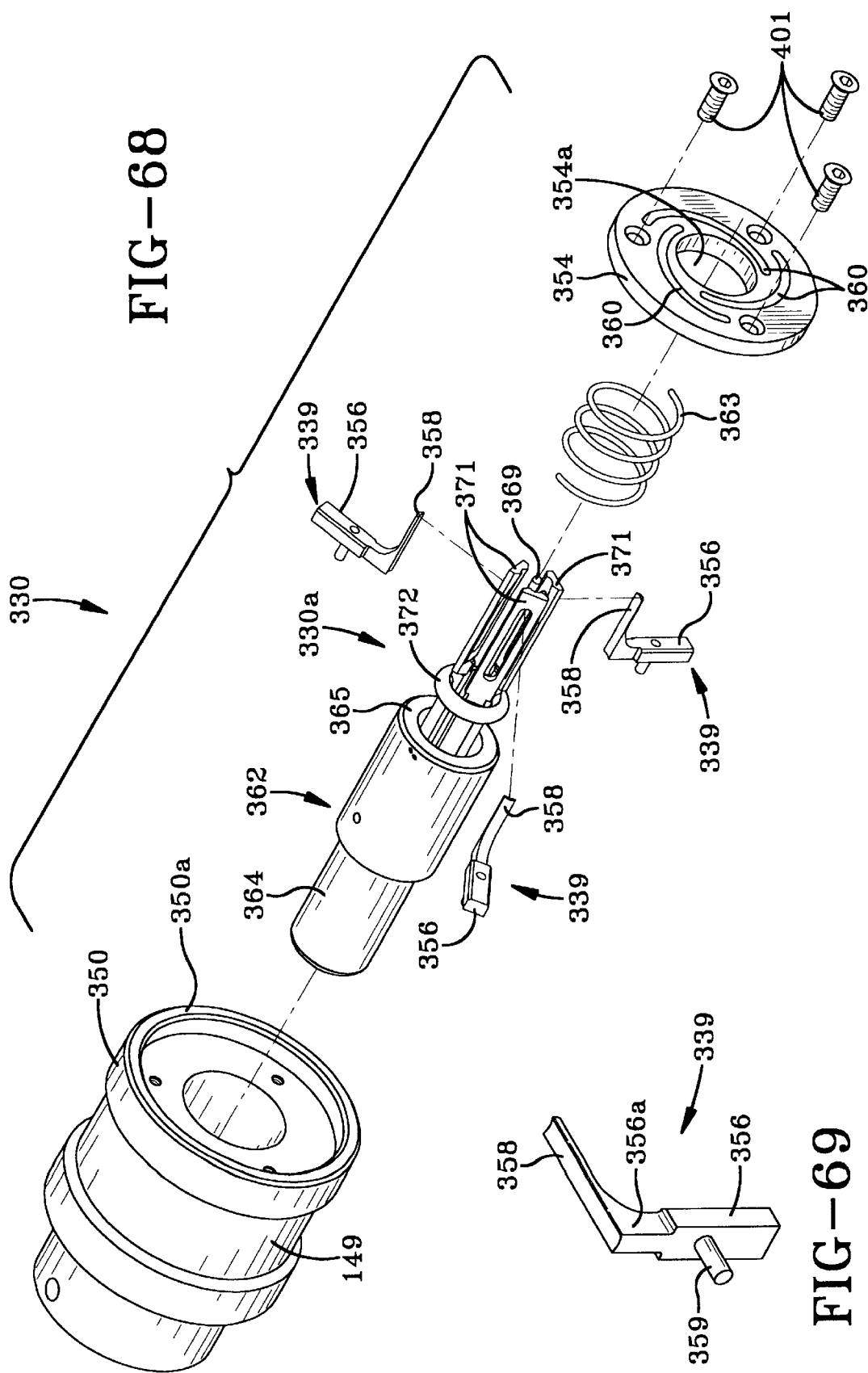
FIG. 68 is an enlarged exploded perspective view of all the components of the subassembly identified by reference character 330 in FIG. 64 with the components shown in FIG. 67 already assembled together.

The combination of the sub-assembly 330 with spreader finger elements 339, as seen in exploded view in FIG. 68, together with the cover plate 347 and the control ring 357, when mounted in the body portion 341 comprises a mechanical means for assembling a tubular segment with a length of tubing. Moreover, an integral part of the sub-assembly positioned concentrically and reciprocably within the mechanical means for assembly constitutes means for ejecting an assembly of a tubular segment with a length of tubing as will be further described herein.

The means for assembly which includes mechanical means for spreading and retracting the spreader finger elements 339 is described in detail below and is comprised primarily of: (1) a substantially cylindrical rotatable sleeve 149, that is rotatable in the cylindrical bore 344 of the body portion 341 of the apparatus; (2) a control ring 357 for rotating the rotatable sleeve 149; (3) a disc-like member 354 having radially, i.e., spirally, extending spiral guideways 360 formed therethrough and being mounted co-axially upon a first end of the rotatable sleeve 149 in an annular recess; and (4) at least three spreader finger elements, indicated generally by the numeral 339, that are supported by a combination of the disc-like member 354 and a cover plate 347 and radially spread or retracted by co-action of the disc-like member and the cover plate with the spreader finger elements.

Figure 65:
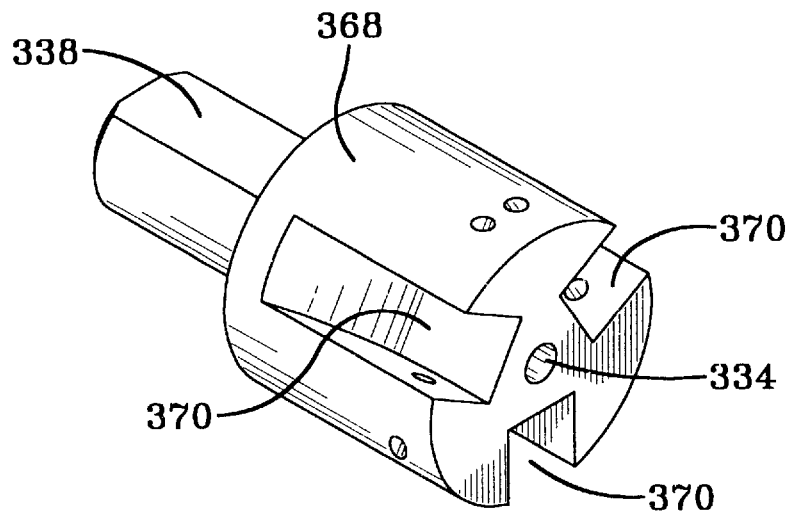
FIG. 65 is a greatly enlarged perspective view of an ejector block which may be used as a part of a sub-assembly identified by reference character 330 in FIG. 64.
Figure 66:
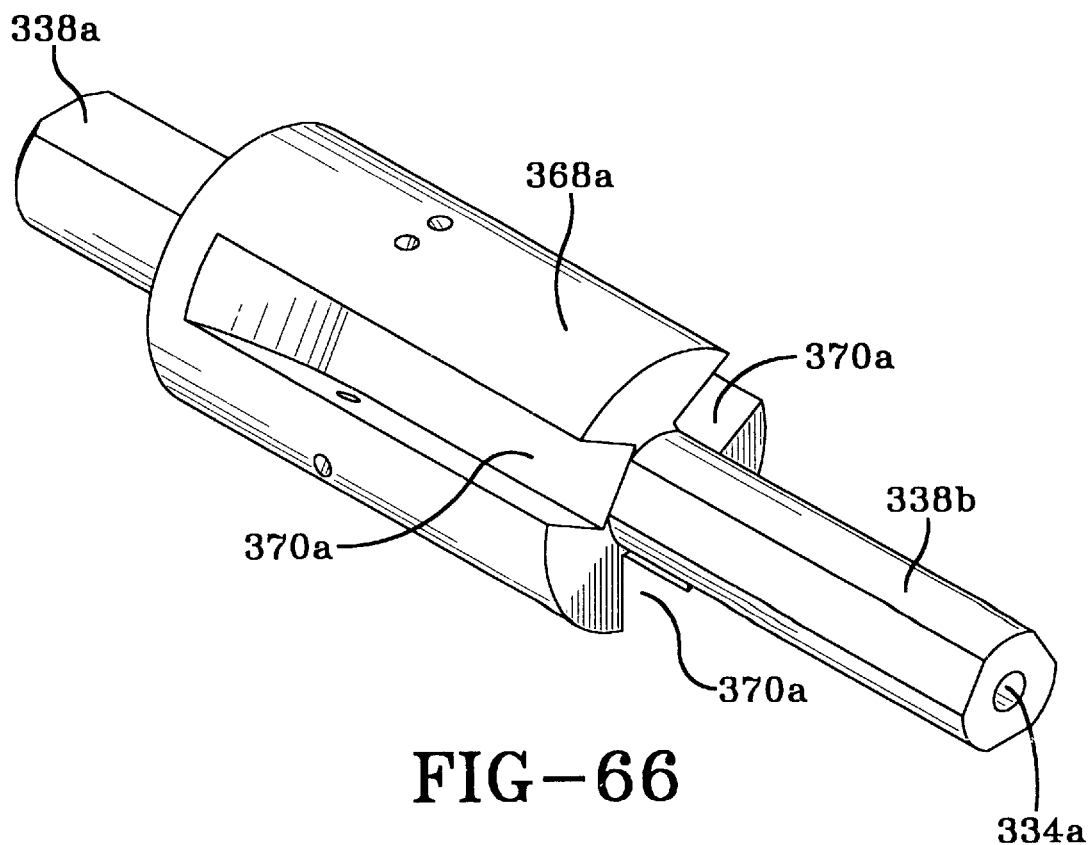
FIG. 66 is a greatly enlarged perspective view of another ejector block which may be used in a modification of the subassembly identified by reference character 330 in FIG. 64.

The ejector means comprise: (1) a reciprocable piston 362, depicted in FIGS. 67 and 68 as part of the assembly apparatus shown in differing stages of the assembly process;

2) an ejector block 368 or 368a as depicted in FIGS. 65 and 66; and (3) ejector arms 371, in addition to the rotatable sleeve 149 in the cylindrical passageway of which the piston 362 is reciprocable.

The subassembly identified by reference character 330 in FIGS. 64, 68, 70 and 71, includes the substantially cylindrical rotatable sleeve 149 with a cylindrical passageway extending therethrough and into which the reciprocable piston is positioned co-axially, indicated generally by the numeral 362. The reciprocable piston has a recess in one end into which there is positioned co-axially an ejector block such as ejector blocks 368 and 368a depicted in FIGS. 65 and 66. The ejector block has a plurality, in this example three, longitudinal slots 370 therein and on which are pivotally mounted, using pins 371b, ejector arms 371 substantially parallel to the longitudinal axis of the piston 362, bearing in mind that when the assembly apparatus is fully assembled, the piston is co-axial with the bore 344 through the body portion 341.

In a recess in the first end 365 of the piston 362 there is mounted in any suitable manner an ejector block 368, such as the ejector block shown in FIG. 65. The ejector block shown in FIG. 65 has a rearwardly extending tongue-like portion 338 that fits into a complementary borehole or passageway 336 in the piston 362 and is secured by a setscrew 337. The overall longitudinal length of the ejector block used in the assembly apparatus determines the distance from the end of the length of tubing where the tubing segment will be emplaced during the assembly process.

In assembling a pinch valve element with two tubular segments as end portions it is necessary to assemble each tubular end portion with a given length of tubing in a separate operation in which an assembly apparatus is used with an ejector block having the appropriate length. Thus a shorter ejector block such as that shown in FIG. 65 would be used to emplace the first tubular segment, e.g. 82, while a longer ejector block 368a, as shown in FIG. 66, would be used in assembling the second tubular segment, e.g. 83, with the length of tubing to get the proper positioning of the tubular segments and achieving also the proper spacing longitudinally along the flexible tubing between the tubular segments. The ejector block 368a is provided with a forwardly projecting axial extension 338b that has a large enough cross-section to serve as a stop for the length of tubing, but is small enough to facilitate use of the coil spring 363 to make the piston 362 recoil after the ejection step.

In assembling the present apparatus the subassembly 330 seen in FIG. 64 is made up by selecting an ejector block 368 (or alternatively ejector block 368a of FIG. 66) of suitable dimensions, such as the ejector block depicted in FIG. 65, and positioning a plurality of pivotal ejector arms 371 in respective slots 370 formed in the sides of the ejector block 368 where the ejector arms are pivotally retained by pins 371a that pass through the walls of the slots and through the ejector arms near a first end 333 of each arm. The number of ejector arms 371 and complementary slots 370 employed is preferably at least three to match the number of spreader finger elements 339. The ejector arms 371 are oriented substantially parallel to the axis of the ejector piston 362. The rearward projecting tongue-like portion 338 of the ejector block 368 is inserted into the axial borehole 336 in the end 365 of the piston 362 and secured with a set screw as shown in FIG. 63.

Referring now to FIGS. 63 and 68, an elongated central guide rod 369 is inserted into and secured in any suitable manner in a longitudinal axial borehole 334 in the free end of the ejector block 368, or, in a longitudinal axial borehole 334a of the axial extension 338b of ejector block 368a if the longer extension block is part of the subassembly.

Turning again to FIGS. 67 and 68, an elastic annular member 372, which may be a conventional "O"-ring, is placed around the ejector arms 371 at about mid-length, for example at notches 335 in the arms, to retain them clustered together around the spreader finger portions 358 in the final assembly.

Figure 69:
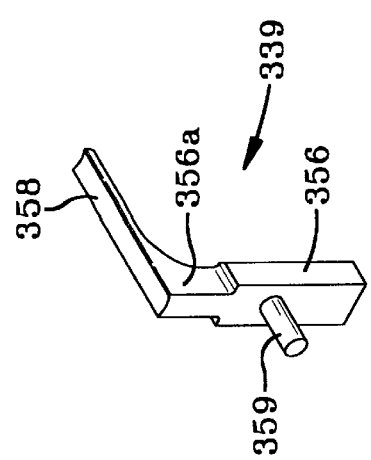
FIG. 69 is a greatly enlarged perspective view of an "L"-shaped spreader finger element showing the guide pin extending laterally from the leg portion.
Figure 71:
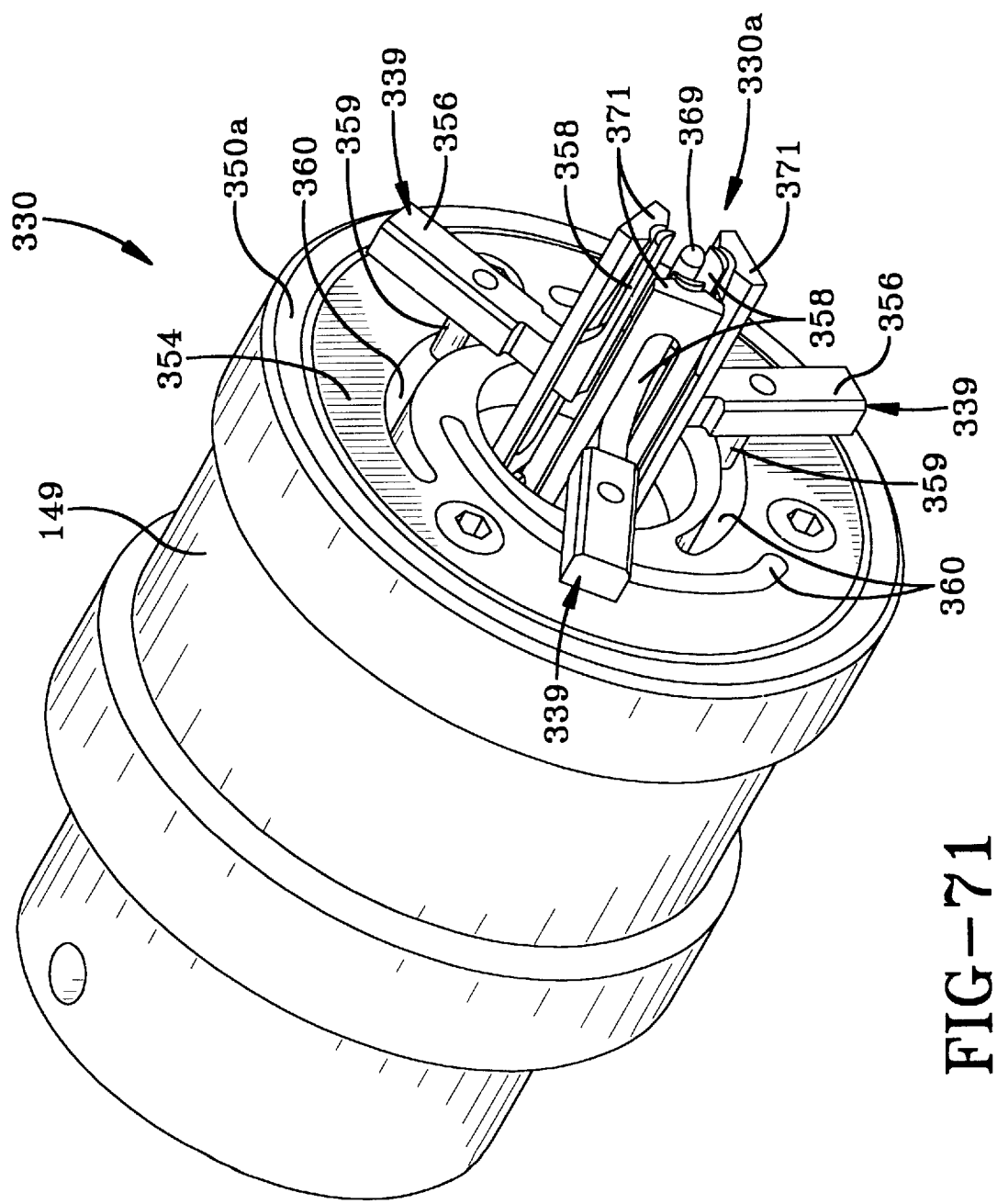
FIG. 71 is a very greatly enlarged perspective view of the sub-assembly identified by reference character 330 in FIG. 64.

Adjacent the second end 332 of each of the ejector arms 371 is an elongated longitudinally extending slot 373 formed therethrough. Through each of the slots 373 a respective leg portion 356 of a spreader finger element 339 extends radially outward from the line of the axis of the piston 362. As seen in FIGS. 68, 69 and 71, the spreader finger elements 39 are "L"-shaped, each with a leg portion 356 and a thin finger, i.e., finger portion, 358. To accommodate reciprocal movement of the ejector arms 371 along the axial line during an ejection step without interfering with the normal function of the spreader finger elements 339, the leg portion 356a that joins the finger portion 358 to the leg portion 356 in each element is preferably made thin enough so that the sides of the slot 373 do not bind against the leg portion 356a.

The means for assembling a tubular segment telescopically upon a length of tubing form part of the subassembly 330, which includes the spreader finger elements 339. The mechanical means for radially spreading the spreader finger portions include the disc-like member 354 as well as the rotatable sleeve 149 on which the disc-like member 354 is mounted. The cover plate 347 with its radial channels 355, while not part of the subassembly 330, is also an essential part of the mechanical means for spreading and retracting the spreader finger portions in cooperation with the disc-like member 354 and its spiral guideways 360.

As best seen in FIG. 69, each spreader finger element 339 is provided with a guide pin 359 that extends laterally from about mid-length of the leg portion 356 so as to extend into a spiral guideway 360 of the immediately adjacent disc-like member 354. With the spreader finger elements 339 restricted by the radial channels 355 of the cover plate 347 so that they cannot rotate, rotation of the disc-like member 354 provides cam-like action as the guide pins 359 are forced to slide along the respective spiral guideways 360, moving the spreader finger elements 339, and their finger portions 358, radially outward or inward, depending on the direction of rotation.

Figure 70:
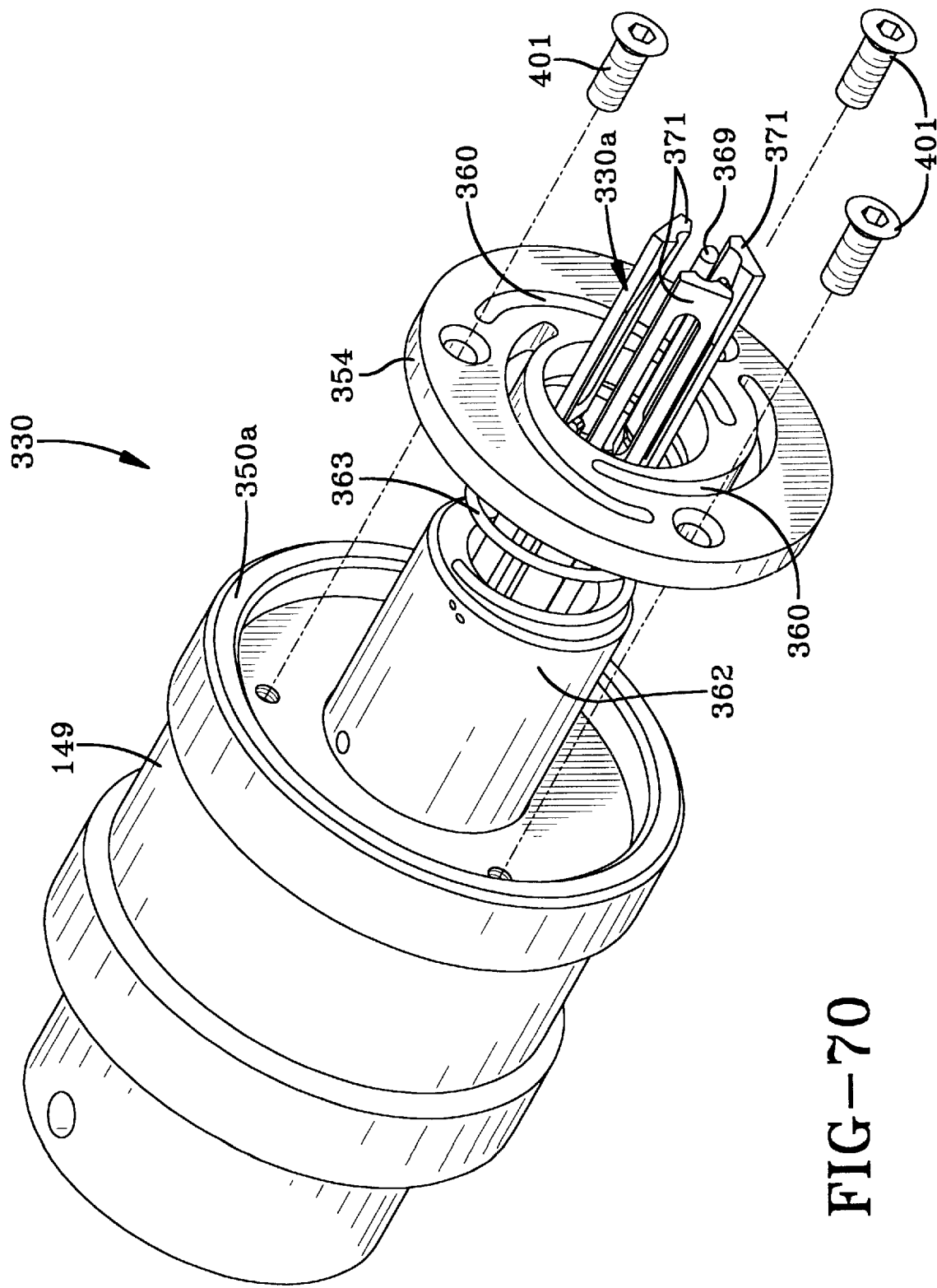
FIG. 70 is a very greatly enlarged partly exploded perspective view of the sub-assembly identified by reference character 330 in FIG. 64 in the process of being assembled.

In further assembling the subassembly 330 of FIG. 64, as seen in FIG. 70, a coil spring 363 is slid over the cluster of ejector arms 371, followed by the disc-like member 354 preparatory to attaching it as by threaded fasteners 401 to the annular end face of the rotatable sleeve 149, after sliding the piston 362 further into the passageway of the rotatable sleeve 149, as seen in FIG. 71. Also seen in FIG. 71 are the spreader finger elements 339 positioned with the finger portions 358 clustered concentrically inside the cluster of ejector arms 371 and around the central guide rod 369.

Figure 72:
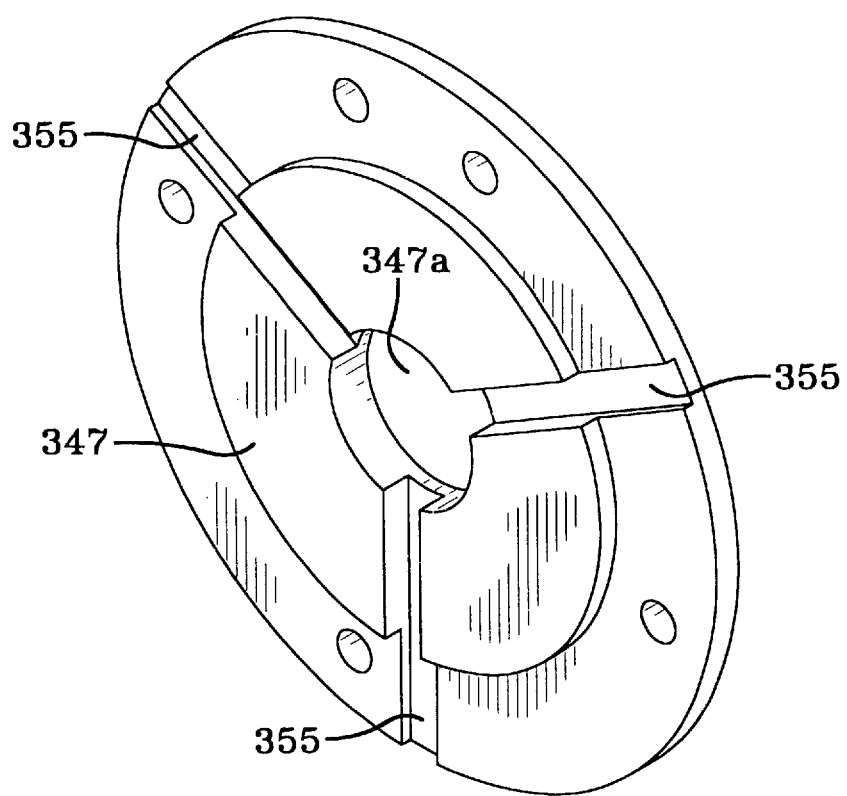
FIG. 72 is a perspective view of the reverse or inside face of the cover plate.

The subassembly 330 seen in FIG. 64 and largely contained within the rotatable sleeve 149 can now be inserted into the body portion 341 from the first or front side 345 thereof into the bore 344 and partially extending beyond the second or rear side 346 of the body portion 341 and positioned as seen in FIG. 63, so that the cover plate 347 can be attached by threaded fasteners 402, preferably using a locating pin 404 to align the grooves in the back side of the cover plate (described below) in the required operative orientation. The inside face, i.e. the back side, of the cover plate 347, as seen in FIG. 72, is formed with radial channels 355 in which the respective leg portions 356 of the spreader finger elements 339 are reciprocable when positioned therein with the cover plate attached with the inside face turned face to face with the disc-like member 354. The radial channels 355 formed in the inside face of the cover plate 347 and with the leg portions 356 of spreader finger elements 339 postioned therein are, of necessity, open toward the disc-like member 354 so the guide pins 359 can extend into, and slide along, the spiral guideways 360.

Referring again more particularly to FIGS. 63 and 64, the body portion 341 is seen to encompass the cylindrical bore 344, which is of relatively large diameter compared to the body portion, and extends from the first surface or side 345 to the second surface or side 346 of the body portion. While the assembly apparatus is shown in the drawing figures supported upon a base with the assembly apparatus oriented to receive an end portion of the length of tubing disposed substantially horizontally during the assembly procedure, it is to be understood that the base may be modified, if desired, to support the apparatus with the bore tilted upwardly at any angle to receive the length of tubing, including facing substantially vertically upward, without departing from the scope of the invention. In such event the first or front side of the apparatus as here described would be the upper or top side or surface and the second or back or rear side would be the lower or bottom side or surface of the assembly apparatus.

The first surface 345 of the body portion 341 is substantially covered by the circular cover plate 347 with an aperture 347a located at the center thereof, while the second surface 346 of the body portion 341 is faced with a first retainer ring 352 that has a slightly smaller inner diameter than the diameter of the cylindrical bore 344. The cover plate 347 and the first retainer ring 352 are fastened to the body portion 341, for example, by screws 402, 405, respectively, but it is to be understood that any suitable means of retaining these components in their relative operable positions may be employed.

As best shown in FIGS. 63 and 64, within the cylindrical bore 344, as indicated above, is a rotatable substantially cylindrical sleeve or tube 149, having a first end 350 and a second, smaller, end 351. The rotatable sleeve 149 is retained in the cylindrical bore 344 by a flange or shoulder 353 of the rotatable sleeve which mates with, or fits against, the radially inner portion of the first retainer ring 352 in the vicinity of the second surface 346 of the body portion 341 and a radially outer, forwardly projecting, flange portion 350a of the first end of the rotatable sleeve is retained by the cover plate 347. While the first end portion 350 of the rotatable sleeve 149 has a larger outer diameter than the second end portion 351, hence the flange or shoulder 353, the inside diameter of the cylindrical passageway through the rotatable sleeve is uniform, and the rotatable sleeve will be referred to herein as substantially cylindrical. The second end 351 of the rotatable sleeve 149 is disposed outside of the cylindrical bore 344 and the first retainer ring 352 and is concentrically surrounded by a rotatable control ring 357, preferably of slightly greater diameter than the first retainer ring 352 and preferably having a knurled perimeter surface and/or a lever 361 extending therefrom for easy manipulation. The control ring 357 is bolted or otherwise attached in any suitable manner to the rotatable sleeve 149.

The first end 350 of the rotatable sleeve 149 has a recessed annular end face, having a perimeter flange 350a, as indicated. In the annular recess radially inward from the flange 350a is fitted the disc-like member 354 that is bolted or otherwise fixedly attached to the end face and has a central aperture 354a the same diameter as the central aperture 347a of the cover plate 347, but slightly smaller than the inner diameter of the passageway through the rotatable sleeve 149. The rotatable disc-like member 354 has one face contacting the face of the annular recessed end of the rotatable sleeve 149 to which it is attached and the opposing face is face to face with and rotatable against the inside face of the front cover plate 347, which is attached to the body portion 341 and not rotatable.

As seen in FIGS. 79 and 81 in dotted outline and in perspective in FIG. 72, the reverse side of the cover plate 347 is provided with three equiangularly-spaced channels 355 which are open sided towards the disc-like member 354 and extend radially outwardly from the central aperture 347a of the cover plate. Inserted reciprocably in each radially extending channel 355 from the central aperture 347a is a leg portion 356 of an "L"-shaped spreader finger element indicated generally by the reference numeral 339. The spreader finger portions 358 extend out of the central aperture 347a of the front cover plate 347 substantially parallel to the axis of the bore 344 to form a cluster and it is this cluster that is manipulated radially apart to spread a tubular segment, such as a tubular segment end portion of a pinch valve element, to permit telescopic assembly thereof upon, i.e., concentrically with, a length of tubing. The spreader finger portions 358, upon which tubular segments are placed for spreading, i.e., stretching to a larger cross-sectional opening, during telescopic assembly of a flexible tubular segment with a length of tubing according to the invention, are preferably quite thin for easier removal of the assembled tubular segment and tubing combination from the assembly apparatus. In this regard it should be noted that the spreader fingers 358 are sandwiched between a tubular segment end portion 82, 83 of the pinch valve element and the tubing 49 when the spreader fingers are retracted prior to the ejection step.

In FIGS. 68, 70 and 71, the disc-like member 354 is shown to have formed therein three parallel and radially, i.e. spirally, outward extending spiral guideways 360 which are open-sided towards the cover plate 347. Each spiral guideway extends spirally out in the same direction of rotation from the central aperture 354a of the disc-like member 354. Each leg portion 356 of a respective "L"-shaped spreader finger element 339 is provided with a guide pin 359 fixedly attached thereto that extends laterally from the radial channel 355, of the cover plate 347, in which the leg portion 356 reciprocates, into one of the spiral guideways 360 along which it is slideable. Instead of the spiral guideways shown cut entirely through the disc-like member 354, the guideways 360 may be grooves cut to the same pattern if they are each deep enough to readily receive and slideably guide a guide pin 359 during rotation of the disc-like member 354 and the grooves are open sided towards the cover plate 347.

Upon rotation of the disc-like member 354, using the knurled control ring 357 or the lever 361 to rotate the rotatable sleeve 149 to which the disc-like member 354 is attached, cam-like action is obtained to radially spread or retract the spreader finger portions 358 away from or towards the common axis as the leg portions 356 are moved radially by the respective guide pins 359 sliding in the spiral grooves 360. If desired, the lever 361 may be attached to the control ring 357 as seen in FIG. 64 and used to rotate the control ring 357 through a sufficient arc to obtain the desired spreading and retracting of the spreader finger portions 358.

Positioned in the cylindrical passageway of the rotatable sleeve 149 and extending rearwardly therefrom is the reciprocable piston 362 that reciprocates through a short range of movement within the cylindrical passageway of the rotatable sleeve 149 to carry out the very important ejection procedure. The piston 362 is urged resiliently out of the passageway of the rotatable sleeve 149 by a coil spring 363 that bears at one end of the coil spring against the annular portion of the face of the disc-like member 354 that extends radially inward from the central aperture of the rotatable sleeve 149, and at the other end, against the first end 365 of the piston 362. The rear portion 364 of the second end of the piston is of a slightly smaller diameter than the first portion 365, the rear end of the larger diameter portion constituting a shoulder on the piston, and the second retainer ring 366 attached to the control ring 357 has a central aperture smaller enough than the larger diameter of the first end portion 365 of the piston to catch the shoulder and limit the reciprocation of the piston 362 in the rearward direction.

Mounted in a recess 336 in the face of the first end 365 of the piston 362 is an ejector block 368 that is dimensioned longitudinally to serve as a stop to accurately limit the depth of insertion of a length of tubing on which a tubular segment, such as a pinch valve element, is to be emplaced.

Figure 84:
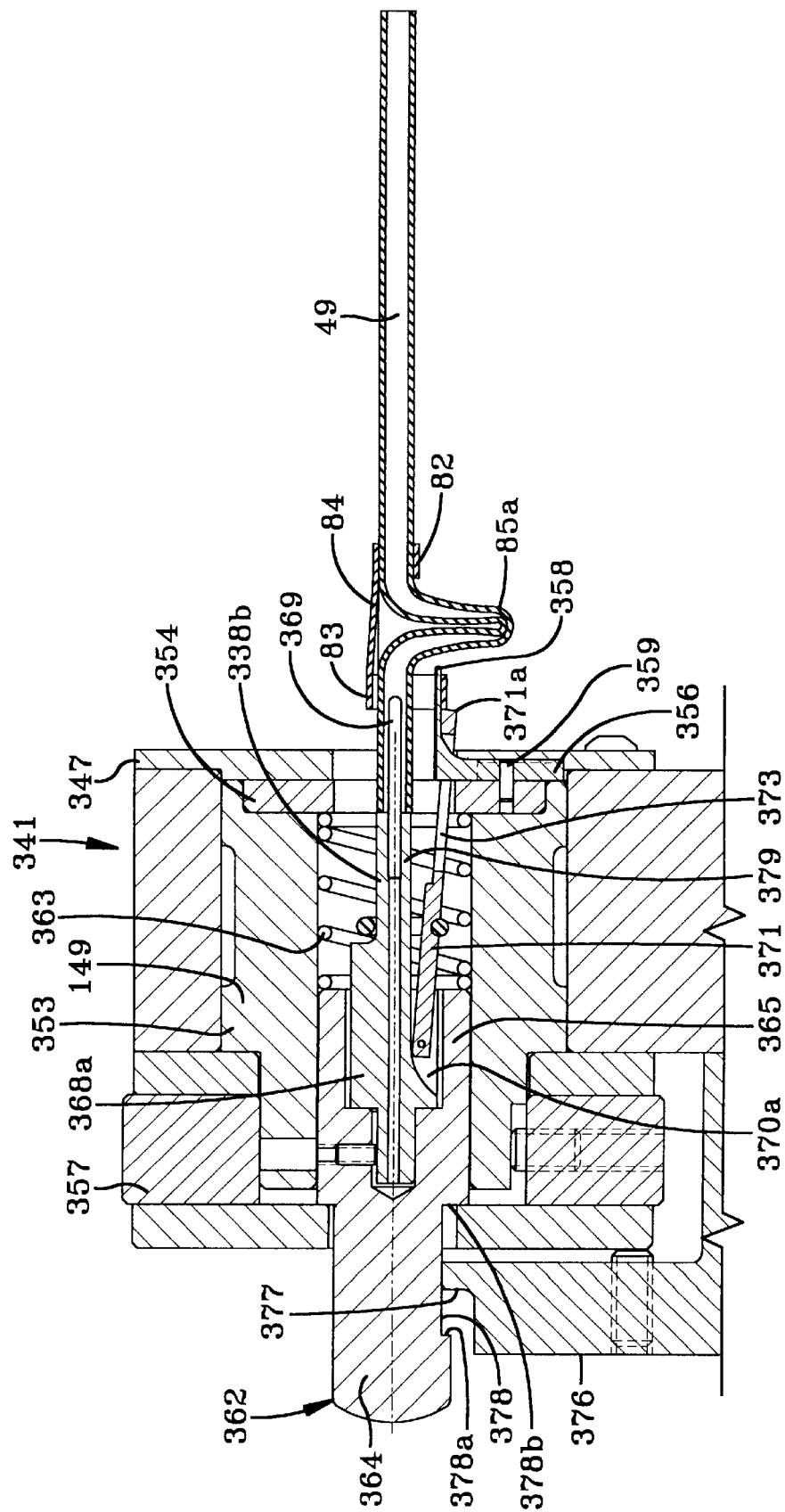
FIG. 84 is a fragmentary view in section of the assembly apparatus and stretched second tubular segment end portion of the pinch valve element shown in FIG. 83, and with the length of tubing inserted into the apparatus over the central guide rod and through the cluster of spreader fingers.
Figure 85:
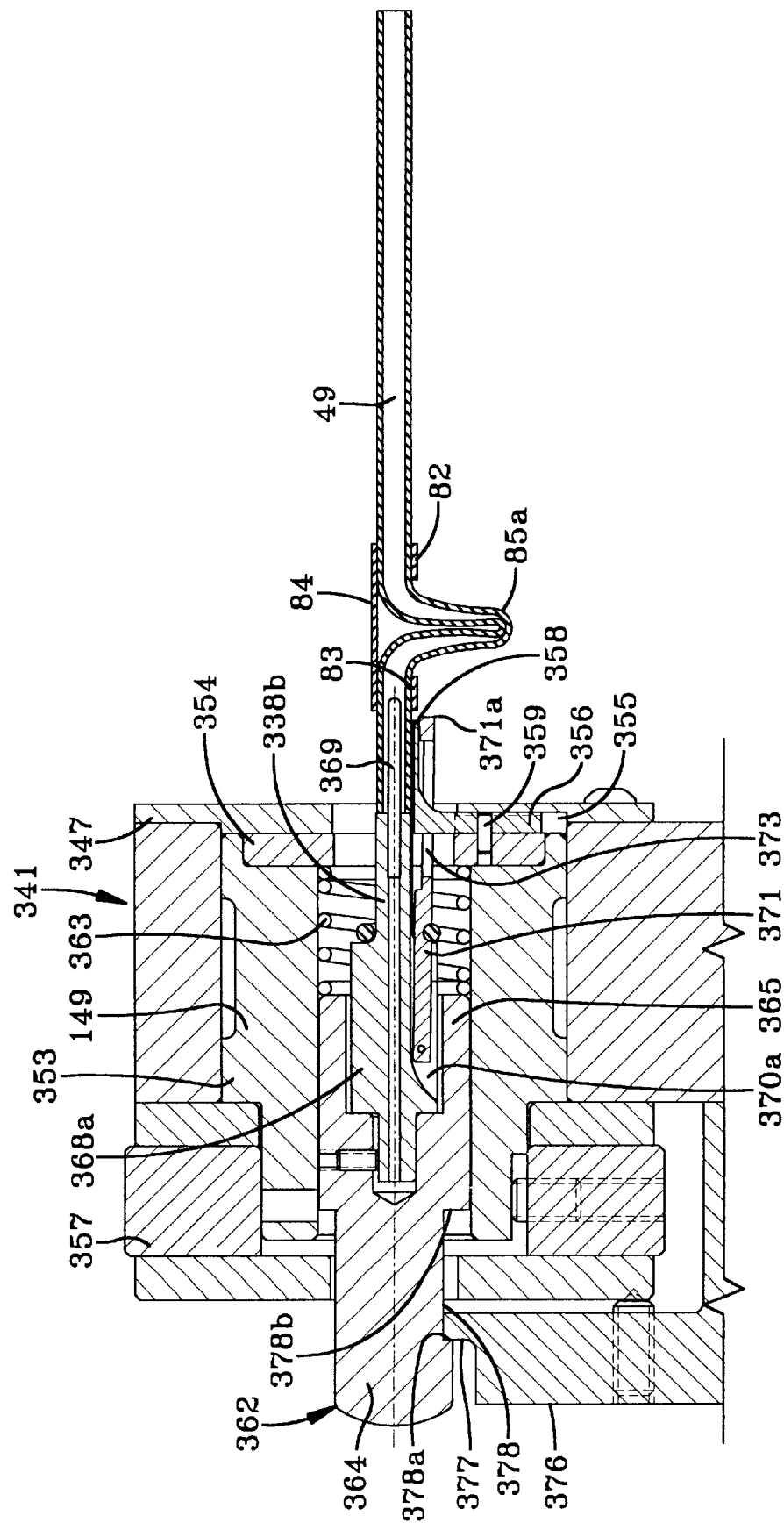
FIG. 85 is a fragmentary view in section of the assembly apparatus with the second tubular segment end portion of the pinch valve relaxed upon the length of tubing and the ejector piston moved forward.

In FIGS. 84 and 85 there is shown in section an assembly apparatus with an ejector block 368*a* with a longer axial dimension that provides a shallower stop for flexible tubing inserted into the apparatus for the purpose of assembling the second tubular segment end portion of a pinch valve element as a second step in the process of assembling a pinch valve.

A central guide rod 369 extends axially from the ejector block 368 or 368*a* through the passageway of the rotatable sleeve 149 and substantially to the outward ends of the spreader finger portions 358 where it is centered between them. It serves as a guide over which flexible tubing is inserted into the assembly apparatus. Also pivotably mounted are ejector arms 371 that extend forwardly along inside the passageway of the rotatable sleeve 149 and nearly parallel to the common axis and out through the aperture 354*a* in the disc-like member 354 and aperture 347*a* in the cover plate 347 where they each rest against the radially outward surface of a spreader finger portion 358, being collectively resiliently urged against respective spreader finger portions by a springy resilient annular member 372, such as an "O" ring. The ejector arms 371 must be selected to be of the appropriate length to contact and bear against the edge of a flexible tubular segment, such as a tubular end portion of a pinch valve element, that has just been emplaced on a length of flexible tubing extending into the apparatus, simultaneously with contact and pressure between the ejector block and the inner end of the flexible tubing within the apparatus, in order to avoid moving or displacing the tubular end portion longitudinally of the flexible tubing during ejection. Because of the elastic radially inward tension of the tubular end portions of the pinch valve element upon the flexible tubing, which has an outer diameter as great or greater than the inner diameter of the tubular segments, it is not practically feasible to remove the assembled pinch valve from the spreader fingers, without risking altering of the positions of the tubular segment end portions of the pinch valve element, unless use is made of the ejection components of the apparatus.

The second part 364 of the reciprocable ejection piston 362 is shown in FIGS. 60 and 63 to be supported by a support element 374 having a lower section 375 thereof attached to the rear of the base portion 342 of the assembly apparatus and an upright leg portion 376 extending upwardly to contact the rear part 364 of the piston which is slideable on the flanged upper end 377 of the leg portion 376. A section 378 of the underside of the rear part 364 of the piston 362 is ground flat from adjacent the second end to the larger diameter forward part 365 of the piston 362, and it is this flat section that rests upon the flanged upper end 377 of the leg portion 376 of the support element 374. The flat nature of the underside section 378 serves to prevent the piston 362 from rotating during use, and the shoulders 378*a*, 378*b* formed at each end of the flat section 378 catch, respectively, on the flanged upper end 377 of the support element 374 and on the second retainer ring 366 to provide respective stop actions in the reciprocal motion of the piston 362.

The base, body portion, and parts such as the cylindrical sleeve, reciprocable piston, control ring and both retainer rings, cover plate and disc-like member, of the assembly apparatus may be made of mild steel or of an easily machinable metal, such as aluminum alloy, if desired, but are preferably made of tool steel or stainless steel. Preferably the spreader fingers and the ejector arms are made of tool steel or stainless steel to provide greater strength and durability in the thinner members.

In manufacturing a tension responsive pinch valve of the sort defined herein, it is essential to the proper valving action of the pinch valve that the tubular segment end portions of the pinch valve element be positioned with some accuracy spaced apart a rather short interval longitudinally, i.e., linearly, of the length of tubing, with the magnitude of the interval or spacing being substantially greater than the length of the shank of the pinch valve element. Such larger spacing linearly along the tubing is essential in order to obtain a doubling over of the tubing that produces a pinching shut of the embraced portion of the tubing when there is no tension on the portion of the length of tubing that includes the pinch valve per se and the shank of the pinch valve element tends to elastically assume about its normal length, drawing the attached tubular segment end portions mutually closer. Proper spacing during telescopic assembly is readily achievable in a convenient, efficient way using two nearly identical embodiments of the assembly apparatus described herein differing primarily in having ejector blocks of differing appropriate lengths to assemble the respective tubular segments. The ejector blocks serve as stops in indexing the length or extent of the end of the length of flexible tubing that can extend into the assembly apparatus during the assembly process, thus controlling the positioning of the tubular segment end portions.

Figure 67:
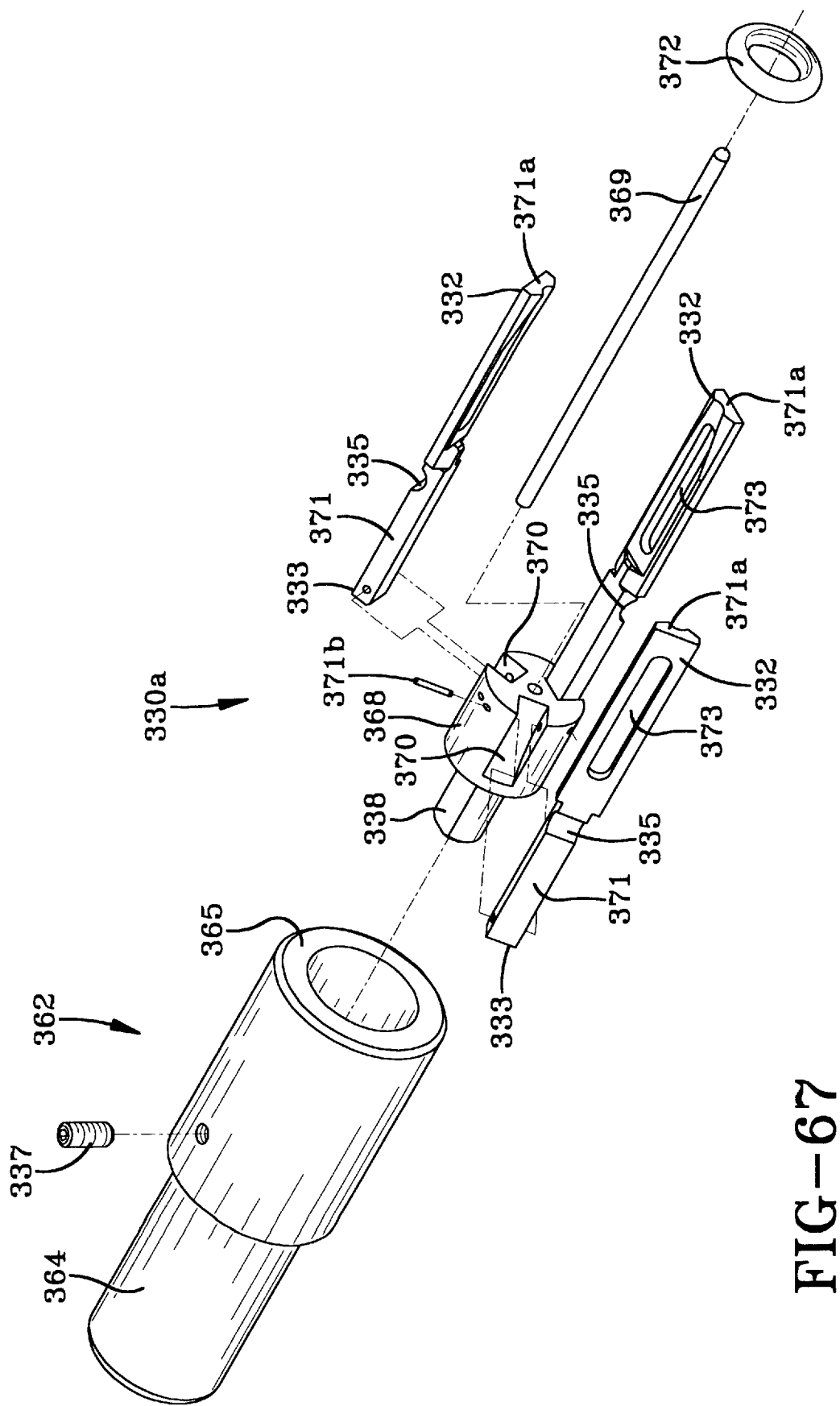
FIG. 67 is an enlarged exploded perspective view of some of the components of the subassembly identified by reference character 330 in FIG. 64, including the ejector block of FIG. 65.

The first embodiment of the assembly apparatus utilized will have a relatively short ejector block, such as that identified by the reference numeral 368 in FIGS. 63 and 67 and shown in perspective view in FIG. 65, so that the end of the length of tubing will extend relatively deep into the assembly apparatus and the first tubular segment end portion of the pinch valve element will be emplaced far enough from the inserted end of the flexible tubing to leave room for the positioning of the second tubular segment end portion. The telescopic assembly of the second tubular segment end portion can only be performed closer to the inserted end of the length of tubing, using the assembly apparatus, than the location of the emplacement of the first tubular segment end portion.

The second embodiment of the assembly apparatus used to telescopically assemble the second tubular segment end portion must have a longer ejector block such as that identified by the reference numeral 368*a* in FIGS. 84 and 85 and shown in perspective view in FIG. 66, so that the flexible tubing will be stopped at a shallower depth for the assembly of the second pinch valve tubular segment end portion closer to the end of the length of flexible tubing than the first tubular segment end portion. The ejector block 368a may be seen in FIG. 66 to have a smaller diameter extension 338b that serves as the actual stop within the assembly apparatus for the end of the length of tubing inserted during assembly operations. The extension 338b has a smaller diameter than the ejector block 368a in order to leave circumferential annular space within the rotatable sleeve 149 for the coil spring 363.

Figure 73:
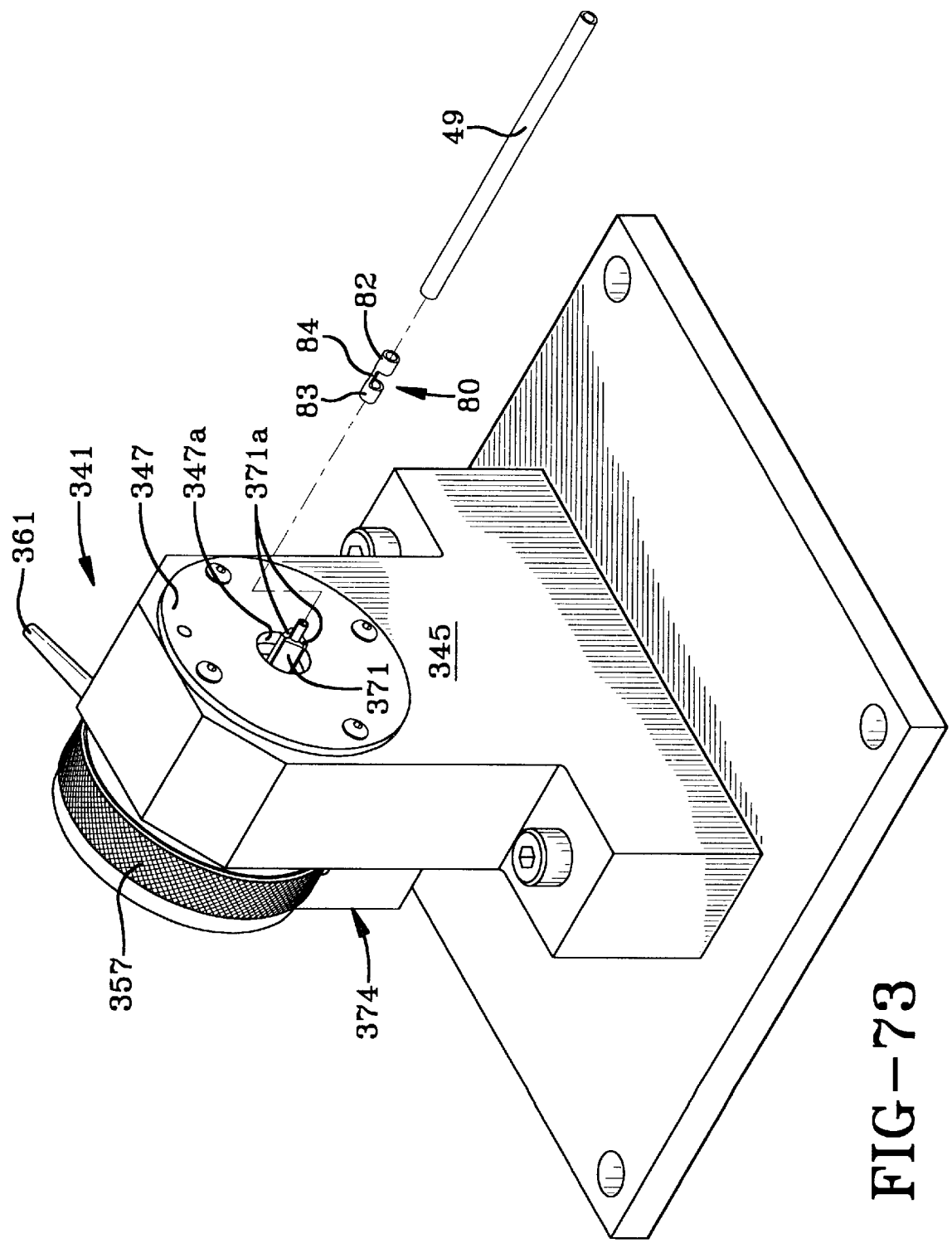
FIG. 73 is a perspective view of the assembly apparatus with the components of a pinch valve shown in exploded view relationship about to be assembled using the assembly apparatus.

Referring now to FIG. 73 there is depicted an embodiment of the assembly apparatus, along with a flexible pinch valve element 80 and a length 49 of flexible tubing of the same diameter depicted in exploded view. The pinch valve element 80, which consists of first 82 and second 83 foreshortened tubular segments as end portions joined by a short shank portion 84 of about the same length as the end portions, is about to be telescopically assembled on the length 49 of flexible tubing near an end thereof. The embodiment of the assembly apparatus shown in FIG. 73 is to be understood to be equipped with an ejector block 368 of appropriate length for positioning the first tubular segment 82 of the pinch valve element 80.

Figure 74:
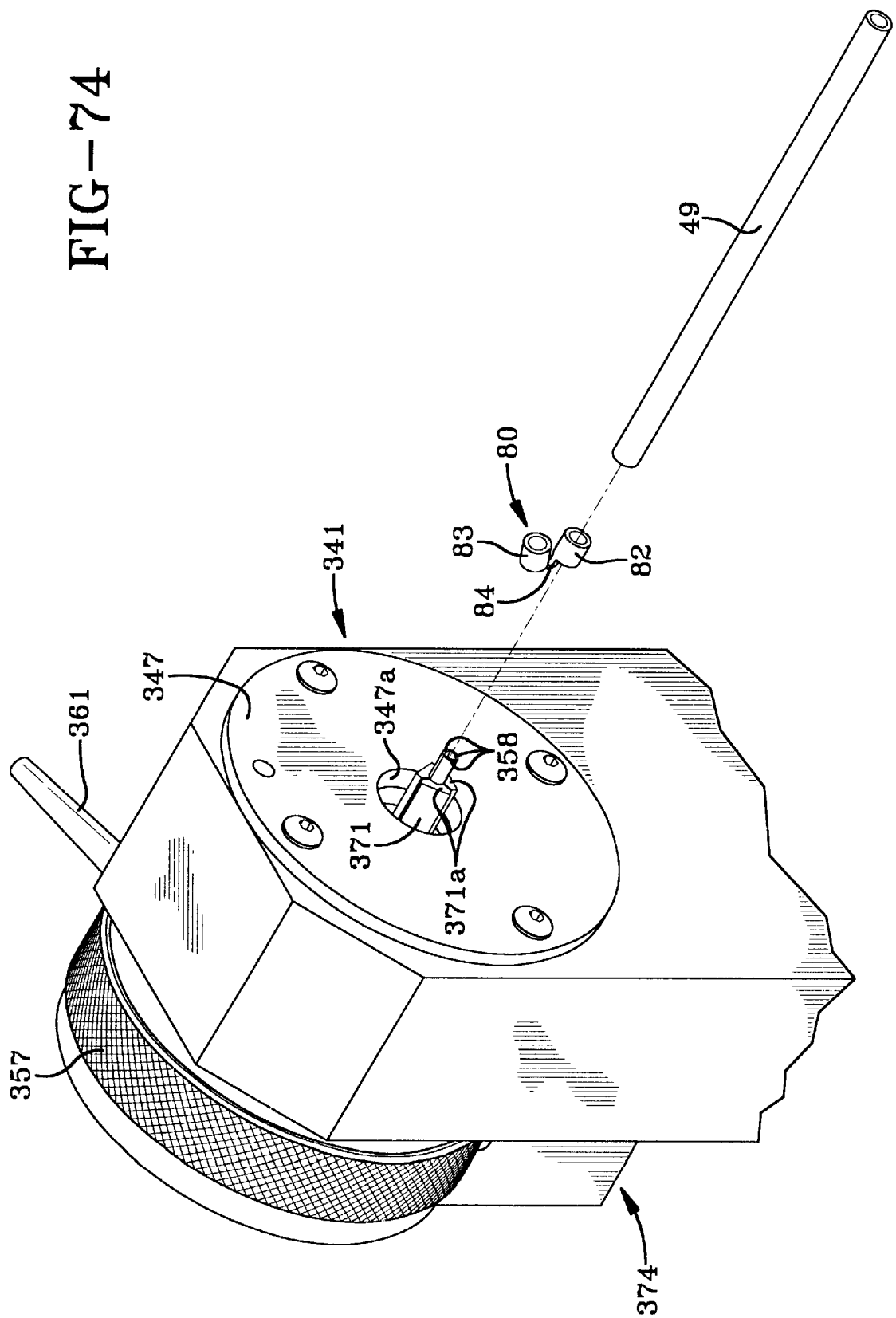
FIG. 74 is a fragmentary perspective view of the assembly apparatus shown with a first tubular segment end portion of the pinch valve element oriented for placing over, i.e., around, the fingers of the spreader finger elements.
Figure 75:
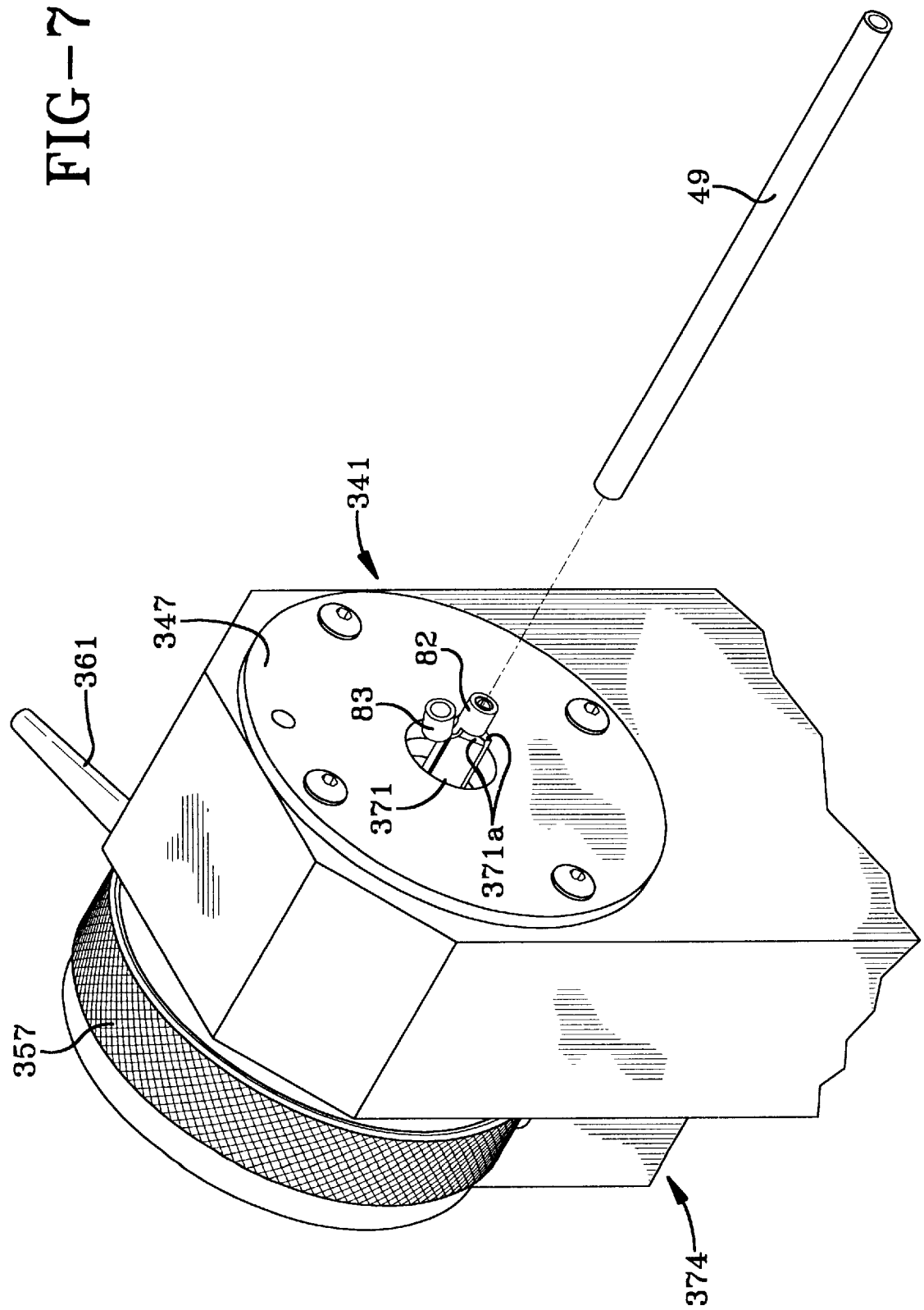
FIG. 75 is a view similar to FIG. 74 with the first tubular segment end portion of the pinch valve element slid onto the cluster of spreader fingers to commence the assembly process.
Figure 76:
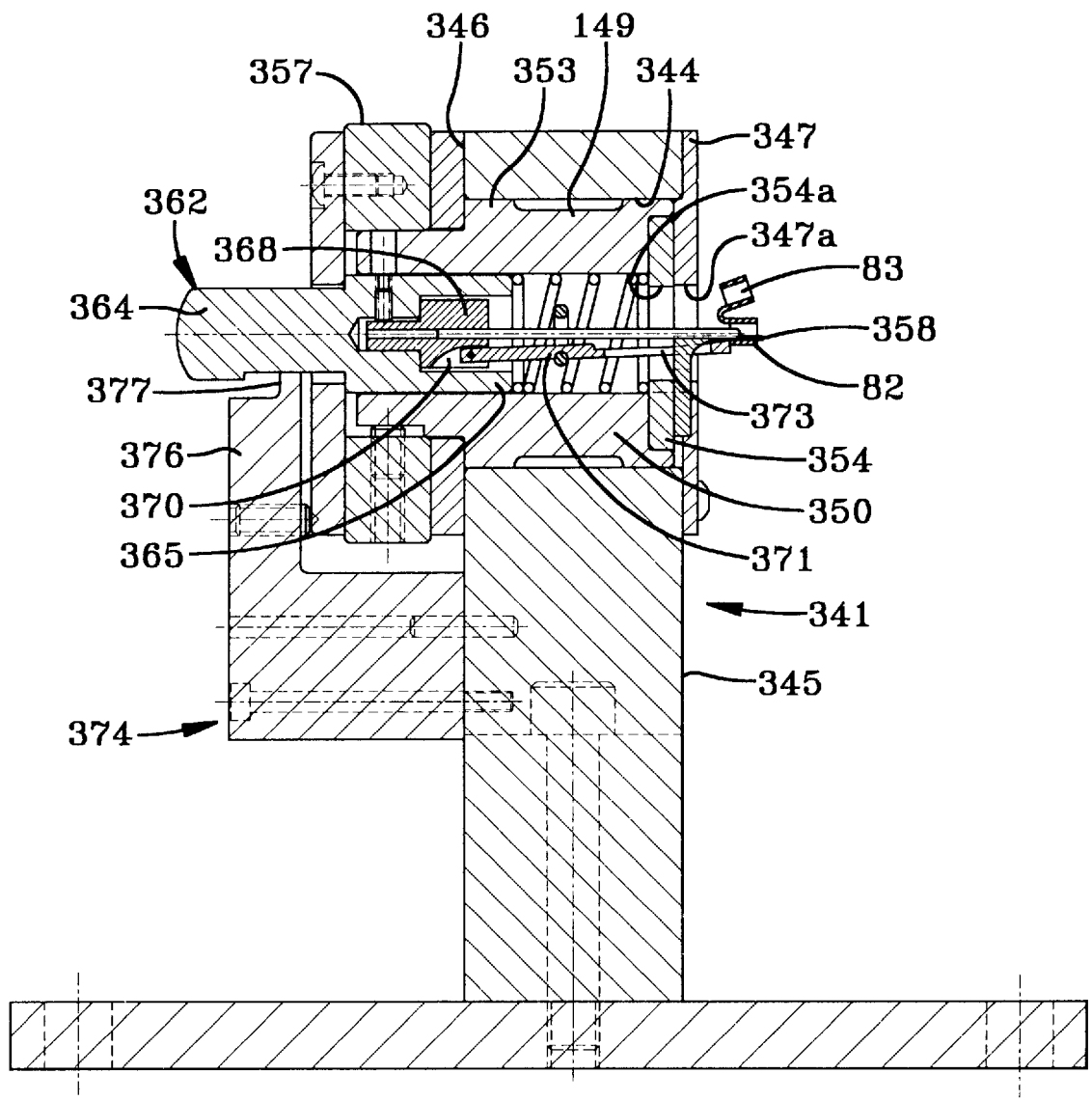
FIG. 76 is a view in vertical section of the assembly apparatus like that shown in FIG. 63, but with a first tubular segment, namely a tubular end portion of the pinch valve element, emplaced over the spreader fingers as in FIG. 75.

The pinch valve element 80 is seen in FIG. 74 to be poised for assembly on the length 49 of flexible tubing with the shank portion 84 of the pinch valve element bent aside to hold the second tubular segment end portion 83 out of the way so the first tubular segment end portion 82 can be slipped over the spreader finger portions 358 that are retracted close together as a cluster as depicted in FIG. 74. In FIG. 75 the tubular segment end portion 82 is shown slipped onto the cluster of spreader finger portions 358. The inner edge of the first tubular segment end portion should be in contact with the ends 37a of the ejector arms 31 to ensure accurate positioning during the assembly process. The section view in FIG. 76 also shows the tubular segment end portion 82 slipped onto the spreader finger portions 358. In FIG. 76 it is also seen that the apparatus is equipped with a fairly short ejector block 368 inside the first end 365 of the ejector piston 362.

Rotation of the control ring 357, which concentrically surrounds and is attached to the rear end of the larger diameter portion of the rotatable sleeve 149, causes rotation of the rotatable sleeve as well as the disc-like member 354 which is mounted on the front end 350 of the rotatable sleeve. Rotation of the disc-like member 354 forces the guide pins 359 attached to respective leg portions 356 of spreader finger elements 339 to slide along the spiral guideways of the disc-like member, giving cam-like action moving the leg portions 356 in a radial direction within the radial channels in the cover plate 347 and the spreader finger portions 358 of the spreader finger elements 339 are consequently moved radially as well, which is the desired action. The direction and extent of rotation of the disc-like member 354 determines the radial direction and extent of movement of the spreader finger portions 358.

Figure 77:
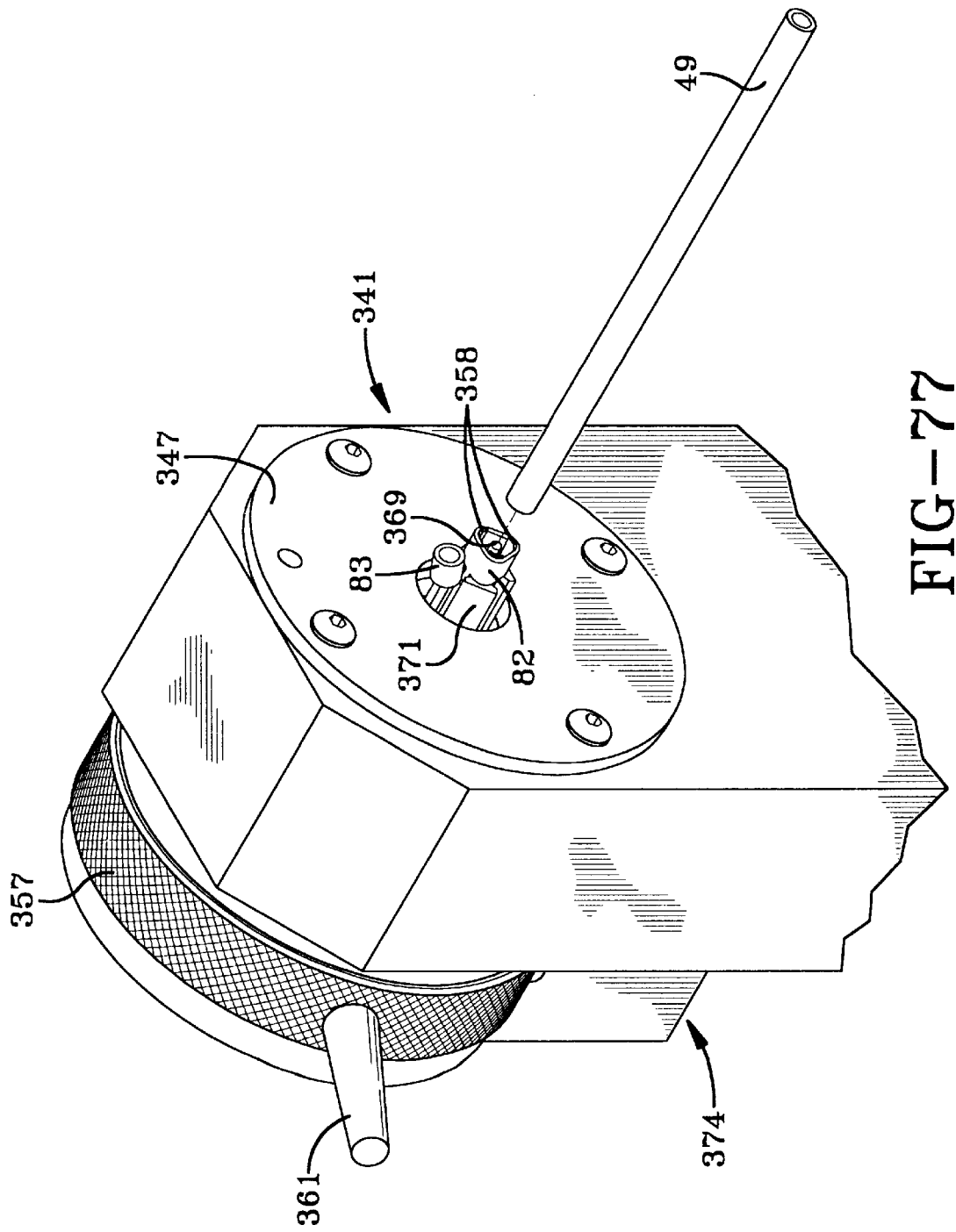
FIG. 77 is a perspective fragmentary view similar to FIG. 75 showing the first tubular segment end portion of the pinch valve element shown in FIG. 75 stretched open radially to receive therethrough the length of tubing upon which the pinch valve element is to be telescopically assembled.

In the next assembly step the control ring 357 is then grasped and rotated manually, or the lever 361 may be used to rotate the control ring 357, in the appropriate direction and through an arc sufficient to spread the spreader finger portions 358, thus stretching the first tubular segment end portion 82 open as shown in FIGS. 77, 78 and 79. Turning the control ring 357 sufficiently stretches the tubular segment 82 enough to admit the end of the length of tubing 49 which is then slid through the tubular segment with little or no friction and onto central guide rod 369 until the end of the length of tubing hits the ejector block 368, which serves as a stop for the proper positioning of the tubular segment end portion 82 on the length of tubing 49.

The control ring 357 is then rotated as by moving the lever 361 back towards its starting position to relax the spreading tension on the first tubular segment end portion 82, completing the assembly step for the first tubular segment end portion.

To carry out ejection, the ejector piston 362 is moved forward (towards the first surface 345 of the body portion 341) by any suitable means against the coil spring 363 to move the ejector piston a small distance or spacing from a position with the second or rear end 364 extending back beyond the support element 374 until the ejector piston 362 reaches a pre-set stop as seen in FIG. 80 where the rear edge 378a of the flattened lower surface 378 of the rear part 364 of the piston is caught by the upstanding flanged upper end 377 of the upright leg section 376 of support element 374. The piston 362 carries forward the ejector block 368 and the ejector arms 371 which contact and eject simultaneously and respectively the end of the length of tubing 49, and the nearest edge of the emplaced tubular segment 82 which is contacted by the ends of the ejector arms 371a, as can be seen in FIGS. 80 and 81. At the pre-set stop the ejector arms 371 and the ejector block 368 will have coordinately mechanically ejected with simultaneous pressure the length 49 of flexible tubing and the emplaced first tubular end portion 82 of the pinch valve element.

While the piston 362 is readily slid forward manually towards the cover plate 347 if the coil spring 363 is selected to be of a suitable spring tension, the piston 362 may be equipped to be reciprocated hydraulically or electromagnetically, if desired.

Figure 82:
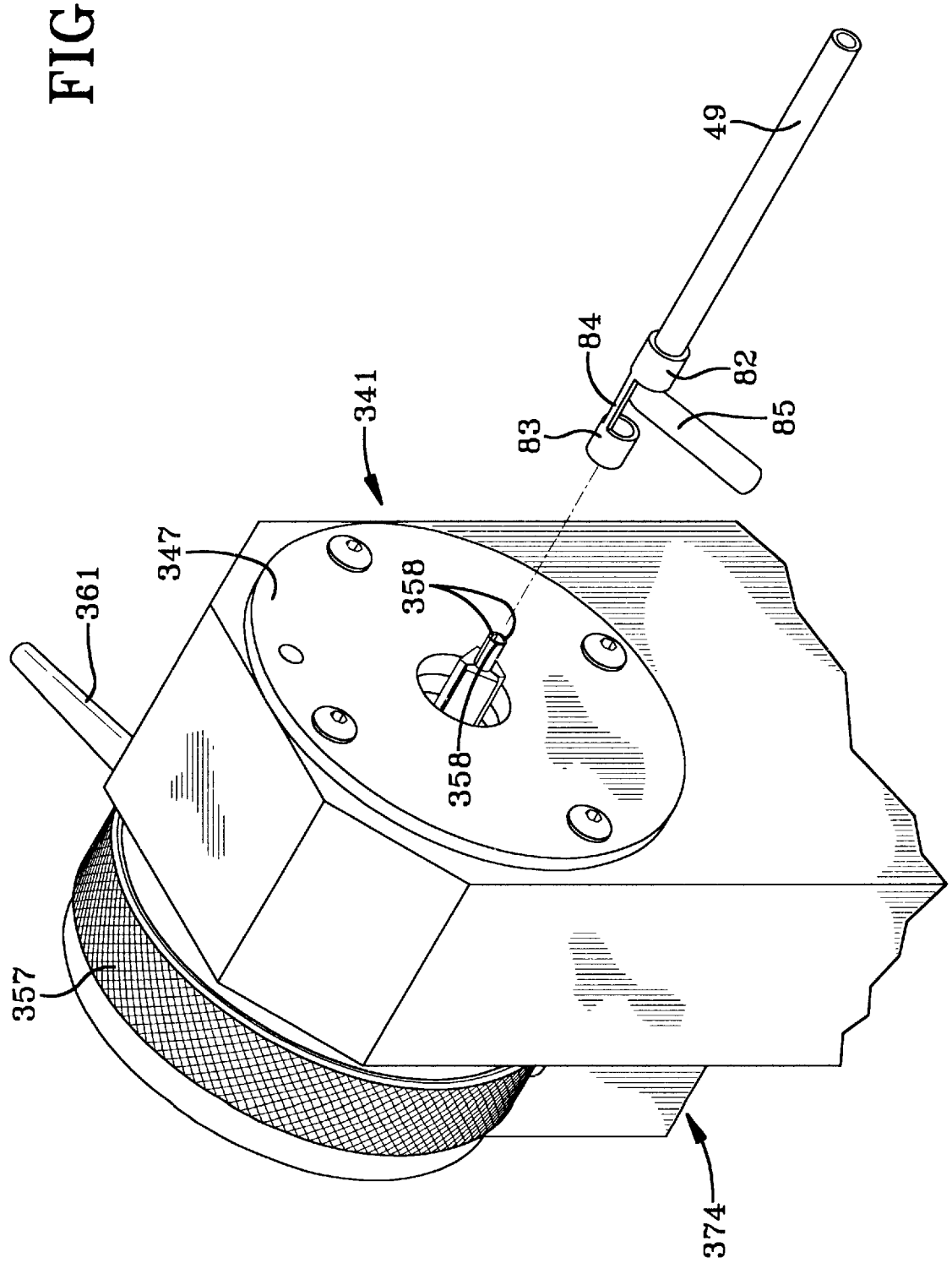
FIG. 82 is a fragmentary perspective view of assembly apparatus closely similar to that of FIG. 74 but adapted with a longer ejector block for the next stage of assembling a pinch valve assembly with the second tubular end portion of the pinch valve element oriented for placing over, i.e., around, the spreader fingers and with the leading end of the length of tubing bent aside.

In FIG. 82 the partly assembled pinch valve depicted in FIG. 80 is shown poised to be further assembled using a second embodiment of the assembly apparatus with a different, i.e., shallower depth stop, in the form of a longer ejector block 368a with an extension 338b. The short end section 85 of the length 49 of flexible tubing between the leading end thereof and the emplaced first tubular segment end portion 82 of the pinch valve element 80 has been bent out of the way so as not to impede sliding the second tubular segment end portion 83 onto the retracted spreader finger portions 358 of the assembly apparatus until the tubular segment end portion contacts the ends of the ejector arms 371a, the shank portion 84 of the pinch valve element 80 being much shorter than the section of tubing 85a disposed between assembled, i.e., emplaced, tubular segment end portions 82 and 83.

Figure 83:
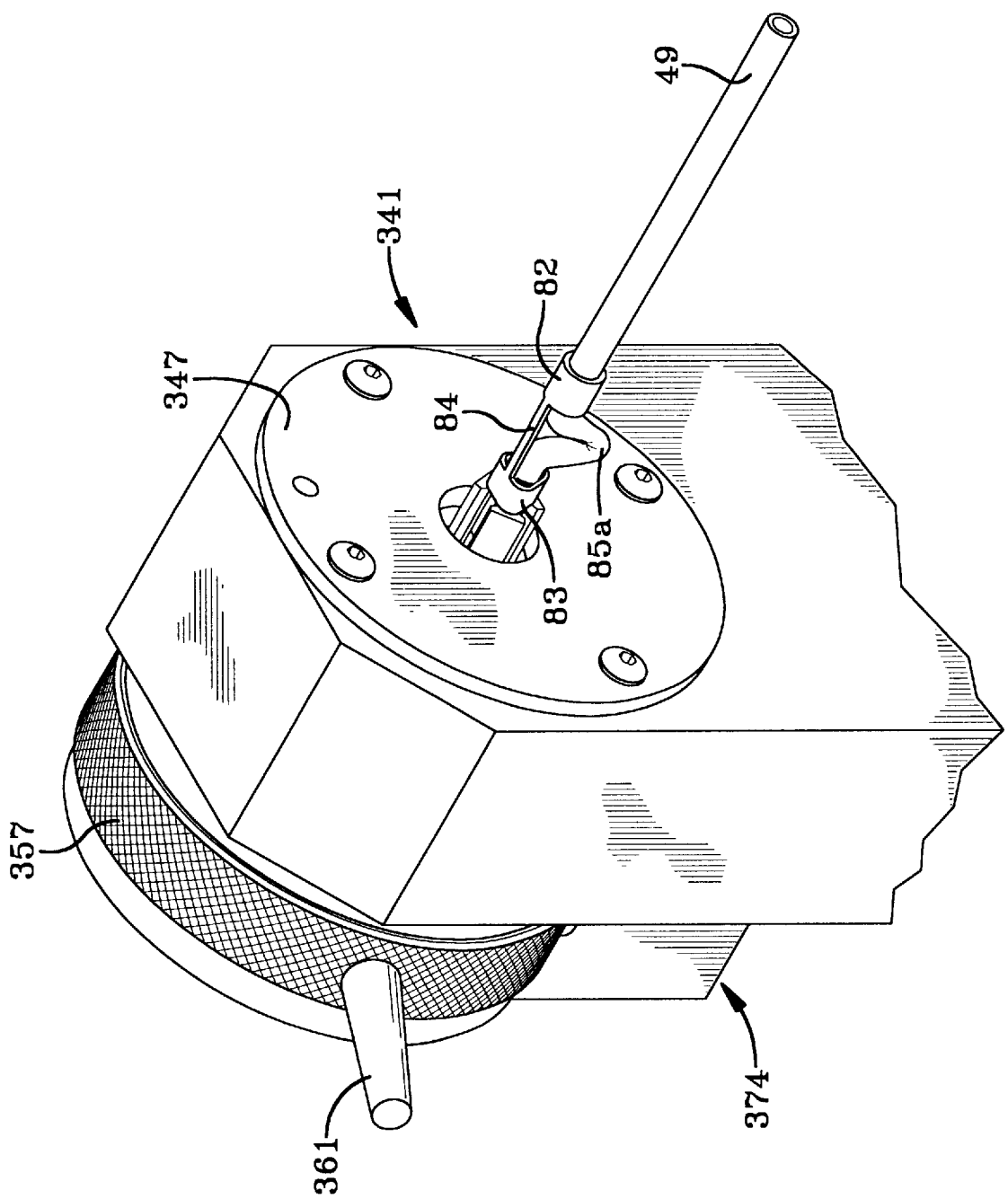
FIG. 83 is a view similar to FIG. 82 showing a further step in the next stage of manufacturing a pinch valve assembly wherein the second tubular end portion is being emplaced on the length of tubing.

The second tubular segment end portion 83 of the pinch valve element is then slid onto the spreader finger portions 358 and the control ring 357 is rotated to spread the spreader finger portions 358 and stretch the second tubular segment end portion 83 of the pinch valve element 80, similar to what is seen in FIG. 77, and the short end section 85 of the length 49 of flexible tubing is bent over sharply and the leading end is slipped inside the spreader finger portions 358 and the stretched second tubular segment end portion 83 and over the central guide rod 369 and up against the ejector block 368a as shown in FIGS. 83 and 84.

As indicated, the longer ejector block 368a, having an extension 338b, provides a stop at a shallower depth of penetration by the end 85 of the length of tubing 49 inside the apparatus. The ejector block 368a is selected to have an extension 338b of appropriate length to provide indexing at a selected depth of penetration desired for the end 85 of the length of tubing 49 in order to achieve proper placement of the second tubular segment end portion 83.

To complete the assembly of the second tubular segment end portion 83 of the pinch valve element, the control ring 357 is rotated back to retract the spreader finger portions 358 closer together to relieve the tension on the second tubular segment end portion 83. To carry out ejection substantially in the same manner as described for the first emplaced tubular segment end portion 82, the ejection piston 362 is pressed forward against the action of the coil spring 363 until the rear edge 378a of the flat lower surface 378 of the rear portion 364 of the ejection piston 362 is stopped by the flanged upper end 377 of the upright leg portion 376 of support element 374, whereupon the length 49 of flexible tubing and the second tubular segment end portion 83 of the pinch valve element emplaced thereon will be found to have been ejected as a unit and the manufacture of the flexible pinch valve is completed.

It is preferred to complete the manufacture of the pinch valve by inserting a small amount of an adhesive such as a room temperature vulcanizing silicone adhesive along the margins of the tubular segment end portions of the valve element.

We claim:

1. An apparatus for supplying an enteral or parenteral fluid to a patient comprising a rotary peristaltic pump and a fluid delivery set;

said rotary peristaltic pump comprising a pump housing having a front body wall and a peristaltic rotor projecting from said front body wall, said housing having first and second retentive receptacles for retaining and supporting said fluid delivery set;

said fluid delivery set comprising a plurality of flexible tubing portions assembled with fluid connection elements therefor, said fluid delivery set including a drip chamber and a retention/connector device, said fluid delivery set defining a continuous fluid pathway from a first end connectable to a supply container of enteral or parenteral fluid to a second end connectable to a device for introducing a fluid into a patient, said fluid pathway extending vertically downwardly through said drip chamber, said drip chamber constructed to be retained in said first retentive receptacle in said pump housing, said fluid pathway further extending downwardly around and against said peristaltic rotor and upwardly through said retention/connector device which is constructed to be retained in said second retentive receptacle in said pump housing, and said fluid pathway extending substantially horizontally from said second receptacle, said fluid pathway defined by said fluid delivery set having a bend of about 78 to about 102 degrees within said retention/connector device.

2. The apparatus of claim 1 wherein the pump housing has a body wall with an upper part and a lower part and the upper part protrudes forwardly over the lower part, and the peristaltic rotor is supported below the protruding upper part on a motor shaft extending forwardly through the lower part of the body wall, the first and second retentive receptacles being formed in the upper part above the peristaltic rotor.

3. The apparatus of claim 2 wherein said first retentive receptacle in said pump housing includes a floor, a substantially vertical guideway formed through the floor, said upper part of said housing below said first retentive receptacle defining a front opening slot, said front opening slot extending a length of said upper part of said housing, said guideway being substantially aligned with a lateral side of said peristaltic rotor.

4. The apparatus of claim 3 wherein the first retentive receptacle of the pump housing has defining walls on three sides and the drip chamber is provided with a retention element attached around the upper part thereof and the retention element is retentively received and supported by the walls and floor of the first retentive receptacle.

5. The apparatus of claim 2 wherein the second retentive receptacle of the pump housing has a floor and a front opening slot is formed therethrough extending to the lower part of the body wall and the slot is substantially aligned with a lateral side of the peristaltic rotor.

6. The apparatus of claim 5 wherein the second retentive receptacle of the pump housing is formed with a connecting horizontal guideway extending towards a lateral side of the pump housing.

7. The apparatus of claim 6 wherein a vertical height of each of the second retentive receptacle of the pump housing and the horizontal guideway does not exceed about 0.5 inch.

8. The apparatus of claim 5 wherein the floor of the second retentive receptacle of the pump housing divided by said slot has a front edge and is formed with an upstanding flange at the front edge of at least a part thereof.

9. The apparatus of claims 1 wherein said bend of said fluid pathway defined by said fluid delivery set is about 85 to about 95 degrees.

10. The apparatus of claim 1 wherein said bend of said fluid pathway defined by the fluid delivery set is positioned within said second retentive receptacle of said pump housing when said fluid delivery set is mounted on said rotary peristaltic pump.

11. The apparatus of claim 1 wherein said bend of said fluid pathway defined by said fluid delivery set has a radius of less than about 0.5 inch.

12. The apparatus of claim 11 wherein the radius of the bend in the fluid pathway does not exceed about 0.375 inch.

13. The apparatus of claim 1 wherein the drip chamber of the fluid delivery set is provided with a retention element around the upper part thereof that is retained by the first retentive receptacle of the pump housing.

14. The apparatus of claim 13 wherein the retention element is provided with a tab.

15. The apparatus of claim 1 wherein the retention/connector device of the fluid delivery set has a retention tab extending laterally thereof that interlocks with the second retentive receptacle of the pump housing.

16. The apparatus of claim 1 wherein the retention/connector device of the fluid delivery set has a tab for grasping extending forwardly therefrom when the device is mounted in the second retentive receptacle of the pump housing.

17. The apparatus of claim 1 wherein the rotary peristaltic pump further comprises a drive motor mounted within the pump housing, a shaft thereof extending forwardly out through the body wall and the peristaltic rotor being mounted on the shaft.

18. The apparatus of claim 1 wherein the flexible tubing portions of the fluid delivery set are at least three in number and are interconnected by the drip chamber and the retention/connector device, the first flexible tubing portion being connected to an inlet of the drip chamber and being connectable to a supply container of fluid for administration to a patient, the second flexible tubing portion being connected to an outlet of the drip chamber and to the retention/connector device, and the third flexible tubing portion being connected to the retention/connector device and being connectable to a device for transmitting a fluid into a patient.

19. The apparatus of claim 18 wherein the peristaltic rotor of the rotary peristaltic pump is equipped with rollers and the second flexible tubing portion of the fluid delivery set is constructed to be held under tension between the outlet of the drip chamber and the connection to the retention/connector device.

20. The apparatus of claim 1 wherein the pump housing has also a top body wall and the first receptacle is formed of the front and top body walls at a juncture thereof and the first receptacle has a floor with the fluid pathway defined by the fluid delivery set extending downwardly through an aperture in the floor connecting to a downwardly extending channel, and the floor has a front opening slot that extends a length of the downwardly extending channel.

21. The apparatus of claim 1 wherein the second retentive receptacle of the pump housing is formed with a floor and the floor is shaped with a front opening slot adapted to receive the retention/connector device of the fluid delivery set, the slotted floor having a front edge and the front edge being formed with an upstanding flange along at least a portion thereof, and the retention/connector device having a lateral retention tab and the retention/connector device with its retention tab being shaped to be retentively held behind the upstanding flange.

22. The apparatus of claim 1 wherein the fluid delivery set further comprises a tension responsive pinch valve operatively associated with a flexible tubing portion.

* * * * *